US008454963B2

(12) United States Patent
Tomlinson et al.

(10) Patent No.: US 8,454,963 B2
(45) Date of Patent: Jun. 4, 2013

(54) TISSUE TARGETED COMPLEMENT MODULATORS

(75) Inventors: Stephen Tomlinson, Mt. Pleasant, SC (US); Richard J. Quigg, Hinsdale, IL (US)

(73) Assignees: MUSC Foundation for Research Development, Charleston, SC (US); University of Chicago, Chicago, IL (US)

( * ) Notice: Subject to any disclaimer, the term of this patent is extended or adjusted under 35 U.S.C. 154(b) by 1925 days.

(21) Appl. No.: 11/116,939

(22) Filed: Apr. 28, 2005

(65) Prior Publication Data

US 2005/0265995 A1    Dec. 1, 2005

Related U.S. Application Data

(63) Continuation-in-part of application No. PCT/US03/36459, filed on Nov. 13, 2003.

(51) Int. Cl.
*A61K 38/00* (2006.01)
*C07K 16/28* (2006.01)
*C07K 14/705* (2006.01)

(52) U.S. Cl.
USPC .............. 424/178.1; 424/185.1; 424/192.1; 424/193.1

(58) Field of Classification Search
None
See application file for complete search history.

(56) References Cited

U.S. PATENT DOCUMENTS

| | | | |
|---|---|---|---|
| 6,180,370 B1 * | 1/2001 | Queen et al. | 435/69.6 |
| 6,458,360 B1 | 10/2002 | Fearon et al. | |
| 6,573,096 B1 * | 6/2003 | Chen | 435/326 |
| 6,713,606 B1 * | 3/2004 | Smith et al. | 530/350 |
| 8,007,804 B2 * | 8/2011 | Tomlinson et al. | 424/178.1 |
| 2012/0014952 A1 * | 1/2012 | Tomlinson et al. | 424/134.1 |

FOREIGN PATENT DOCUMENTS

WO    WO 96/34096    * 10/1996

OTHER PUBLICATIONS

Stange et al, Acta Histochem 98(3): 323-31, abstract only, Jul. 1996.*
Witte et al, Cancer and Metastasis Reviews 17: 155-161, 1998.*
Jones et al, Pharmacogenomics Journal, 1:126-134, 2001.*
Tosatto et al state, Current Pharmaceutical Design; 12:2067-2086, 2006.*
Rudikoff et al, Proc Natl Acad Sci USA 79: 1979, 1982.*
Barrios et al, J Molecular Recognition 17: 332-338, 2004.*
Piatesi et al, ChemBio Chem 5: 460-466, 2004.*
MacCallum et al, Mol. Biol 262: 732-745, 1996.*
Inada et al, American J Pathology 167(2): 327-336, Aug. 2005.*
*Therapeutic interventions in the complement system*, Lambris JD, et al., Eds., Humana Press, Totowa, New Jersey (2000) Chap. 4, p. 75-113 , Chap. 6, 155-171, and Chap. 8, 205-225.

Aguado, MT, et al., Monoclonal antibodies against complement 3 neoantigens for detection of immune complexes and complement activation. Relationship between immune complex levels, state of C3, and numbers of receptors for C3b. *J. Clin. Invest.* 76:1418-1426 (1985).
Bailly, V, et al., Shedding of kidney injury molecule-1, a putative adhesion protein involved in renal regeneration. *J. Biol. Chem.* 277:39739-39748 (2002).
Biancone, L, et al., Alternative pathway activation of complement by cultured human proximal tubular epithelial cells. *Kidney Int.* 45:451-460 (Feb. 1994).
Blouch, K, et al., Molecular configuration and glomerular size selectivity in healthy and nephrotic humans. *Am. J. Physiol.* 273:F430-F437 (1997).
Braun, MC, et al., Renal expression of the C3a receptor and functional responses of primary human proximal tubular epithelial cells. *J. Immunol.* 173:4190-4196 (2004).
Camussi, G, et al., In vivo localization of C3 on the brush border of proximal tubules of kidneys from nephrotic. *Clin Nephrol.* 23:134-141 (Mar. 1985).
Camussi, G, et al., In vitro alternative pathway activation of complement by the brush border of proximal tubules of normal rat kidney. *J Immunol.* 128:1659-1663 (Apr. 1982).
Cosio, FG, et al., Effects of complement activation products on the synthesis of decay accelerating factor and membrane cofactor protein by human mesangial cells. *Kidney. Int.* 46:986-992 (1994).
Couser, WG, Complement inhibitors and glomerulonephritis: Are we there yet? *J Am Soc Nephrol.* 14, 815-818 (Mar. 2003).
Daha, MR, et al., Is the proximal tubular cell a proinflammatory cell? *Nephrol. Dial. Transplant.* 15 Suppl. 6:41-43 (2000).
Eddy, AA, et al.,A relationship between proteinuria and acute tubulointerstitial disease in rats with experimental nephrotic syndrome. *Am. J. Pathol.* 138:1111-1123 (1991).
Fraser, DA, et al., Generation of a recombinant, membrane-targeted form of the complement regulator CD59. *J Biol Chem.* 278:48921-48927 (Dec. 5, 2003).

(Continued)

*Primary Examiner* — Phuong Huynh
(74) *Attorney, Agent, or Firm* — Ballard Spahr LLP

(57) ABSTRACT

Systemic suppression of the complement system has been shown to be effective to treat inflammatory disease, yet at the potential cost of compromising host defense and immune homeostasis. Herein disclosed are methods for antigen-specific targeting of complement inhibitors that show that complement inhibitors targeted to the proximal tubular epithelium protect against tubulointerstitial injury and renal dysfunction in a rat model of nephrosis. It is shown that appropriate targeting of a systemically administered complement inhibitor to a site of disease markedy enhances efficacy and obviates the need to systemically inhibit complement. Additionally, it is shown by specifically inhibiting the terminal pathway of complement, that the membrane attack complex (MAC) plays a key role in proteinuria-induced tubulointerstitial injury, thus establishing the MAC as a valid target for pharmacological intervention in proteinuric disorders. The disclosed are compositions can be used in methods of treating pathogenic diseases and inflammatory conditions by modulating the complement system.

5 Claims, 6 Drawing Sheets

OTHER PUBLICATIONS

Figure 1:
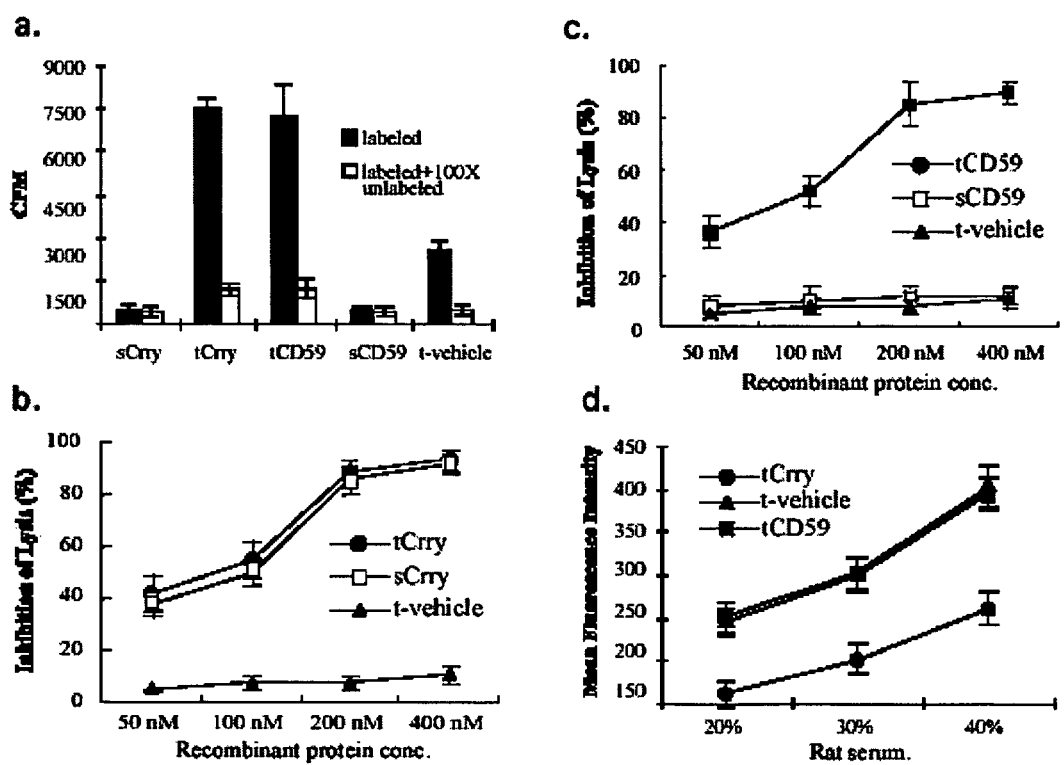

Harris, CL, et al., Tailoring anti-complement therapeutics. *Biochem Soc Trans.* 30:1019-1026 (Nov. 2002).

Higuchi, T, et al., Molecular cloning, genomic structure, and expression analysis of MUC20, a novel mucin protein, up-regulated in injured kidney. *J. Biol. Chem.* 279:1968-1979 (2004).

Higuchi, T, et al., MUC20 suppresses the hepatocyte growth factor-induced Grb2-Ras pathway by binding to a multifunctional docking site of met. *Mol. Cell Biol.* 24:7456-7468 (2004).

Hiramatsu, H, et al., The structure and function of human dipeptidyl peptidase IV, possessing a unique eight-bladed beta-propeller fold. *Biochem. Biophys. Res. Commun.* 302:849-854 (2003).

Hori, Y, et al., Crry, a complement regulatory protein, modulates renal interstitial disease induced by proteinuria. *Kidney Int.* 56:2096-2106 (Dec. 1999).

Hsu, SI, et al., Chronic progression of tubulointerstitial damage in proteinuric renal disease is mediated by complement activation: A therapeutic role for complement inhibitors? *J Am Soc Nephrol.* 14:S186-A191 (Jul. 2003).

Huang, J, et al., Neuronal protection in stroke by an sLe-Glycosylated complement inhibitory protein. *Science* 285:595-599 (Jul. 23, 1999).

Hughes, TR, et al., Isolation and characterization of a membrane protein from rat erythrocytes which inhibits lysis by the membrane attack complex of rat complement. *Biochem. J.* 284:169 (1992).

Hussain, MM, et al., The mammalian low-density lipoprotein receptor family. *Annu. Rev. Nutr.* 19:141-172 (1999).

Ichida, S, et al., Localization of the complement regulatory proteins in the normal human kidney. *Kidney Int.* 46:89-96 (1994).

Ichimura, T, et al., Kidney injury molecule-1 (KIM-1), a putative epithelial cell adhesion molecule containing a novel immunoglobulin domain, is up-regulated in renal cells after injury. *J. Biol. Chem.* 273-4135-4142 (1998).

Kim, Yu, et al., Mouse complement regulatory Protein Crry/p65 uses the specific mechanisms of both human decay-accelerating factor and membrane cofactor protein. *Journal of Experimental Medicine.* 181:151-159 (1995).

Kyriakides, C, et al., Moderation of skeletal muscle reperfusion injury by a sLe x-glycosylated complement inhibitory protein. *Am J Physiol Cell Physiol.* 281:C224-C230 (Jul. 2001).

Meldrum, KK, et al., TNF-α-dependent bilateral renal injury is induced by unilateral renal ischemiareperfusion. *Am. J. Physiol. Heart Circ. Physiol.* 282:H540 (2002).

Mendrick, DL, et al. Methods in laboratory investigation Momoclonal antibodies against rat glomerular antigens : Production and Specificity. *Laboratory Investigation.* 49:107-117 (1983).

Mendrick, DL, et al., I. Induction of proteinuria in the rat by a monoclonal antibody against SGP-115/107. *Kidney Int.* 33:818-830. (1988).

Morgan, BP, Measurement of complement hemolytic activity. In *Complement Methods and Protocols.* B. P. Morgan, ed. Humana Press, Totowa, NJ, p. 61-71 (2000).

Morita, Y, et al., Complement activation products in the urine from proteinuric patients. *J Am Soc Nephrol.* 11:700-707 (Apr. 2000).

Mosolits, S, et al., Membrane attack complex and membrane cofactor protein are related to tubulointerstitial inflammation in various human glomerulopathies. *Nephron.* 75:179-187 (1997).

Mulligan, MS, et al., Endothelial Targeting and Enhanced Intiinflammatory Effects of Complement Inhibitors Possessing Sialyl Lewis Moities. *J Immunol.* 162:4952-4959 (Apr. 15, 1999).

Nangaku, M, et al., Cellular Response to Injury in Membranous Nephropathy. *J Am Soc Nephrol.* 16:1195-1204 (Mar. 30, 2005).

Nangaku, M, et al., C6 Mediates chronic progression of tubulointerstitial damage in rats with remnant kidneys. *J Am Soc Nephrol* 13, 928-936 (Apr. 2002).

Nath, KA, et al., Pathophysiology of chronic tubulo-interstitial disease in rats. Interactions of dietary acid load, ammonia, and complement component C3. *J. Clin. Invest.* 76:667-675 (1985).

Nath, KA, Tubulointerstitial changes as a major determinant in the progression of renal damage. *Am. J. Kid. Dis.* 20:1-17 (1992).

Nauta, AJ, et al., Human renal epithelial cells produce the long pentraxin PTX3. *Kidney Int.* 67:543-553 (2005).

Nomura, A, et al., Role of complement in acute tubulointerstitial injury of rats with aminoucleoside nephrosis. *Am J Pathol* 151:539-547 (Aug. 1997).

Oefner, C, et al., Structure of human neutral endopeptidase (Neprilysin) complexed with phosphoramidon. *J. Mol. Biol.* 296:341-349 (2000).

Ogrodowsi, JL, et al., Measurement of SC5b-9 in urine in patients with the nephrotic syndrome. *Kidney Int.* 40:1141-1147 (1991).

Peake, PW, et al., The effect of pH and nucleophiles on complement activation by human proximal tubular epithelial cells. *Nephroi. Dial. Transplant.* 17:745-752 (2002).

Piddlesden, SJ, et al., Soluble recombinant complement receptor 1 inhibits inflammation and demyelination in antibody-mediated demyleianting esperimental allergic encephalomyelitis. *J.Immunol.* 152:5477-5484 (1994).

Pippin, JW, et al., DNA damage is a novel response to sublytic complement C5b-9-induced injury in podocytes. *J. Clin. Invest.* 111:877-885 (2003).

Quigg, RJ, et al., Anti-Fx1A produces complement-dependent cytotoxicity of glomerular epithelial cells. *Kidney Int.* 34:43-52 (1988).

Quigg, RJ, et al., Use of complement inhibitors in tissue injury. *Trends Mol Med* 8:430-436 (Sep. 2002).

Quigg, RJ, We need to inhibit complement in glomerular proteinuria. *Kidney Int* 56:2314-2315 (1999).

Rushmere, NK, et al., Molecular cloning of the rat analogue of human CD59: structural comparison with human CD59 and identification of a putative active site. *Biochem. J.* 304:595 (1994).

Rushmere, NK, et al., Production and functional characterization of a soluble recombinant form of mouse CD59. *Immunology* 99:326 (2000).

Sakurada, C, et al., Molecular cloning of the rat complement regulatory protein, 5I2 antigen. *Biochem. Biophys. Res. Commun.* 198:819 (1994).

Schulze, M, et al., Elevated urinary excretion of the C5b-9 compex in membranous nephropathy. *Kidney Int* 40:533-538 (Sep. 1991).

Sharkey, R.M., et al. Biodistribution and radiation dose estimates for yttrium- and iodine-Iabeledl monoclonal antibody IgG and fragments in nude mice bearing human colonic tumor xenografts. *Cancer Res.* 50:2330-2336 (1990).

Sharkey, RM, et al., Rapid blood clearance of immunoglobulin G2a and immunoglobulin G2b in nude mice. *Cancer Res.* 51:3102 (1991).

Sheerin, NS, et al., Leaked protein and interstitial damage in the kidney: is complement the missing link? *Clin Exp Immunol* 130:1-3 (2002).

Shin, SU, et al., Expression and characterization of an antibody binding specificity joined to insulin-like growth factor 1: potential applications for cellular targeting. *Proc. Natl. Acad. Sci. U. S. A.* 87:5322-5326 (1990).

Shin, SU, et al., Production and properties of chimeric antibody molecules. *Methods Enzymol.* 178:459-476 (1989).

Smith et al., Membrane-targeted complement inhibitors. *Mol. Immunol.* 38:249-255 (2001).

Song, H, et al., Complement receptor 2-mediated targeting of complement inhibitors to sites of complement activation. *J Clin Invest* 111(12):1875-1885 (Jun. 2003).

Spitzer, D, et al., ScFv-mediated in vivo targeting of DAF to erythrocytes inhibits lysis by by complement. *Mol Immunol* 40:911-919 (Feb. 2004).

Tam, JP, Synthetic peptide vaccine design: synthesis and properties of a high-density multiple antigenic peptide system. *Proc. Natl. Acad. Sci. U. S. A.* 85:5409-5413 (1988).

Tang, S, et al., Role of complement in tubulointerstitial injury from proteinuria. *Kidney Blood Press Res.* 25:120-126 (2002).

Tang, S, et al., Transferrin but not albumin mediates stimulation of complement C3 biosynthesis in human proximal tubular epithelial cells. *Am. J. Kidney Dis.* 37:94-103 (2001).

Timmerman, JJ, et al., Differential expression of complement components in human fetal and adult kidneys. *Kidney Int.* 49:730-740 (1996).

Walport, MJ, et al., Complement and systemic lupus erythematosus. *Arthritis Res*. 4 Suppl. 3:S279-S293 (2002).

Weihofen, WA, et al., Crystal structure of CD26/dipeptidyl-peptidase IV in complex with adenosine deaminase reveals a highly amphiphilic interface. *J. Biol. Chem*. 279:43330-43335 (2004).

Whiteside, C, et al., Glomerular epithelial detachment, not reduced charge density, correlates with proteinuria in adriamycin and puromycin nephrosis. *Lab Invest* 61:650-660 (Dec. 1989).

Zacharowski, K, et al., Reduction of myocardial infarct size with sCR1sLe, an alternatively glycosylated form of human soluble complement receptor type 1 (sCR1), possessing sialyl Lewis x. *Br J Pharmacol*. 128:45-52 (Nov. 1999).

Zahedi, R, et al., The C5a receptor is expressed by human renal proximal tubular epithelial cells. *Clin. Exp. Immunol*. 121:226-233 (2000).

Zhang et al., Targeting of Functional Anitbody-Decay accelerating Factor Fusion Proteins to Cell Surface. *J. Biol. Chem*. 276(29):27290-27295 (Jul. 2001).

Zhang, HF, et al., Targeting of functional antibody-CD59 fusion proteins to a cell surface. *J.Clin.invest*. 103:55-66 (1999).

Zoja, C, et al., Proteinuria and phenotypic change of proximal tubular cells. *J. Am. Soc. Nephrol*. 14 Suppl. 1:S36-S41 (2003).

\* cited by examiner

SEQUENCE LISTING

<160> NUMBER OF SEQ ID NOS: 27

<210> SEQ ID NO 1
<211> LENGTH: 1041
<212> TYPE: DNA
<213> ORGANISM: Artificial Sequence
<220> FEATURE:

<223> OTHER INFORMATION: Description of Artificial Sequence;
      note=synthetic construct

<400> SEQUENCE: 1

```
gactgtggcc ttcccccaga tgtacctaat gcccagccag ctttggaagg ccgtacaagt      60
tttcccgagg atactgtaat aacgtacaaa tgtgaagaaa gctttgtgaa aattcctggc     120
gagaaggact cagtgatctg ccttaagggc agtcaatggt cagatattga agagttctgc     180
aatcgtagct gcgaggtgcc aacaaggcta aattctgcat ccctcaaaca gccttatatc     240
actcagaatt attttccagt cggtactgtt gtggaatatg agtgccgtcc aggttacaga     300
agagaacctt ctctatcacc aaaactaact tgccttcaga atttaaaatg gtccacagca     360
gtcgaatttt gtaaaaagaa atcatgccct aatccgggag aaatacgaaa tggtcagatt     420
gatgtaccag gtggcatatt atttggtgca accatctcct tctcatgtaa cacagggtac     480
aaattatttg gctcgacttc tagttttttgt cttatttcag gcagctctgt ccagtggagt     540
gacccgttgc cagagtgcag agaaatttat tgtccagcac caccacaaat tgacaatgga     600
ataattcaag gggaacgtga ccattatgga tatagacagt ctgtaacgta tgcatgtaat     660
aaaggattca ccatgattgg agagcactct atttattgta ctgtgaataa tgatgaagga     720
gagtggagtg gcccaccacc tgaatgcaga ggaaaatctc taacttccaa ggtcccacca     780
acagttcaga aacctaccac agtaaatgtt ccaactacag aagtctcacc aacttctcag     840
aaaaccacca caaaaaccac cacaccaaat gctcaagcaa cacggagtac acctgtttcc     900
aggacaacca agcattttca tgaaacaacc caaataaag gaagtggaac cacttcaggt     960
actacccgtc ttctatctgg gcacacgtgt ttcacgttga caggtttgct tgggacgcta    1020
gtaaccatgg gcttgctgac t                                             1041
```

<210> SEQ ID NO 2
<211> LENGTH: 380
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 2

```
Met Thr Val Ala Arg Pro Ser Val Pro Ala Ala Leu Pro Leu Leu Gly
  1               5                  10                  15

Glu Leu Pro Arg Leu Leu Leu Val Leu Leu Cys Leu Pro Ala Val
             20                  25                  30

Trp Asp Cys Gly Leu Pro Pro Asp Val Pro Asn Ala Gln Pro Ala Leu
         35                  40                  45

Glu Gly Arg Thr Ser Phe Pro Glu Asp Thr Val Ile Thr Tyr Lys Cys
     50                  55                  60

Glu Glu Ser Phe Val Lys Ile Pro Gly Glu Lys Asp Ser Val Ile Cys
 65                  70                  75                  80

Leu Lys Gly Ser Gln Trp Ser Asp Ile Glu Glu Phe Cys Asn Arg Ser
                 85                  90                  95

Cys Glu Val Pro Thr Arg Leu Asn Ser Ala Ser Leu Lys Gln Pro Tyr
            100                 105                 110

Ile Thr Gln Asn Tyr Phe Pro Val Gly Thr Val Glu Tyr Glu Cys
        115                 120                 125

Arg Pro Gly Tyr Arg Arg Glu Pro Ser Leu Ser Pro Lys Leu Thr Cys
    130                 135                 140

Leu Gln Asn Leu Lys Trp Ser Thr Ala Val Glu Phe Cys Lys Lys Lys
```

```
                    145                 150                 155                 160
Ser Cys Pro Asn Pro Gly Glu Ile Arg Asn Gly Gln Ile Asp Val Pro
                165                 170                 175

Gly Gly Ile Leu Phe Gly Ala Thr Ile Ser Phe Ser Cys Asn Thr Gly
            180                 185                 190

Tyr Lys Leu Phe Gly Ser Thr Ser Phe Cys Leu Ile Ser Gly Ser
        195                 200                 205

Ser Val Gln Trp Ser Asp Pro Leu Pro Glu Cys Arg Glu Ile Tyr Cys
    210                 215                 220

Pro Ala Pro Pro Gln Ile Asp Asn Gly Ile Ile Gln Gly Glu Arg Asp
225                 230                 235                 240

His Tyr Gly Tyr Arg Gln Ser Val Thr Tyr Ala Cys Asn Lys Gly Phe
                245                 250                 255

Thr Met Ile Gly Glu His Ser Ile Tyr Cys Thr Val Asn Asn Asp Glu
            260                 265                 270

Gly Glu Trp Ser Gly Pro Pro Glu Cys Arg Gly Lys Ser Leu Thr
        275                 280                 285

Ser Lys Val Pro Pro Thr Val Gln Lys Pro Thr Thr Val Asn Val Pro
    290                 295                 300

Thr Thr Glu Val Ser Pro Thr Ser Gln Lys Thr Thr Thr Lys Thr Thr
305                 310                 315                 320

Thr Pro Asn Ala Gln Ala Thr Arg Ser Thr Pro Val Ser Arg Thr Thr
                325                 330                 335

Lys His Phe His Glu Thr Thr Pro Asn Lys Gly Ser Gly Thr Thr Ser
            340                 345                 350

Gly Thr Thr Arg Leu Leu Ser Gly His Thr Cys Phe Thr Leu Thr Gly
        355                 360                 365

Leu Leu Gly Thr Leu Val Thr Met Gly Leu Leu Thr
370                 375                 380

<210> SEQ ID NO 3
<211> LENGTH: 306
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 3
cagtgctaca actgtcctaa cccaactgct gactgcaaaa cagccgtcaa ttgttcatct      60
gattttgatg cgtgtctcat taccaaagct gggttacaag tgtataacaa gtgttggaag     120
tttgagcatt gcaatttcaa cgacgtcaca acccgcttga gggaaaatga gctaacgtac     180
tactgctgca agaaggacct gtgtaacttt aacgaacagc ttgaaaatgg tgggacatcc     240
ttatcagaga aaacagttct tctgctggtg actccatttc tggcagcagc ctggagcctt     300
catccc                                                                306

<210> SEQ ID NO 4
<211> LENGTH: 126
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 4

Met Gly Ile Gln Gly Gly Ser Val Leu Phe Gly Leu Leu Leu Val Leu
1               5                   10                  15
```

Ala Val Phe Cys His Ser Gly His Gln Cys Tyr Asn Cys Pro Asn Pro
            20                  25                  30

Thr Ala Asp Cys Lys Thr Ala Val Asn Cys Ser Ser Asp Phe Asp Ala
            35                  40                  45

Cys Leu Ile Thr Lys Ala Gly Leu Gln Val Tyr Asn Lys Cys Trp Lys
 50                  55                  60

Phe Glu His Cys Asn Phe Asn Asp Val Thr Thr Arg Leu Arg Glu Asn
 65                  70                  75                  80

Glu Leu Thr Tyr Tyr Cys Cys Lys Lys Asp Leu Cys Asn Phe Asn Glu
                85                  90                  95

Gln Leu Glu Asn Gly Gly Thr Ser Leu Ser Glu Lys Thr Val Leu Leu
            100                 105                 110

Leu Val Thr Pro Phe Leu Ala Ala Ala Trp Ser Leu His Pro
            115                 120                 125

<210> SEQ ID NO 5
<211> LENGTH: 5994
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 5
caatgcaatg ccccagaatg gcttccattt gccaggccta ccaacctaac tgatgagttt      60
gagtttccca ttgggacata tctgaactat gaatgccgcc ctggttattc cggaagaccg     120
ttttctatca tctgcctaaa aaactcagtc tggactggtg ctaaggacag gtgcagacgt     180
aaatcatgtc gtaatcctcc agatcctgtg aatggcatgg tgcatgtgat caaaggcatc     240
cagttcggat cccaaattaa atattcttgt actaaaggat accgactcat tggttcctcg     300
tctgccacat gcatcatctc aggtgatact gtcatttggg ataatgaaac acctatttgt     360
gacagaattc cttgtgggct acccccacc atcaccaatg agatttcat tagcaccaac      420 agagagaatt tcactatgg atcagtggtg acctaccgct gcaatcctgg aagcggaggg     480
agaaaggtgt ttgagcttgt gggtgagccc tccatatact gcaccagcaa tgacgatcaa     540
gtgggcatct ggagcggccc cgcccctcag tgcattatac ctaacaaatg cacgcctcca     600
aatgtggaaa atgaatatt ggtatctgac aacagaagct tattttcctt aaatgaagtt      660
gtggagttta ggtgtcagcc tggctttgtc atgaaaggac cccgccgtgt gaagtgccag     720
gccctgaaca atgggagcc ggagctacca agctgctcca gggtatgtca gccacctcca     780
gatgtcctgc atgctgagcg tacccaaagg gacaaggaca cttttcacc tgggcaggaa     840 gtgttctaca gctgtgagcc cggctacgac ctcagagggg ctgcgtctat gcgctgcaca     900
ccccagggag actggagccc tgcagccccc acatgtgaag tgaaatcctg tgatgacttc     960
atgggccaac ttcttaatgg ccgtgtgcta tttccagtaa atctccagct ggagcaaaa     1020 gtggattttg tttgtgatga aggatttcaa ttaaaaggca gctctgctag ttactgtgtc    1080
ttggctggaa tggaaagcct ttggaatagc agtgttccag tgtgtgaaca aatcttttgt    1140
ccaagtcctc cagtattcc taatgggaga cacacaggaa aacctctgga agtctttccc    1200
tttgaaaaag cagtaaatta cacatgcgac ccccacccag acagagggac gagcttcgac    1260
ctcattggag agagcaccat ccgctgcaca agtgaccctc aagggaatgg ggtttggagc    1320
agccctgccc ctcgctgtgg aattctgggt cactgtcaag ccccagatca tttttctgttt    1380 gccaagttga aaacccaaac caatgcatct gactttccca ttgggacatc tttaaagtac    1440

```
gaatgccgtc ctgagtacta cgggaggcca ttctctatca catgtctaga taacctggtc    1500
tggtcaagtc ccaaagatgt ctgtaaacgt aaatcatgta aaactcctcc agatccagtg    1560
aatggcatgg tgcatgtgat cacagacatc caggttggat ccagaatcaa ctattcttgt    1620
actacagggc accgactcat tggtcactca tctgctgaat gtatcctctc gggcaatgct    1680
gcccattgga gcacgaagcc gccaatttgt caacgaattc cttgtgggct acccccacc     1740 atcgccaatg gagatttcat tagcaccaac agagagaatt ttcactatgg atcagtggtg    1800
acctaccgct gcaatcctgg aagcggaggg agaaaggtgt tgagcttgt gggtgagccc     1860 tccatatact gcaccagcaa tgacgatcaa gtgggcatct ggagcggccc ggcccctcag    1920
tgcattatac ctaacaaatg cacgcctcca aatgtggaaa atggaatatt ggtatctgac    1980
aacagaagct tattttcctt aaatgaagtt gtggagttta ggtgtcagcc tggctttgtc    2040
atgaaaggac cccgccgtgt gaagtgccag gccctgaaca aatgggagcc ggagctacca    2100
agctgctcca gggtatgtca gccacctcca gatgtcctgc atgctgagcg tacccaaagg    2160
gacaaggaca acttttcacc cgggcaggaa gtgttctaca gctgtgagcc cggctatgac    2220
ctcagagggg ctgcgtctat gcgctgcaca ccccagggag actggagccc tgcagccccc    2280
acatgtgaag tgaaatcctg tgatgacttc atgggccaac ttcttaatgg ccgtgtgcta    2340
tttccagtaa atctccagct tggagcaaaa gtggattttg tttgtgatga aggatttcaa    2400
ttaaaaggca gctctgctag ttattgtgtc ttggctggaa tggaaagcct tggaatagc     2460 agtgttccag tgtgtgaaca aatcttttgt ccaagtcctc cagttattcc taatgggaga    2520
cacacaggaa aacctctgga agtctttccc tttggaaaag cagtaaatta cacatgcgac    2580
ccccacccag acagagggac gagcttcgac ctcattggag agagcaccat ccgctgcaca    2640
agtgaccctc aagggaatgg ggtttggagc agccctgccc ctcgctgtgg aattctgggt    2700
cactgtcaag ccccagatca ttttctgttt gccaagttga aacccaaac caatgcatct     2760 gactttccca ttgggacatc tttaaagtac gaatgccgtc ctgagtacta cgggaggcca    2820
ttctctatca catgtctaga taacctggtc tggtcaagtc ccaaagatgt ctgtaaacgt    2880
aaatcatgta aaactcctcc agatccagtg aatggcatgg tgcatgtgat cacagacatc    2940
caggttggat ccagaatcaa ctattcttgt actacagggc accgactcat tggtcactca    3000
tctgctgaat gtatcctctc aggcaatact gcccattgga gcacgaagcc gccaatttgt    3060
caacgaattc cttgtgggct accccaacc atcgccaatg gagatttcat tagcaccaac     3120
agagagaatt ttcactatgg atcagtggtg acctaccgct gcaatcttgg aagcagaggg    3180
agaaaggtgt tgagcttgt gggtgagccc tccatatact gcaccagcaa tgacgatcaa     3240
gtgggcatct ggagcggccc cgcccctcag tgcattatac ctaacaaatg cacgcctcca    3300
aatgtggaaa atggaatatt ggtatctgac aacagaagct tattttcctt aaatgaagtt    3360
gtggagttta ggtgtcagcc tggctttgtc atgaaaggac cccgccgtgt gaagtgccag    3420
gccctgaaca aatgggagcc agagttacca agctgctcca gggtgtgtca gccgcctcca    3480
gaaatcctgc atggtgagca taccccaagc catcaggaca acttttcacc tgggcaggaa    3540
gtgttctaca gctgtgagcc tggctatgac ctcagagggg ctgcgtctct gcactgcaca    3600
ccccagggag actggagccc tgaagccccg agatgtgcag tgaaatcctg tgatgacttc    3660
ttgggtcaac tccctcatgg ccgtgtgcta tttccactta atctccagct tggggcaaag    3720
gtgtcctttg tctgtgatga agggtttcgc ttaaagggca gttccgttag tcattgtgtc    3780
ttggttggaa tgagaagcct tggaataac agtgttcctg tgtgtgaaca tatctttgt      3840
```

```
ccaaatcctc cagctatcct taatgggaga cacacaggaa ctccctctgg agatattccc    3900
tatggaaaag aaatatctta cacatgtgac ccccacccag acagagggat gaccttcaac    3960
ctcattgggg agagcaccat ccgctgcaca agtgaccctc atgggaatgg ggtttggagc    4020
agccctgccc ctcgctgtga actttctgtt cgtgctggtc actgtaaaac cccagagcag    4080
tttccatttg ccagtcctac gatcccaatt aatgactttg agtttccagt cgggacatct    4140
ttgaattatg aatgccgtcc tgggtatttt gggaaaatgt tctctatctc ctgcctagaa    4200
aacttggtct ggtcaagtgt tgaagacaac tgtagacgaa atcatgtgg acctccacca    4260 gaacccttca atggaatggt gcatataaac acagatacac agtttggatc aacagttaat    4320
tattcttgta atgaagggtt tcgactcatt ggttccccat ctactacttg tctcgtctca    4380
ggcaataatg tcacatggga taagaaggca cctatttgtg agatcatatc ttgtgagcca    4440
cctccaacca tatccaatgg agacttctac agcaacaata gaacatcttt tcacaatgga    4500
acggtggtaa cttaccagtg ccacactgga ccagatggaa acagctgtt tgagcttgtg    4560 ggagaacggt caatatattg caccagcaaa gatgatcaag ttggtgtttg gagcagccct    4620
cccccctcgt gtatttctac taataaatgc acagctccag aagttgaaaa tgcaattaga    4680
gtaccaggaa acaggagttt cttttccctc actgagatca tcagatttag atgtcagccc    4740
gggtttgtca tggtagggtc ccacactgtg cagtgccaga ccaatggcag atgggggccc    4800
aagctgccac actgctccag ggtgtgtcag ccgcctccag aaatcctgca tggtgagcat    4860
accctaagcc atcaggacaa cttttcacct gggcaggaag tgttctacag ctgtgagccc    4920
agctatgacc tcagaggggc tgcgtctctg cactgcacgc cccagggaga ctggagccct    4980
gaagccccta gatgtacagt gaaatcctgt gatgacttcc tgggccaact ccctcatggc    5040
cgtgtgctac ttccacttaa tctccagctt ggggcaaagg tgtcctttgt ttgcgatgaa    5100
gggttccgat taaaaggcag gtctgctagt cattgtgtct tggctggaat gaaagccctt    5160
tggaatagca gtgttccagt gtgtgaacaa atcttttgtc caaatcctcc agctatcctt    5220
aatgggagac acacaggaac tccctttgga gatattccct atggaaaaga aatatcttac    5280
gcatgcgaca cccacccaga cagagggatg accttcaacc tcattgggga gagctccatc    5340
cgctgcacaa gtgaccctca agggaatggg gtttggagca gccctgcccc tcgctgtgaa    5400 cttttctgttc ctgctgcctg cccacatcca cccaagatcc aaaacgggca ttacattgga    5460
ggacacgtat ctctatatct tcctgggatg acaatcagct acacttgtga ccccggctac    5520
ctgttagtgg gaaagggctt catttttctgt acagaccagg gaatctggag ccaattggat    5580
cattattgca aagaagtaaa ttgtagcttc ccactgttta tgaatggaat ctcgaaggag    5640
ttagaaatga aaaagtata tcactatgga gattatgtga ctttgaagtg tgaagatggg    5700
tatactctgg aaggcagtcc ctggagccag tgccaggcgg atgacagatg ggaccctcct    5760
ctggccaaat gtacctctcg tgcacatgat gctctcatag ttggcacttt atctggtacg    5820 atcttctta ttttactcat cattttcctc tcttggataa ttctaaagca cagaaaaggc    5880
aataatgcac atgaaaaccc taagaagtg gctatccatt tacattctca aggaggcagc    5940
agcgttcatc cccgaactct gcaaacaaat gaagaaaata gcagggtcct tcct          5994

<210> SEQ ID NO 6
<211> LENGTH: 2048
<212> TYPE: PRT
<213> ORGANISM: Artificial Sequence
<220> FEATURE:
<223> OTHER INFORMATION: Description of Artificial Sequence;
``` note=synthetic construct

<400> SEQUENCE: 6

```
Met Cys Leu Gly Arg Met Gly Ala Ser Ser Pro Arg Ser Pro Glu Pro
 1               5                  10                  15
Val Gly Pro Ala Pro Gly Leu Pro Phe Cys Cys Gly Gly Ser Leu
             20                  25                  30
Leu Ala Val Val Val Leu Leu Ala Leu Pro Val Ala Trp Gly Gln Cys
             35                  40                  45
Asn Ala Gln Cys Asn Ala Pro Glu Trp Leu Pro Phe Ala Arg Pro Thr
 50                  55                  60
Asn Leu Thr Asp Glu Phe Glu Phe Pro Ile Gly Thr Tyr Leu Asn Tyr
 65                  70                  75                  80
Glu Cys Arg Pro Gly Tyr Ser Gly Arg Pro Phe Ser Ile Ile Cys Leu
                 85                  90                  95
Lys Asn Ser Val Trp Thr Gly Ala Lys Asp Arg Cys Arg Arg Lys Ser
                100                 105                 110
Cys Arg Asn Pro Pro Asp Pro Val Asn Gly Met Val His Val Ile Lys
                115                 120                 125
Gly Ile Gln Phe Gly Ser Gln Ile Lys Tyr Ser Cys Thr Lys Gly Tyr
            130                 135                 140
Arg Leu Ile Gly Ser Ser Ser Ala Thr Cys Ile Ile Ser Gly Asp Thr
145                 150                 155                 160
Val Ile Trp Asp Asn Glu Thr Pro Ile Cys Asp Arg Ile Pro Cys Gly
                165                 170                 175
Leu Pro Pro Thr Ile Thr Asn Gly Asp Phe Ile Ser Thr Asn Arg Glu
                180                 185                 190
Asn Phe His Tyr Gly Ser Val Val Thr Tyr Arg Cys Asn Pro Gly Ser
            195                 200                 205
Gly Gly Arg Lys Val Phe Glu Leu Val Gly Glu Pro Ser Ile Tyr Cys
        210                 215                 220
Thr Ser Asn Asp Asp Gln Val Gly Ile Trp Ser Gly Pro Ala Pro Gln
225                 230                 235                 240
Cys Ile Ile Pro Asn Lys Cys Thr Pro Pro Asn Val Glu Asn Gly Ile
                245                 250                 255
Leu Val Ser Asp Asn Arg Ser Leu Phe Ser Leu Asn Glu Val Val Glu
            260                 265                 270
Phe Arg Cys Gln Pro Gly Phe Val Met Lys Gly Pro Arg Arg Val Lys
        275                 280                 285
Cys Gln Ala Leu Asn Lys Trp Glu Pro Glu Leu Pro Ser Cys Ser Arg
290                 295                 300
Val Cys Gln Pro Pro Asp Val Leu His Ala Glu Arg Thr Gln Arg
305                 310                 315                 320
Asp Lys Asp Asn Phe Ser Pro Gly Gln Glu Val Phe Tyr Ser Cys Glu
                325                 330                 335
Pro Gly Tyr Asp Leu Arg Gly Ala Ala Ser Met Arg Cys Thr Pro Gln
            340                 345                 350
Gly Asp Trp Ser Pro Ala Ala Pro Thr Cys Glu Val Lys Ser Cys Asp
        355                 360                 365
Asp Phe Met Gly Gln Leu Leu Asn Gly Arg Val Leu Phe Pro Val Asn
    370                 375                 380
Leu Gln Leu Gly Ala Lys Val Asp Phe Val Cys Asp Glu Gly Phe Gln
385                 390                 395                 400
Leu Lys Gly Ser Ser Ala Ser Tyr Cys Val Leu Ala Gly Met Glu Ser
```

-continued

```
                    405                 410                 415
Leu Trp Asn Ser Ser Val Pro Val Cys Glu Gln Ile Phe Cys Pro Ser
                420                 425                 430

Pro Pro Val Ile Pro Asn Gly Arg His Thr Gly Lys Pro Leu Glu Val
            435                 440                 445

Phe Pro Phe Gly Lys Ala Val Asn Tyr Thr Cys Asp Pro His Pro Asp
        450                 455                 460

Arg Gly Thr Ser Phe Asp Leu Ile Gly Glu Ser Thr Ile Arg Cys Thr
465                 470                 475                 480

Ser Asp Pro Gln Gly Asn Gly Val Trp Ser Ser Pro Ala Pro Arg Cys
                485                 490                 495

Gly Ile Leu Gly His Cys Gln Ala Pro Asp His Phe Leu Phe Ala Lys
            500                 505                 510

Leu Lys Thr Gln Thr Asn Ala Ser Asp Phe Pro Ile Gly Thr Ser Leu
        515                 520                 525

Lys Tyr Glu Cys Arg Pro Glu Tyr Tyr Gly Arg Pro Phe Ser Ile Thr
530                 535                 540

Cys Leu Asp Asn Leu Val Trp Ser Ser Pro Lys Asp Val Cys Lys Arg
545                 550                 555                 560

Lys Ser Cys Lys Thr Pro Pro Asp Pro Val Asn Gly Met Val His Val
                565                 570                 575

Ile Thr Asp Ile Gln Val Gly Ser Arg Ile Asn Tyr Ser Cys Thr Thr
            580                 585                 590

Gly His Arg Leu Ile Gly His Ser Ser Ala Glu Cys Ile Leu Ser Gly
        595                 600                 605

Asn Ala Ala His Trp Ser Thr Lys Pro Pro Ile Cys Gln Arg Ile Pro
610                 615                 620

Cys Gly Leu Pro Pro Thr Ile Ala Asn Gly Asp Phe Ile Ser Thr Asn
625                 630                 635                 640

Arg Glu Asn Phe His Tyr Gly Ser Val Val Thr Tyr Arg Cys Asn Pro
                645                 650                 655

Gly Ser Gly Gly Arg Lys Val Phe Glu Leu Val Gly Glu Pro Ser Ile
            660                 665                 670

Tyr Cys Thr Ser Asn Asp Asp Gln Val Gly Ile Trp Ser Gly Pro Ala
        675                 680                 685

Pro Gln Cys Ile Ile Pro Asn Lys Cys Thr Pro Pro Asn Val Glu Asn
690                 695                 700

Gly Ile Leu Val Ser Asp Asn Arg Ser Leu Phe Ser Leu Asn Glu Val
705                 710                 715                 720

Val Glu Phe Arg Cys Gln Pro Gly Phe Val Met Lys Gly Pro Arg Arg
                725                 730                 735

Val Lys Cys Gln Ala Leu Asn Lys Trp Glu Pro Glu Leu Pro Ser Cys
            740                 745                 750

Ser Arg Val Cys Gln Pro Pro Pro Asp Val Leu His Ala Glu Arg Thr
        755                 760                 765

Gln Arg Asp Lys Asp Asn Phe Ser Pro Gly Gln Glu Val Phe Tyr Ser
770                 775                 780

Cys Glu Pro Gly Tyr Asp Leu Arg Gly Ala Ala Ser Met Arg Cys Thr
785                 790                 795                 800

Pro Gln Gly Asp Trp Ser Pro Ala Ala Pro Thr Cys Glu Val Lys Ser
                805                 810                 815

Cys Asp Asp Phe Met Gly Gln Leu Leu Asn Gly Arg Val Leu Phe Pro
            820                 825                 830
```

-continued

Val Asn Leu Gln Leu Gly Ala Lys Val Asp Phe Val Cys Asp Glu Gly
        835                 840                 845

Phe Gln Leu Lys Gly Ser Ser Ala Ser Tyr Cys Val Leu Ala Gly Met
850                 855                 860

Glu Ser Leu Trp Asn Ser Ser Val Pro Val Cys Glu Gln Ile Phe Cys
865                 870                 875                 880

Pro Ser Pro Pro Val Ile Pro Asn Gly Arg His Thr Gly Lys Pro Leu
                885                 890                 895

Glu Val Phe Pro Phe Gly Lys Ala Val Asn Tyr Thr Cys Asp Pro His
            900                 905                 910

Pro Asp Arg Gly Thr Ser Phe Asp Leu Ile Gly Glu Ser Thr Ile Arg
        915                 920                 925

Cys Thr Ser Asp Pro Gln Gly Asn Gly Val Trp Ser Ser Pro Ala Pro
930                 935                 940

Arg Cys Gly Ile Leu Gly His Cys Gln Ala Pro Asp His Phe Leu Phe
945                 950                 955                 960

Ala Lys Leu Lys Thr Gln Thr Asn Ala Ser Asp Phe Pro Ile Gly Thr
                965                 970                 975

Ser Leu Lys Tyr Glu Cys Arg Pro Glu Tyr Tyr Gly Arg Pro Phe Ser
            980                 985                 990

Ile Thr Cys Leu Asp Asn Leu Val Trp Ser Ser Pro Lys Asp Val Cys
        995                 1000                1005

Lys Arg Lys Ser Cys Lys Thr Pro Pro Asp Pro Val Asn Gly Met Val
        1010                1015                1020

His Val Ile Thr Asp Ile Gln Val Gly Ser Arg Ile Asn Tyr Ser Cys
1025                1030                1035                1040

Thr Thr Gly His Arg Leu Ile Gly His Ser Ser Ala Glu Cys Ile Leu
                1045                1050                1055

Ser Gly Asn Thr Ala His Trp Ser Thr Lys Pro Pro Ile Cys Gln Arg
            1060                1065                1070

Ile Pro Cys Gly Leu Pro Pro Thr Ile Ala Asn Gly Asp Phe Ile Ser
        1075                1080                1085

Thr Asn Arg Glu Asn Phe His Tyr Gly Ser Val Val Thr Tyr Arg Cys
        1090                1095                1100

Asn Leu Gly Ser Arg Gly Arg Lys Val Phe Glu Leu Val Gly Glu Pro
1105                1110                1115                1120

Ser Ile Tyr Cys Thr Ser Asn Asp Asp Gln Val Gly Ile Trp Ser Gly
                1125                1130                1135

Pro Ala Pro Gln Cys Ile Ile Pro Asn Lys Cys Thr Pro Pro Asn Val
            1140                1145                1150

Glu Asn Gly Ile Leu Val Ser Asp Asn Arg Ser Leu Phe Ser Leu Asn
        1155                1160                1165

Glu Val Val Glu Phe Arg Cys Gln Pro Gly Phe Val Met Lys Gly Pro
        1170                1175                1180

Arg Arg Val Lys Cys Gln Ala Leu Asn Lys Trp Glu Pro Glu Leu Pro
1185                1190                1195                1200

Ser Cys Ser Arg Val Cys Gln Pro Pro Glu Ile Leu His Gly Glu
                1205                1210                1215

His Thr Pro Ser His Gln Asp Asn Phe Ser Pro Gly Gln Glu Val Phe
            1220                1225                1230

Tyr Ser Cys Glu Pro Gly Tyr Asp Leu Arg Gly Ala Ala Ser Leu His
        1235                1240                1245

Cys Thr Pro Gln Gly Asp Trp Ser Pro Glu Ala Pro Arg Cys Ala Val
        1250                1255                1260

-continued

```
Lys Ser Cys Asp Asp Phe Leu Gly Gln Leu Pro His Gly Arg Val Leu
1265                1270                1275                1280

Phe Pro Leu Asn Leu Gln Leu Gly Ala Lys Val Ser Phe Val Cys Asp
            1285                1290                1295

Glu Gly Phe Arg Leu Lys Gly Ser Ser Val Ser His Cys Val Leu Val
        1300                1305                1310

Gly Met Arg Ser Leu Trp Asn Asn Ser Val Pro Val Cys Glu His Ile
    1315                1320                1325

Phe Cys Pro Asn Pro Pro Ala Ile Leu Asn Gly Arg His Thr Gly Thr
1330                1335                1340

Pro Ser Gly Asp Ile Pro Tyr Gly Lys Glu Ile Ser Tyr Thr Cys Asp
1345                1350                1355                1360

Pro His Pro Asp Arg Gly Met Thr Phe Asn Leu Ile Gly Glu Ser Thr
            1365                1370                1375

Ile Arg Cys Thr Ser Asp Pro His Gly Asn Gly Val Trp Ser Ser Pro
        1380                1385                1390

Ala Pro Arg Cys Glu Leu Ser Val Arg Ala Gly His Cys Lys Thr Pro
    1395                1400                1405

Glu Gln Phe Pro Phe Ala Ser Pro Thr Ile Pro Ile Asn Asp Phe Glu
    1410                1415                1420

Phe Pro Val Gly Thr Ser Leu Asn Tyr Glu Cys Arg Pro Gly Tyr Phe
1425                1430                1435                1440

Gly Lys Met Phe Ser Ile Ser Cys Leu Glu Asn Leu Val Trp Ser Ser
            1445                1450                1455

Val Glu Asp Asn Cys Arg Arg Lys Ser Cys Gly Pro Pro Pro Glu Pro
        1460                1465                1470

Phe Asn Gly Met Val His Ile Asn Thr Asp Thr Gln Phe Gly Ser Thr
    1475                1480                1485

Val Asn Tyr Ser Cys Asn Glu Gly Phe Arg Leu Ile Gly Ser Pro Ser
    1490                1495                1500

Thr Thr Cys Leu Val Ser Gly Asn Asn Val Thr Trp Asp Lys Lys Ala
1505                1510                1515                1520

Pro Ile Cys Glu Ile Ile Ser Cys Glu Pro Pro Pro Thr Ile Ser Asn
            1525                1530                1535

Gly Asp Phe Tyr Ser Asn Asn Arg Thr Ser Phe His Asn Gly Thr Val
        1540                1545                1550

Val Thr Tyr Gln Cys His Thr Gly Pro Asp Gly Glu Gln Leu Phe Glu
    1555                1560                1565

Leu Val Gly Glu Arg Ser Ile Tyr Cys Thr Ser Lys Asp Asp Gln Val
    1570                1575                1580

Gly Val Trp Ser Ser Pro Pro Pro Arg Cys Ile Ser Thr Asn Lys Cys
1585                1590                1595                1600

Thr Ala Pro Glu Val Glu Asn Ala Ile Arg Val Pro Gly Asn Arg Ser
            1605                1610                1615

Phe Phe Ser Leu Thr Glu Ile Ile Arg Phe Arg Cys Gln Pro Gly Phe
        1620                1625                1630

Val Met Val Gly Ser His Thr Val Gln Cys Gln Thr Asn Gly Arg Trp
    1635                1640                1645

Gly Pro Lys Leu Pro His Cys Ser Arg Val Cys Gln Pro Pro Pro Glu
    1650                1655                1660

Ile Leu His Gly Glu His Thr Leu Ser His Gln Asp Asn Phe Ser Pro
1665                1670                1675                1680

Gly Gln Glu Val Phe Tyr Ser Cys Glu Pro Ser Tyr Asp Leu Arg Gly
```

```
                    1685                1690                1695
Ala Ala Ser Leu His Cys Thr Pro Gln Gly Asp Trp Ser Pro Glu Ala
            1700                1705                1710

Pro Arg Cys Thr Val Lys Ser Cys Asp Asp Phe Leu Gly Gln Leu Pro
        1715                1720                1725

His Gly Arg Val Leu Leu Pro Leu Asn Leu Gln Leu Gly Ala Lys Val
    1730                1735                1740

Ser Phe Val Cys Asp Glu Gly Phe Arg Leu Lys Gly Arg Ser Ala Ser
1745                1750                1755                1760

His Cys Val Leu Ala Gly Met Lys Ala Leu Trp Asn Ser Ser Val Pro
            1765                1770                1775

Val Cys Glu Gln Ile Phe Cys Pro Asn Pro Pro Ala Ile Leu Asn Gly
        1780                1785                1790

Arg His Thr Gly Thr Pro Phe Gly Asp Ile Pro Tyr Gly Lys Glu Ile
    1795                1800                1805

Ser Tyr Ala Cys Asp Thr His Pro Asp Arg Gly Met Thr Phe Asn Leu
1810                1815                1820

Ile Gly Glu Ser Ser Ile Arg Cys Thr Ser Asp Pro Gln Gly Asn Gly
1825                1830                1835                1840

Val Trp Ser Ser Pro Ala Pro Arg Cys Glu Leu Ser Val Pro Ala Ala
            1845                1850                1855

Cys Pro His Pro Pro Lys Ile Gln Asn Gly His Tyr Ile Gly Gly His
        1860                1865                1870

Val Ser Leu Tyr Leu Pro Gly Met Thr Ile Ser Tyr Thr Cys Asp Pro
    1875                1880                1885

Gly Tyr Leu Leu Val Gly Lys Gly Phe Ile Phe Cys Thr Asp Gln Gly
    1890                1895                1900

Ile Trp Ser Gln Leu Asp His Tyr Cys Lys Glu Val Asn Cys Ser Phe
1905                1910                1915                1920

Pro Leu Phe Met Asn Gly Ile Ser Lys Glu Leu Glu Met Lys Lys Val
            1925                1930                1935

Tyr His Tyr Gly Asp Tyr Val Thr Leu Lys Cys Glu Asp Gly Tyr Thr
        1940                1945                1950

Leu Glu Gly Ser Pro Trp Ser Gln Cys Gln Ala Asp Asp Arg Trp Asp
    1955                1960                1965

Pro Pro Leu Ala Lys Cys Thr Ser Arg Ala His Asp Ala Leu Ile Val
    1970                1975                1980

Gly Thr Leu Ser Gly Thr Ile Phe Phe Ile Leu Leu Ile Ile Phe Leu
1985                1990                1995                2000

Ser Trp Ile Ile Leu Lys His Arg Lys Gly Asn Asn Ala His Glu Asn
            2005                2010                2015

Pro Lys Glu Val Ala Ile His Leu His Ser Gln Gly Gly Ser Ser Val
        2020                2025                2030

His Pro Arg Thr Leu Gln Thr Asn Glu Glu Asn Ser Arg Val Leu Pro
    2035                2040                2045

<210> SEQ ID NO 7
<211> LENGTH: 1029
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 7
tgtgaggagc caccaacatt tgaagctatg gagctcattg gtaaaccaaa accctactat     60
```

-continued

```
gagattggtg aacgagtaga ttataagtgt aaaaaaggat acttctatat acctcctctt    120
gccacccata ctatttgtga tcggaatcat acatggctac ctgtctcaga tgacgcctgt    180
tatagagaaa catgtccata tatacgggat cctttaaatg ccaagcagtt ccctgcaaat    240
gggacttacg agtttggtta tcagatgcac tttatttgta atgagggtta ttacttaatt    300
ggtgaagaaa ttctatattg tgaacttaaa ggatcagtag caatttggag cggtaagccc    360
ccaatatgtg aaaggttttt gtgtacacca cctccaaaaa taaaaaatgg aaaacacacc    420
tttagtgaag tagaagtatt tgagtatctt gatgcagtaa cttatagttg tgatcctgca    480
cctggaccag atccattttc acttattgga gagagcacga tttattgtgg tgacaattca    540
gtgtggagtc gtgctgctcc agagtgtaaa gtggtcaaat gtcgatttcc agtagtcgaa    600
aatggaaaac agatatcagg atttggaaaa aaatttttact acaaagcaac agttatgttt    660
gaatgcgata agggtttta cctcgatggc agcgacacaa ttgtctgtga cagtaacagt    720
acttgggatc ccccagttcc aaagtgtctt aaagtgtcga cttcttccac tacaaaatct    780
ccagcgtcca gtgcctcagg tcctaggcct acttacaagc ctccagtctc aaattatcca    840
ggatatccta aacctgagga aggaatactt gacagtttgg atgtttgggt cattgctgtg    900
attgttattg ccatagttgt tggagttgca gtaatttgtg ttgtcccgta cagatatctt    960
caaaggagga agaagaaagg cacataccta actgatgaga cccacagaga agtaaaattt   1020
acttctctc                                                             1029
```

<210> SEQ ID NO 8
<211> LENGTH: 376
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 8

```
Met Glu Pro Pro Gly Arg Arg Glu Cys Pro Phe Pro Ser Trp Arg Phe
 1               5                  10                  15

Phe Pro Gly Leu Leu Ala Ala Met Val Leu Leu Lys Phe Ser Asp
                20                  25                  30

Ala Cys Glu Glu Pro Pro Thr Phe Glu Ala Met Glu Leu Ile Gly Lys
            35                  40                  45

Pro Lys Pro Tyr Tyr Glu Ile Gly Glu Arg Val Asp Tyr Lys Cys Lys
        50                  55                  60

Lys Gly Tyr Phe Tyr Ile Pro Pro Leu Ala Thr His Thr Ile Cys Asp
 65                  70                  75                  80

Arg Asn His Thr Trp Leu Pro Val Ser Asp Asp Ala Cys Tyr Arg Glu
                85                  90                  95

Thr Cys Pro Tyr Ile Arg Asp Pro Leu Asn Gly Gln Ala Val Pro Ala
            100                 105                 110

Asn Gly Thr Tyr Glu Phe Gly Tyr Gln Met His Phe Ile Cys Asn Glu
        115                 120                 125

Gly Tyr Tyr Leu Ile Gly Glu Glu Ile Leu Tyr Cys Glu Leu Lys Gly
    130                 135                 140

Ser Val Ala Ile Trp Ser Gly Lys Pro Ile Cys Glu Lys Val Leu
145                 150                 155                 160

Cys Thr Pro Pro Pro Lys Ile Lys Asn Gly Lys His Thr Phe Ser Glu
                165                 170                 175

Val Glu Val Phe Glu Tyr Leu Asp Ala Val Thr Tyr Ser Cys Asp Pro
```

```
                    180                 185                 190
Ala Pro Gly Pro Asp Pro Phe Ser Leu Ile Gly Glu Ser Thr Ile Tyr
            195                 200                 205

Cys Gly Asp Asn Ser Val Trp Ser Arg Ala Ala Pro Glu Cys Lys Val
        210                 215                 220

Val Lys Cys Arg Phe Pro Val Val Glu Asn Gly Lys Gln Ile Ser Gly
225                 230                 235                 240

Phe Gly Lys Lys Phe Tyr Tyr Lys Ala Thr Val Met Phe Glu Cys Asp
                245                 250                 255

Lys Gly Phe Tyr Leu Asp Gly Ser Asp Thr Ile Val Cys Asp Ser Asn
            260                 265                 270

Ser Thr Trp Asp Pro Pro Val Pro Lys Cys Leu Lys Val Ser Thr Ser
        275                 280                 285

Ser Thr Thr Lys Ser Pro Ala Ser Ser Ala Ser Gly Pro Arg Pro Thr
290                 295                 300

Tyr Lys Pro Pro Val Ser Asn Tyr Pro Gly Tyr Pro Lys Pro Glu Glu
305                 310                 315                 320

Gly Ile Leu Asp Ser Leu Asp Val Trp Val Ile Ala Val Ile Val Ile
                325                 330                 335

Ala Ile Val Val Gly Val Ala Val Ile Cys Val Val Pro Tyr Arg Tyr
            340                 345                 350

Leu Gln Arg Arg Lys Lys Lys Gly Thr Tyr Leu Thr Asp Glu Thr His
        355                 360                 365

Arg Glu Val Lys Phe Thr Ser Leu
        370                 375

<210> SEQ ID NO 9
<211> LENGTH: 436
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 9

Met Glu Val Ser Ser Arg Ser Ser Glu Pro Leu Asp Pro Val Trp Leu
1               5                   10                  15

Leu Val Ala Phe Gly Arg Gly Val Lys Leu Glu Val Leu Leu Leu
            20                  25                  30

Phe Leu Leu Pro Phe Thr Leu Gly His Cys Pro Ala Pro Ser Gln Leu
        35                  40                  45

Pro Ser Ala Lys Pro Ile Asn Leu Thr Asp Glu Ser Met Phe Pro Ile
50                  55                  60

Gly Thr Tyr Leu Leu Tyr Glu Cys Leu Pro Gly Tyr Ile Lys Arg Gln
65                  70                  75                  80

Phe Ser Ile Thr Cys Lys Gln Asp Ser Thr Trp Thr Ser Ala Glu Asp
                85                  90                  95

Lys Cys Ile Arg Lys Gln Cys Lys Thr Pro Ser Asp Pro Glu Asn Gly
            100                 105                 110

Leu Val His Val His Thr Gly Ile Gln Phe Gly Ser Arg Ile Asn Tyr
        115                 120                 125

Thr Cys Asn Gln Gly Tyr Arg Leu Ile Gly Ser Ser Ala Val Cys
        130                 135                 140

Val Ile Thr Asp Gln Ser Val Asp Trp Asp Thr Glu Ala Pro Ile Cys
145                 150                 155                 160

Glu Trp Ile Pro Cys Glu Ile Pro Pro Gly Ile Pro Asn Gly Asp Phe
```

```
                     165                 170                 175
Phe Ser Ser Thr Arg Glu Asp Phe His Tyr Gly Met Val Val Tyr Cys
                180                 185                 190
Asn Thr Asp Arg Lys Ala Leu Phe Asn Leu Val Gly Glu Pro Ser Leu
            195                 200                 205
Tyr Cys Thr Ser Asn Asp Gly Glu Ile Gly Val Trp Ser Gly Pro Pro
        210                 215                 220
Pro Gln Cys Ile Glu Leu Asn Lys Cys Thr Pro Pro Tyr Val Glu
225                 230                 235                 240
Asn Ala Val Met Leu Ser Glu Asn Arg Ser Leu Phe Ser Leu Arg Asp
                245                 250                 255
Ile Val Glu Phe Arg Cys His Pro Gly Phe Ile Met Lys Gly Ala Ser
                260                 265                 270
Ser Val His Cys Gln Ser Leu Asn Lys Trp Glu Pro Glu Leu Pro Ser
            275                 280                 285
Cys Phe Lys Gly Val Ile Cys Arg Leu Pro Gln Glu Met Ser Gly Phe
        290                 295                 300
Gln Lys Gly Leu Gly Met Lys Lys Glu Tyr Tyr Tyr Gly Glu Asn Val
305                 310                 315                 320
Thr Leu Glu Cys Glu Asp Gly Tyr Thr Leu Glu Gly Ser Ser Gln Ser
                325                 330                 335
Gln Cys Gln Ser Asp Gly Ser Trp Asn Pro Leu Leu Ala Lys Cys Val
                340                 345                 350
Ser Arg Ser Ile Ser Gly Leu Ile Val Gly Ile Phe Ile Gly Ile Ile
            355                 360                 365
Val Phe Ile Leu Val Ile Ile Val Phe Ile Trp Met Ile Leu Lys Tyr
        370                 375                 380
Lys Lys Arg Asn Thr Thr Asp Glu Lys Tyr Lys Glu Val Gly Ile His
385                 390                 395                 400
Leu Asn Tyr Lys Glu Asp Ser Cys Val Arg Leu Gln Ser Leu Leu Thr
                405                 410                 415
Ser Gln Glu Asn Ser Ser Thr Thr Ser Pro Ala Arg Asn Ser Leu Thr
                420                 425                 430
Gln Glu Val Ser
        435

<210> SEQ ID NO 10
<211> LENGTH: 293
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 10

Met Gly Phe Lys Met Glu Ser His Ser Gln Val Leu Met Leu Leu Leu
1               5                   10                  15
Leu Trp Val Ser Gly Thr Cys Gly Asp Ile Val Met Ser Gln Ser Pro
            20                  25                  30
Ser Ser Leu Ala Val Ser Val Gly Glu Lys Val Thr Met Asn Cys Lys
        35                  40                  45
Ser Ser Gln Ser Leu Lys Thr Asn Gln Lys Asn Tyr Leu Ala Trp Tyr
    50                  55                  60
Gln Gln Lys Pro Gly Gln Ser Pro Lys Leu Leu Ile Tyr Trp Ala Ser
65                  70                  75                  80

Ser Arg Glu Ser Gly Val Pro Asp Arg Phe Thr Gly Ser Gly Ser Gly
```

```
                        85                  90                  95
Thr Asp Phe Thr Leu Thr Ile Ser Ser Val Lys Ala Glu Asp Leu Ala
                100                 105                 110
Val Tyr Tyr Cys Gln Gln Tyr Tyr Ser Tyr Pro Leu Thr Phe Gly Ala
                115                 120                 125
Gly Thr Lys Leu Glu Leu Lys Gly Gly Gly Ser Gly Gly Gly
            130                 135                 140
Ser Gly Gly Gly Gly Ser Met Gly Trp Ser Cys Val Met Leu Phe Leu
145                 150                 155                 160
Val Ala Thr Ala Thr Gly Val His Ser Gln Val Gln Leu Glu Gln Ser
                165                 170                 175
Gly Pro Glu Leu Val Arg Pro Gly Val Ser Val Lys Ile Ser Cys Lys
                180                 185                 190
Gly Ser Gly Tyr Thr Phe Thr Asp Tyr Ala Ile His Trp Val Lys Gln
                195                 200                 205
Ser His Ala Lys Ser Leu Glu Trp Ile Gly Val Ile Ser Thr Tyr Tyr
                210                 215                 220
Gly His Thr His Tyr Asn Gln Lys Phe Lys Gly Lys Ala Thr Leu Thr
225                 230                 235                 240
Val Asp Lys Ser Ser Asn Thr Ala Tyr Met Glu Leu Ala Arg Leu Thr
                245                 250                 255
Ser Glu Asp Ser Ala Ile Tyr Tyr Cys Ala Arg Pro Asn Asn Tyr Gly
                260                 265                 270
Ser Ser Pro Pro Tyr Tyr Ala Met Asp Cys Trp Gly Gln Gly Thr Ser
                275                 280                 285
Val Thr Val Ser Ser
        290

<210> SEQ ID NO 11
<211> LENGTH: 824
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 11

Met Gly Phe Lys Met Glu Ser His Ser Gln Val Leu Met Leu Leu Leu
1               5                   10                  15
Leu Trp Val Ser Gly Thr Cys Gly Asp Ile Val Met Ser Gln Ser Pro
                20                  25                  30
Ser Ser Leu Ala Val Ser Val Gly Glu Lys Val Thr Met Asn Cys Lys
            35                  40                  45
Ser Ser Gln Ser Leu Lys Thr Asn Gln Lys Asn Tyr Leu Ala Trp Tyr
        50                  55                  60
Gln Gln Lys Pro Gly Gln Ser Pro Lys Leu Leu Ile Tyr Trp Ala Ser
65                  70                  75                  80
Ser Arg Glu Ser Gly Val Pro Asp Arg Phe Thr Gly Ser Gly Ser Gly
                85                  90                  95
Thr Asp Phe Thr Leu Thr Ile Ser Ser Val Lys Ala Glu Asp Leu Ala
                100                 105                 110
Val Tyr Tyr Cys Gln Gln Tyr Tyr Ser Tyr Pro Leu Thr Phe Gly Ala
                115                 120                 125
Gly Thr Lys Leu Glu Leu Lys Gly Gly Gly Ser Gly Gly Gly Gly
            130                 135                 140
Ser Gly Gly Gly Gly Ser Met Gly Trp Ser Cys Val Met Leu Phe Leu
```

```
                145                 150                 155                 160
Val Ala Thr Ala Thr Gly Val His Ser Gln Val Gln Leu Glu Gln Ser
                    165                 170                 175

Gly Pro Glu Leu Val Arg Pro Gly Val Ser Val Lys Ile Ser Cys Lys
            180                 185                 190

Gly Ser Gly Tyr Thr Phe Thr Asp Tyr Ala Ile His Trp Val Lys Gln
        195                 200                 205

Ser His Ala Lys Ser Leu Glu Trp Ile Gly Val Ile Ser Thr Tyr Tyr
    210                 215                 220

Gly His Thr His Tyr Asn Gln Lys Phe Lys Gly Lys Ala Thr Leu Thr
225                 230                 235                 240

Val Asp Lys Ser Ser Asn Thr Ala Tyr Met Glu Leu Ala Arg Leu Thr
                245                 250                 255

Ser Glu Asp Ser Ala Ile Tyr Tyr Cys Ala Arg Pro Asn Asn Tyr Gly
            260                 265                 270

Ser Ser Pro Pro Tyr Tyr Ala Met Asp Cys Trp Gly Gln Gly Thr Ser
        275                 280                 285

Val Thr Val Ser Ser Gly Gly Gly Gly Ser Gly Gly Gly Gly Ser Gly
    290                 295                 300

Gly Gly Gly Ser Cys Pro Ala Pro Pro Leu Phe Pro Tyr Ala Lys Pro
305                 310                 315                 320

Ile Asn Pro Thr Asp Glu Ser Thr Phe Pro Val Gly Thr Ser Leu Lys
                325                 330                 335

Tyr Glu Cys Arg Pro Gly Tyr Ile Lys Arg Gln Phe Ser Ile Thr Cys
            340                 345                 350

Glu Val Asn Ser Val Trp Thr Ser Pro Gln Asp Val Cys Ile Arg Lys
        355                 360                 365

Gln Cys Glu Thr Pro Leu Asp Pro Gln Asn Gly Ile Val His Val Asn
    370                 375                 380

Thr Asp Ile Arg Phe Gly Ser Ser Ile Thr Tyr Thr Cys Asn Glu Gly
385                 390                 395                 400

Tyr Arg Leu Ile Gly Ser Ser Ala Met Cys Ile Ile Ser Asp Gln
                405                 410                 415

Ser Val Ala Trp Asp Ala Glu Ala Pro Ile Cys Glu Ser Ile Pro Cys
            420                 425                 430

Glu Ile Pro Pro Ser Ile Pro Asn Gly Asp Phe Phe Ser Pro Asn Arg
        435                 440                 445

Glu Asp Phe His Tyr Gly Met Val Val Thr Tyr Gln Cys Asn Thr Asp
    450                 455                 460

Arg Lys Lys Leu Phe Asn Leu Val Gly Glu Pro Ser Ile His Cys Thr
465                 470                 475                 480

Ser Ile Asp Gly Gln Val Gly Val Trp Ser Gly Pro Pro Gln Cys
                485                 490                 495

Ile Glu Leu Asn Lys Cys Thr Pro Pro His Val Glu Asn Ala Val Ile
            500                 505                 510

Val Ser Lys Asn Lys Ser Leu Phe Ser Leu Arg Asp Met Val Glu Phe
        515                 520                 525

Arg Cys Gln Asp Gly Phe Met Met Lys Gly Asp Ser Ser Val Tyr Cys
    530                 535                 540

Arg Ser Leu Asn Arg Trp Glu Pro Gln Leu Pro Ser Cys Phe Lys Val
545                 550                 555                 560

Lys Ser Cys Gly Ala Phe Leu Gly Glu Leu Pro Asn Gly His Val Phe
                565                 570                 575
```

-continued

Val Pro Gln Asn Leu Gln Leu Gly Ala Lys Val Thr Phe Val Cys Asn
            580                 585                 590

Thr Gly Tyr Gln Leu Lys Gly Asn Ser Ser His Cys Val Leu Asp
    595                 600                 605

Gly Val Glu Ser Ile Trp Asn Ser Ser Val Pro Val Cys Glu Gln Val
    610                 615                 620

Ile Cys Lys Leu Pro Gln Asp Met Ser Gly Phe Gln Lys Gly Leu Gln
625                 630                 635                 640

Met Lys Lys Asp Tyr Tyr Gly Asp Asn Val Glu Cys Glu Asp Gly
                645                 650                 655

Tyr Thr Leu Glu Gly Ser Ser Ser Gln Cys Gln Ser Asp Ala Ser
            660                 665                 670

Trp Asp Pro Pro Leu Pro Lys Cys Val Ser Gln Val Ile Cys Lys Leu
            675                 680                 685

Pro Gln Asp Met Ser Gly Phe Gln Lys Gly Leu Gln Met Lys Lys Asp
            690                 695                 700

Tyr Tyr Tyr Gly Asp Asn Val Glu Cys Glu Asp Gly Tyr Thr Leu Glu
705                 710                 715                 720

Gly Ser Ser Gln Ser Gln Cys Gln Ser Asp Ala Ser Trp Asp Pro Pro
                725                 730                 735

Leu Pro Lys Cys Val Ser Arg Ser Asn Ser Gly Leu Ile Ala Gly Ile
            740                 745                 750

Phe Ile Gly Ile Ile Val Leu Ile Leu Phe Ile Ile Phe Ser Tyr Trp
            755                 760                 765

Met Ile Met Lys Phe Lys Lys Arg Asn Ser Thr Asn Glu Lys Cys Lys
            770                 775                 780

Glu Val Gly Ile Tyr Leu Asn Ser Lys Glu Asp Ser Cys Val Gln Pro
785                 790                 795                 800

Gln Ser Leu Leu Thr Ser Gln Glu Asn Asn Ser Thr Ser Ser Pro Ala
                805                 810                 815

Arg Asn Ser Leu Thr Gln Glu Val
            820

<210> SEQ ID NO 12
<211> LENGTH: 412
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 12

Met Gly Phe Lys Met Glu Ser His Ser Gln Val Leu Met Leu Leu Leu
1               5                   10                  15

Leu Trp Val Ser Gly Thr Cys Gly Asp Ile Val Met Ser Gln Ser Pro
            20                  25                  30

Ser Ser Leu Ala Val Ser Val Gly Glu Lys Val Thr Met Asn Cys Lys
        35                  40                  45

Ser Ser Gln Ser Leu Lys Thr Asn Gln Lys Asn Tyr Leu Ala Trp Tyr
    50                  55                  60

Gln Gln Lys Pro Gly Gln Ser Pro Lys Leu Leu Ile Tyr Trp Ala Ser
65                  70                  75                  80

Ser Arg Glu Ser Gly Val Pro Asp Arg Phe Thr Gly Ser Gly Ser Gly
                85                  90                  95

Thr Asp Phe Thr Leu Thr Ile Ser Ser Val Lys Ala Glu Asp Leu Ala
            100                 105                 110

```
Val Tyr Tyr Cys Gln Gln Tyr Ser Tyr Pro Leu Thr Phe Gly Ala
        115                 120                 125
Gly Thr Lys Leu Glu Leu Lys Gly Gly Gly Ser Gly Gly Gly Gly
130                 135                 140
Ser Gly Gly Gly Gly Ser Met Gly Trp Ser Cys Val Met Leu Phe Leu
145                 150                 155                 160
Val Ala Thr Ala Thr Gly Val His Ser Gln Val Gln Leu Gln Ser
        165                 170                 175
Gly Pro Glu Leu Val Arg Pro Gly Val Ser Val Lys Ile Ser Cys Lys
        180                 185                 190
Gly Ser Gly Tyr Thr Phe Thr Asp Tyr Ala Ile His Trp Val Lys Gln
        195                 200                 205
Ser His Ala Lys Ser Leu Glu Trp Ile Gly Val Ile Ser Thr Tyr Tyr
        210                 215                 220
Gly His Thr His Tyr Asn Gln Lys Phe Lys Gly Lys Ala Thr Leu Thr
225                 230                 235                 240
Val Asp Lys Ser Ser Asn Thr Ala Tyr Met Glu Leu Ala Arg Leu Thr
                245                 250                 255
Ser Glu Asp Ser Ala Ile Tyr Tyr Cys Ala Arg Pro Asn Asn Tyr Gly
        260                 265                 270
Ser Ser Pro Pro Tyr Tyr Ala Met Asp Cys Trp Gly Gln Gly Thr Ser
        275                 280                 285
Val Thr Val Ser Ser Gly Gly Gly Gly Ser Gly Gly Gly Gly Ser Gly
        290                 295                 300
Gly Gly Gly Ser Leu Arg Cys Tyr Asn Cys Leu Asp Pro Val Ser Ser
305                 310                 315                 320
Cys Lys Thr Asn Ser Thr Cys Ser Pro Asn Leu Asp Ala Cys Leu Val
                325                 330                 335
Ala Val Ser Gly Lys Gln Val Tyr Gln Gln Cys Trp Arg Phe Ser Asp
                340                 345                 350
Cys Asn Ala Lys Phe Ile Leu Ser Arg Leu Glu Ile Ala Asn Val Gln
                355                 360                 365
Tyr Arg Cys Cys Gln Ala Asp Leu Cys Asn Lys Ser Phe Glu Asp Lys
        370                 375                 380
Pro Asn Asn Gly Ala Ile Ser Leu Leu Gly Lys Thr Ala Leu Leu Val
385                 390                 395                 400
Thr Ser Val Leu Ala Ala Ile Leu Lys Pro Cys Phe
                405                 410

<210> SEQ ID NO 13
<211> LENGTH: 762
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 13

Met Lys Thr Pro Trp Lys Val Leu Leu Gly Leu Leu Gly Ala Ala Ala
1               5                   10                  15
Leu Val Thr Ile Ile Thr Val Pro Val Val Leu Leu Asn Lys Gly Thr
                20                  25                  30
Asp Asp Ala Thr Ala Asp Ser Arg Lys Thr Tyr Thr Leu Thr Asp Tyr
            35                  40                  45
Leu Lys Asn Tyr Leu Lys Lys Leu Arg Trp Ile Ser Asp His Glu Tyr
        50                  55                  60
```

```
Leu Tyr Lys Gln Glu Asn Asn Ile Leu Val Phe Asn Ala Glu Tyr Gly
 65                  70                  75                  80

Asn Ser Ser Val Phe Leu Glu Asn Ser Thr Phe Asp Glu Phe Gly His
                 85                  90                  95

Ser Ile Asn Asp Tyr Ser Ile Ser Pro Asp Gly Gln Phe Ile Leu Leu
            100                 105                 110

Glu Tyr Asn Tyr Val Lys Gln Trp Arg His Ser Tyr Thr Ala Ser Tyr
        115                 120                 125

Asp Ile Tyr Asp Leu Asn Lys Arg Gln Leu Ile Thr Glu Glu Arg Ile
130                 135                 140

Pro Asn Asn Thr Gln Trp Val Thr Trp Ser Pro Val Gly His Lys Leu
145                 150                 155                 160

Ala Tyr Val Trp Asn Asn Asp Ile Tyr Val Lys Ile Glu Pro Asn Leu
                165                 170                 175

Pro Ser Tyr Arg Ile Thr Trp Thr Gly Lys Glu Asp Ile Ile Tyr Asn
            180                 185                 190

Gly Ile Thr Asp Trp Val Tyr Glu Glu Val Phe Ser Ala Tyr Ser
        195                 200                 205

Ala Leu Trp Trp Ser Pro Asn Gly Thr Phe Leu Ala Tyr Ala Gln Phe
210                 215                 220

Asn Asp Thr Glu Val Pro Leu Ile Glu Tyr Ser Phe Tyr Ser Asp Glu
225                 230                 235                 240

Ser Leu Gln Tyr Pro Lys Thr Val Arg Val Pro Tyr Pro Lys Ala Gly
                245                 250                 255

Ala Val Asn Pro Thr Val Lys Phe Phe Val Val Asn Thr Asp Ser Leu
            260                 265                 270

Ser Ser Val Thr Asn Ala Thr Ser Ile Gln Ile Thr Ala Pro Ala Ser
        275                 280                 285

Met Leu Ile Gly Asp His Tyr Leu Cys Asp Val Thr Trp Ala Thr Gln
290                 295                 300

Glu Arg Ile Ser Leu Gln Trp Leu Arg Arg Ile Gln Asn Tyr Ser Val
305                 310                 315                 320

Met Asp Ile Cys Asp Tyr Asp Glu Ser Ser Gly Arg Trp Asn Cys Leu
                325                 330                 335

Val Ala Arg Gln His Ile Glu Met Ser Thr Thr Gly Trp Val Gly Arg
            340                 345                 350

Phe Arg Pro Ser Glu Pro His Phe Thr Leu Asp Gly Asn Ser Phe Tyr
        355                 360                 365

Lys Ile Ile Ser Asn Glu Glu Gly Tyr Arg His Ile Cys Tyr Phe Gln
370                 375                 380

Ile Asp Lys Lys Asp Cys Thr Phe Ile Thr Lys Gly Thr Trp Glu Val
385                 390                 395                 400

Ile Gly Ile Glu Ala Leu Thr Ser Asp Tyr Leu Tyr Tyr Ile Ser Asn
                405                 410                 415

Glu Tyr Lys Gly Met Pro Gly Gly Arg Asn Leu Tyr Lys Ile Gln Leu
            420                 425                 430

Ser Asp Tyr Thr Lys Val Thr Cys Leu Ser Cys Glu Leu Asn Pro Glu
        435                 440                 445

Arg Cys Gln Tyr Tyr Ser Val Ser Phe Ser Lys Glu Ala Lys Tyr Tyr
450                 455                 460

Gln Leu Arg Cys Ser Gly Pro Gly Leu Pro Leu Tyr Thr Leu His Ser
465                 470                 475                 480

Ser Val Asn Asp Lys Gly Leu Arg Val Leu Glu Asp Asn Ser Ala Leu
                485                 490                 495
```

```
Asp Lys Met Leu Gln Asn Val Gln Met Pro Ser Lys Lys Leu Asp Phe
            500                 505                 510

Ile Ile Leu Asn Glu Thr Lys Phe Trp Tyr Gln Met Ile Leu Pro Pro
            515                 520                 525

His Phe Asp Lys Ser Lys Lys Tyr Pro Leu Leu Asp Val Tyr Ala
            530                 535                 540

Gly Pro Cys Ser Gln Lys Ala Asp Thr Val Phe Arg Leu Asn Trp Ala
545                 550                 555                 560

Thr Tyr Leu Ala Ser Thr Glu Asn Ile Ile Val Ala Ser Phe Asp Gly
            565                 570                 575

Arg Gly Ser Gly Tyr Gln Gly Asp Lys Ile Met His Ala Ile Asn Arg
            580                 585                 590

Arg Leu Gly Thr Phe Glu Val Glu Asp Gln Ile Glu Ala Ala Arg Gln
            595                 600                 605

Phe Ser Lys Met Gly Phe Val Asp Asn Lys Arg Ile Ala Ile Trp Gly
            610                 615                 620

Trp Ser Tyr Gly Gly Tyr Val Thr Ser Met Val Leu Gly Ser Gly Ser
625                 630                 635                 640

Gly Val Phe Lys Cys Gly Ile Ala Val Ala Pro Val Ser Arg Trp Glu
            645                 650                 655

Tyr Tyr Asp Ser Val Tyr Thr Glu Arg Tyr Met Gly Leu Pro Thr Pro
            660                 665                 670

Glu Asp Asn Leu Asp His Tyr Arg Asn Ser Thr Val Met Ser Arg Ala
            675                 680                 685

Glu Asn Phe Lys Gln Val Glu Tyr Leu Leu Ile His Gly Thr Ala Asp
            690                 695                 700

Asp Asn Val His Phe Gln Gln Ser Ala Gln Ile Ser Lys Ala Leu Val
705                 710                 715                 720

Asp Val Gly Val Asp Phe Gln Ala Met Trp Tyr Thr Asp Glu Asp His
                    725                 730                 735

Gly Ile Ala Ser Ser Thr Ala His Gln His Ile Tyr Thr His Met Ser
            740                 745                 750

His Phe Ile Lys Gln Cys Phe Ser Leu Pro
            755                 760
```

<210> SEQ ID NO 14
<211> LENGTH: 481
<212> TYPE: PRT
<213> ORGANISM: Artificial Sequence
<220> FEATURE:
<223> OTHER INFORMATION: Description of Artificial Sequence;
    note=synthetic construct

<400> SEQUENCE: 14

```
Met Gly Cys Leu Trp Gly Leu Ala Leu Pro Leu Phe Phe Phe Cys Trp
1               5                   10                  15

Glu Val Gly Val Ser Gly Ser Ser Ala Gly Pro Ser Thr Arg Arg Ala
                20                  25                  30

Asp Thr Ala Met Thr Thr Asp Asp Thr Glu Val Pro Ala Met Thr Leu
            35                  40                  45

Ala Pro Gly His Ala Ala Leu Glu Thr Gln Thr Leu Ser Ala Glu Thr
        50                  55                  60

Ser Ser Arg Ala Ser Thr Pro Ala Gly Pro Ile Pro Glu Ala Glu Thr
65                  70                  75                  80

Arg Gly Ala Lys Arg Ile Ser Pro Ala Arg Glu Thr Arg Ser Phe Thr
                85                  90                  95
```

Lys Thr Ser Pro Asn Phe Met Val Leu Ile Ala Thr Ser Val Glu Thr
                100                 105                 110

Ser Ala Ala Ser Gly Ser Pro Glu Gly Ala Gly Met Thr Thr Val Gln
            115                 120                 125

Thr Ile Thr Gly Ser Asp Pro Glu Glu Ala Ile Phe Asp Thr Leu Cys
        130                 135                 140

Thr Asp Asp Ser Ser Glu Glu Ala Lys Thr Leu Thr Met Asp Ile Leu
145                 150                 155                 160

Thr Leu Ala His Thr Ser Thr Glu Ala Lys Gly Leu Ser Ser Glu Ser
                165                 170                 175

Ser Ala Ser Ser Asp Gly Pro His Pro Val Ile Thr Pro Ser Arg Ala
            180                 185                 190

Ser Glu Ser Ser Ala Ser Ser Asp Gly Pro His Pro Val Ile Thr Pro
        195                 200                 205

Ser Arg Ala Ser Glu Ser Ser Ala Ser Ser Asp Gly Pro His Pro Val
210                 215                 220

Ile Thr Pro Ser Trp Ser Pro Gly Ser Asp Val Leu Ala Glu Ala Leu
225                 230                 235                 240

Val Thr Val Thr Asn Ile Glu Val Ile Asn Cys Ser Ile Thr Glu Ile
                245                 250                 255

Glu Thr Thr Thr Ser Ser Ile Pro Gly Ala Ser Asp Ile Asp Leu Ile
            260                 265                 270

Pro Thr Glu Gly Val Lys Ala Ser Ser Thr Ser Asp Pro Pro Ala Leu
        275                 280                 285

Pro Asp Ser Thr Glu Ala Lys Pro His Ile Thr Glu Val Thr Ala Ser
290                 295                 300

Ala Glu Thr Leu Ser Ser Ala Leu Ser Val Glu Thr Pro Ser Tyr Val
305                 310                 315                 320

Lys Val Ser Gly Ala Ala Pro Val Ser Ile Glu Ala Gly Ser Ala Val
                325                 330                 335

Gly Lys Thr Thr Ser Phe Ala Gly Ser Ser Ala Ser Ser Tyr Ser Pro
            340                 345                 350

Ser Glu Ala Ala Leu Lys Asn Phe Thr Pro Ser Glu Thr Pro Thr Met
        355                 360                 365

Asp Ile Ala Thr Lys Gly Pro Phe Pro Thr Ser Arg Asp Pro Leu Pro
370                 375                 380

Ser Val Pro Pro Thr Thr Thr Asn Ser Ser Arg Gly Thr Asn Ser Thr
385                 390                 395                 400

Leu Ala Lys Ile Thr Thr Ser Ala Lys Thr Thr Met Lys Pro Pro Thr
                405                 410                 415

Ala Thr Pro Thr Thr Ala Arg Trp Thr Thr Asp Val Ser Ala Gly Glu
            420                 425                 430

Asn Gly Gly Phe Leu Leu Leu Arg Leu Ser Val Asp Glu Asp Leu Thr
        435                 440                 445

Asp Pro Arg Val Ala Glu Arg Leu Met Gln Gln Leu His Arg Glu Leu
450                 455                 460

His Ala His Ala Pro His Phe Gln Val Ser Leu Leu Arg Val Arg Arg
465                 470                 475                 480

Gly

<210> SEQ ID NO 15
<211> LENGTH: 359
<212> TYPE: PRT
<213> ORGANISM: Artificial Sequence -continued

```
<220> FEATURE:
<223> OTHER INFORMATION: Description of Artificial Sequence;
      note=synthetic construct

<400> SEQUENCE: 15

Met His Pro Gln Val Val Ile Leu Ser Leu Ile Leu His Leu Ala Asp
1               5                   10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
    50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
        115                 120                 125

Val Thr Thr Thr Pro Ile Val Thr Thr Val Pro Thr Val Thr Thr Val
130                 135                 140

Arg Thr Ser Thr Thr Val Pro Thr Thr Thr Val Pro Thr Thr Thr Thr
145                 150                 155                 160

Val Pro Thr Thr Met Ser Ile Pro Thr Thr Thr Val Pro Thr Thr Thr
                165                 170                 175

Met Thr Val Ser Thr Thr Thr Ser Val Pro Thr Thr Thr Ser Ile Pro
            180                 185                 190

Thr Thr Thr Ser Val Pro Val Thr Thr Val Ser Thr Phe Val Pro
        195                 200                 205

Pro Met Pro Leu Pro Arg Gln Asn His Glu Pro Val Ala Thr Ser Pro
    210                 215                 220

Ser Ser Pro Gln Pro Ala Glu Thr His Pro Thr Thr Leu Gln Gly Ala
225                 230                 235                 240

Ile Arg Arg Glu Pro Thr Ser Ser Pro Leu Tyr Ser Tyr Thr Thr Asp
                245                 250                 255

Gly Asn Asp Thr Val Thr Glu Ser Ser Asp Gly Leu Trp Asn Asn Asn
            260                 265                 270

Gln Thr Gln Leu Phe Leu Glu His Ser Leu Leu Thr Ala Asn Thr Thr
        275                 280                 285

Lys Gly Ile Tyr Ala Gly Val Cys Ile Ser Val Leu Val Leu Leu Ala
    290                 295                 300

Leu Leu Gly Val Ile Ile Ala Lys Lys Tyr Phe Phe Lys Lys Glu Val
305                 310                 315                 320

Gln Gln Leu Ser Val Ser Phe Ser Ser Leu Gln Ile Lys Ala Leu Gln
                325                 330                 335

Asn Ala Val Glu Lys Glu Val Gln Ala Glu Asp Asn Ile Tyr Ile Glu
            340                 345                 350

Asn Ser Leu Tyr Ala Thr Asp
        355

<210> SEQ ID NO 16
<211> LENGTH: 30
<212> TYPE: DNA
<213> ORGANISM: Artificial Sequence
```

```
<220> FEATURE:
<223> OTHER INFORMATION: Description of Artificial Sequence;
      note=synthetic construct

<400> SEQUENCE: 16
atgaagttgc ctgttaggct gttggtgctg                                          30

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 17
actggatggt gggaagatgg                                                     20

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 18
atgaaatgca gctggggcat gttcttc                                             27

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 19
cagtggatag accgatgggc c                                                   21

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 20

Ser Asp Cys Ile Lys Ser Ala Ala Arg Leu Ile Gln Asn
 1               5                  10

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 21

Phe Glu Val Glu Asp Gln Ile Glu Ala Ala Arg Gln Phe Ser
 1               5                  10

<210> SEQ ID NO 22
<211> LENGTH: 12
```

```
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 22

Phe Phe Lys Tyr Ala Cys Gly Gly Trp Leu Lys Arg
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 23

Tyr Gly Gly Tyr Val Thr Ser Met Val Leu
1               5                   10

<210> SEQ ID NO 24
<211> LENGTH: 22
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 24

Ser Lys His Val Val Glu Asp Leu Ile Ala Gln Ile Arg Glu Val Phe
1               5                   10                  15

Ile Gln Thr Leu Asp Asp
            20

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 25

Phe Gln Gln Ser Ala Gln Ile Ser Lys Ala Leu Val Asp Val
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 26

Ala Glu Thr Lys Lys Arg Ala Glu Glu Lys Ala
1               5                   10

<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence;
      note=synthetic construct
```

```
-continued

<400> SEQUENCE: 27

Ser Thr Ala His Gln His Ile Tyr Thr His Met Ser His Phe Ile Lys
1               5                   10                  15

Gln Cys Phe
```

TISSUE TARGETED COMPLEMENT MODULATORS

This application is a continuation-in-part of U.S. application Ser. No. 10/534,772, which is a national stage application of International Application No. PCT/US03/36459, filed Nov. 13, 2003, which is incorporated by reference herein in its entirety. This application also claims benefit of U.S. Provisional Application No. 60/565,907, filed Apr. 28, 2004, which is incorporated herein by reference in its entirety.

This invention was made with government support under National Institutes of Health Grants AI34451 and DK41873. The government has certain rights in the invention.

I. BACKGROUND OF THE INVENTION

Complement is the collective term for a series of blood proteins and is a major effector mechanism of the immune system. Complement activation and its deposition on target structures can lead to direct complement-mediated cell lysis, or can lead indirectly to cell or tissue destruction due to the generation of powerful modulators of inflammation and the recruitment and activation of immune effector cells. Complement activation products that mediate tissue injury are generated at various points in the complement pathway. Inappropriate complement activation on host tissue plays an important role in the pathology of many autoimmune and inflammatory diseases, and is also responsible for many disease states associated with bioincompatibility, e.g. post-cardiopulmonary inflammation and transplant rejection. Complement inhibition represents a potential therapeutic modality for the treatment of such immune-mediated diseases and disease states. Complement inhibitory proteins that systemically inhibit complement have been shown to be effective in various animal models of disease (and in a few clinical trials), but complement inhibitors that target a site of disease and complement activation offer significant potential advantages with regard to safety and efficacy.

In healthy individuals, complement deposition on host cell membranes is prevented by complement inhibitory proteins expressed at the cell surface. These complement inhibitory proteins are also expressed on the surface of tumor cells, often at increased levels, and are considered to be an important contributing factor to the resistance of tumor cells to monoclonal antibody-mediated immunotherapy (monoclonal antibodies that target to tumor cells and activate complement).

The complement system comprises a collection of about 30 proteins and is one of the major effector mechanisms of the immune system. The complement cascade is activated principally via either the classical (usually antibody-dependent) or alternative (usually antibody-idependent) pathways. Activation via either pathway leads to the generation of C3 convertase, which is the central enzymatic complex of the cascade. C3 convertase cleaves serum C3 into C3a and C3b, the latter of which binds covalently to the site of activation and leads to the further generation of C3 convertase (amplification loop). The activation product C3b (and also C4b generated only via the classical pathway) and its breakdown products are important opsonins and are involved in promoting cell-mediated lysis of target cells (by phagocytes and NK cells) as well as immune complex transport and solubilization. C3/C4 activation products and their receptors on various cells of the immune system are also important in modulating the cellular immune response. C3 convertases participate in the formation of C5 convertase, a complex that cleaves C5 to yield C5a and C5b. C5a has powerful proinflammatory and chemotactic properties and can recruit and activate immune effector cells. Formation of C5b initiates the terminal complement pathway resulting in the sequential assembly of complement proteins C6, C7, C8 and (C9)n to form the membrane attack complex (MAC or C5b-9). Formation of MAC in a target cell membrane can result in direct cell lysis, but can also cause cell activation and the expression/release of various inflammatory modulators.

There are two broad classes of membrane complement inhibitor; inhibitors of the complement activation pathway (inhibit C3 convertase formation), and inhibitors of the terminal complement pathway (inhibit MAC formation). Membrane inhibitors of complement activation include complement receptor 1 (CR1), decay-accelerating factor (DAF) and membrane cofactor protein (MCP). They all have a protein structure that consists of varying numbers of repeating units of about 60-70 amino acids termed short consensus repeats (SCR) that are a common feature of C3/C4 binding proteins. Rodent homologues of human complement activation inhibitors have been identified. The rodent protein Crry is a widely distributed inhibitor of complement activation that functions similar to both DAF and MCP. Rodents also express DAF and MCP, although Crry appears to be functionally the most important regulator of complement activation in rodents. Although there is no homolog of Crry found in humans, the study of Crry and its use in animal models is clinically relevant.

Control of the terminal complement pathway and MAC formation in host cell membranes occurs principally through the activity of CD59, a widely distributed 20 kD glycoprotein attached to plasma membranes by a glucosylphosphatidylinositol (GPI) anchor. CD59 binds to C8 and C9 in the assembling MAC and prevents membrane insertion.

Various types of complement inhibitory proteins, including several that are based on soluble forms of membrane complement inhibitors, are currently under investigation for therapy of inflammatory and ischemic disease and disease states associated with bioincompatability (reviewed in refs (9-11)). Almost all previous therapeutic studies (in animal models and in the clinic) have been performed with systemic complement inhibitors, even though it is recognized that systemic suppression of the complement system is likely to compromise host defense and immune homeostasis (9, 12, 13) Systemic inhibition at the C3 step is particularly undesirable due to important physiological functions of C3 and C5 activation products. In conditions where C3 and C5 activation products are also involved in disease pathogenesis, we hypothesize that appropriate targeting of a complement inhibitor that functions early in the pathway (eg. Crry) will minimize systemic inhibition while maintaining an effective local concentration. On the other hand, if the MAC plays a critical role in pathogenesis, complement inhibition late in the pathway (eg. by CD59) will be advantageous since the generation of C3 and C5 activation products will not be altered. However, soluble CD59 is not an effective inhibitor and specific inhibition of the MAC following systemic administration has not been accomplished in vivo.

II. SUMMARY OF THE INVENTION

In accordance with the purposes of this invention, as embodied and broadly described herein, this invention, in one aspect, relates to tubule targeted modulators of complement activity.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

III. BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 1 shows the in vitro characterization of targeted complement inhibitors. (a) Binding of iodinated recombinant proteins to rat kidney proximal tubular epithelial cells (PTEC) in the absence and presence of 100-fold excess of unlabeled recombinant protein (mean+/−SD, n=3). (b) and (c) Inhibition of complement mediated cell lysis by recombinant complement inhibitors, Crry and CD59. Antibody sensitized rat PTEC were preincubated with recombinant proteins followed by the addition of 10% normal rat serum. Cell lysis was determined after 40 min at 37° C. Percent inhibitory activity relative to 100% lysis control group shown (mean+/−SD, n=4). (d) Effect of recombinant proteins on C3 deposition on rat PTEC. Antibody sensitized rat PTEC were incubated with the indicated protein, the cells washed and then incubated with C6-deficient rat serum. C3 deposition was determined by flow cytometry (mean+/−SD, n=3).

Figure 2:
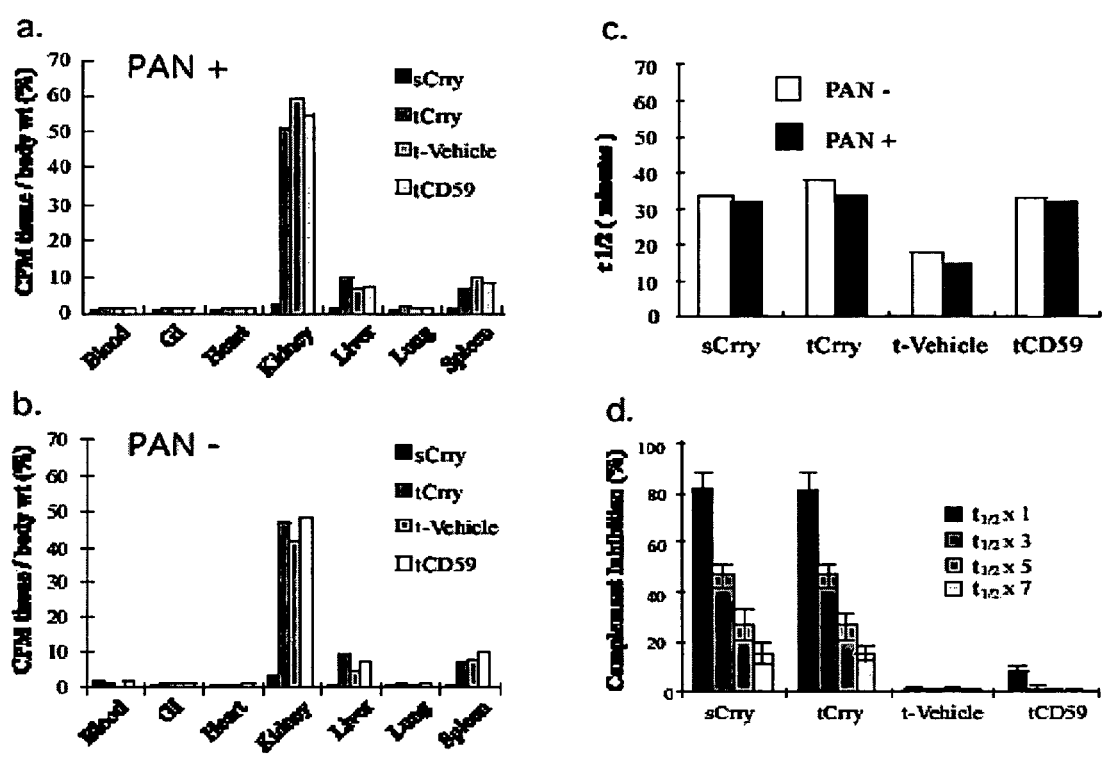

FIG. 2 shows the in vivo characterization of targeted complement inhibitors. (a) and (b) Biodistribution of iodinated recombinant proteins in rats treated with (a) or without (b) puromycin aminonucleoside (PAN). Biodistribution was determined 48 h after tail vein injection. Average of two determinations shown. (c) Blood clearance of the recombinant proteins in rats. Iodinated proteins were injected i.v. into rats treated with or without PAN and blood samples taken periodically from the tail vein for radioactive counting and half life determination (t½). (d) Complement inhibitory activity in rat serum after administration of recombinant proteins. Rat serum samples were obtained periodically following injection of 40 mg/kg recombinant protein and complement inhibitory activity of serum determined using sensitized sheep erythrocytes as targets. Percent inhibitory activity relative to serum from PBS-treated rats is shown (mean+/−SD, n=3)

Figure 3:
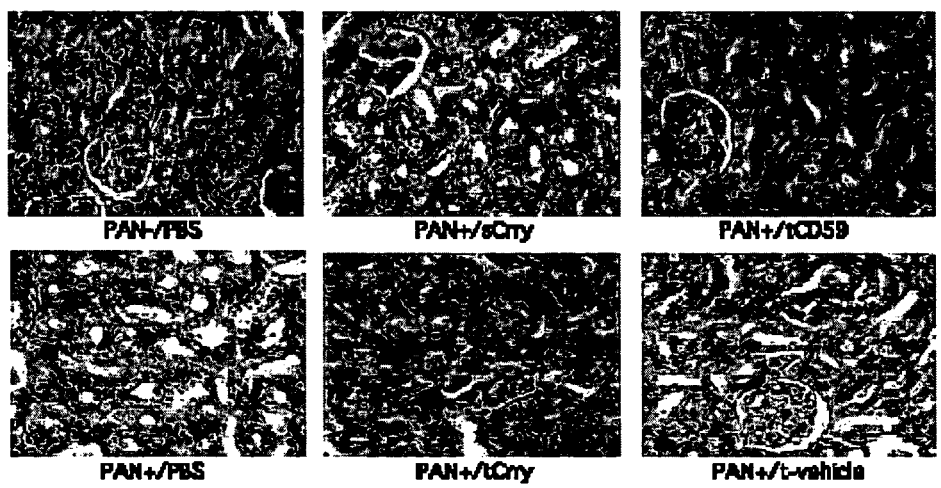
Figure 3:
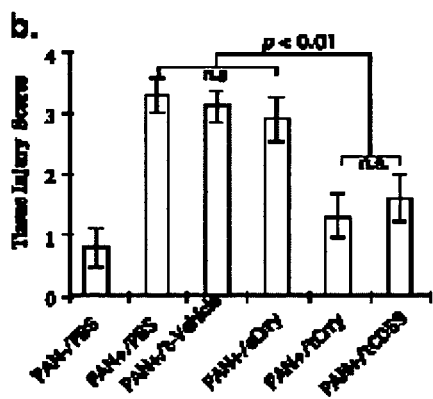
Figure 3:
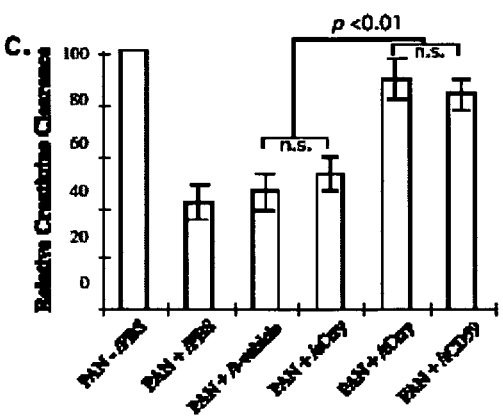

FIG. 3 shows the histological and functional assessment of tubulointerstitial injury. (a) PAS staining of kidney sections from different treatment groups. Representative images are shown. (b) semiquantitative analysis of tubulointerstitial injury as assessed by tubular dilation and degeneration. (c) Creatinine clearance in proteinuric rats treated with recombinant complement inhibitors. Percent clearance relative to clearance in healthy rats (PAN−/PBS) is shown (mean+/−SD, n=4).

Figure 4:
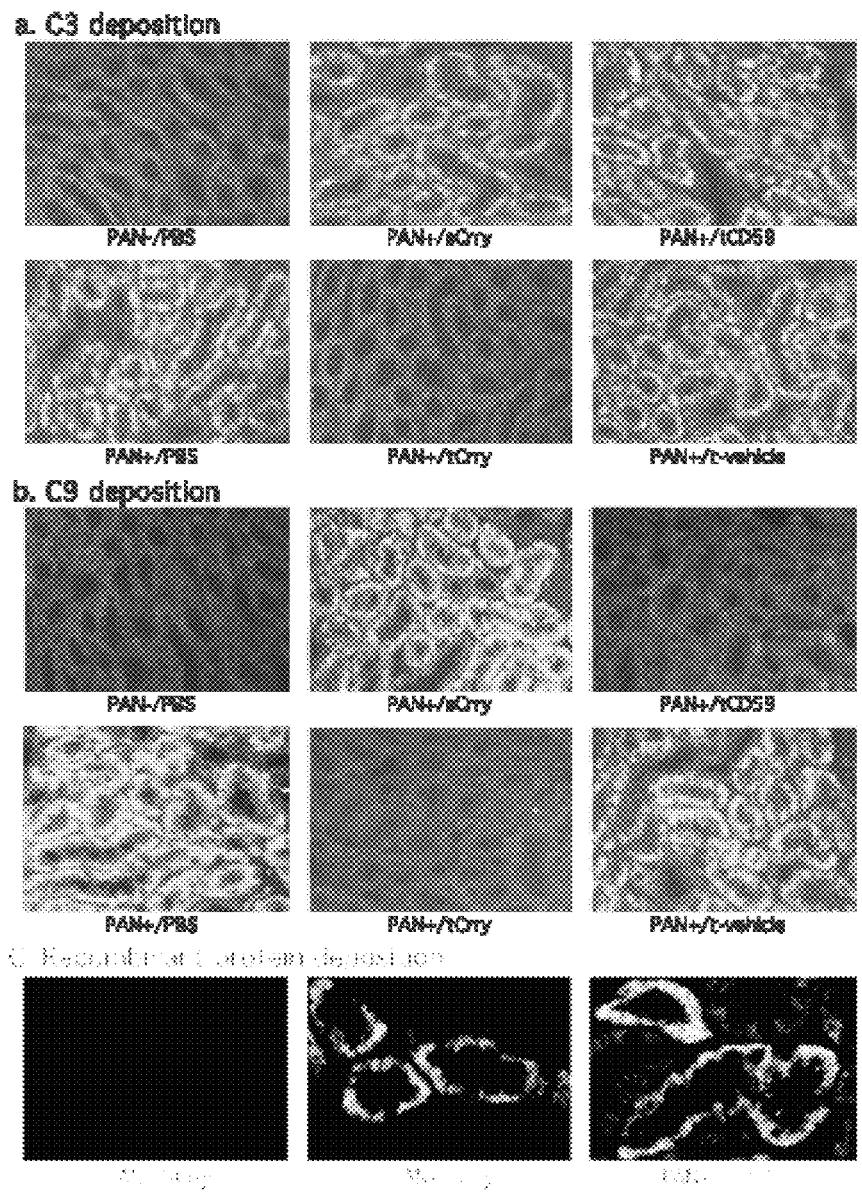

FIG. 4 shows the immunofluorescence microscopy showing C3 deposition (a) C9 deposition (b) and complement inhibitor binding to tubular cells (c). Sections were prepared from kidneys isolated from rats treated with recombinant complement inhibitors. Representative images are shown.

Figure 5:
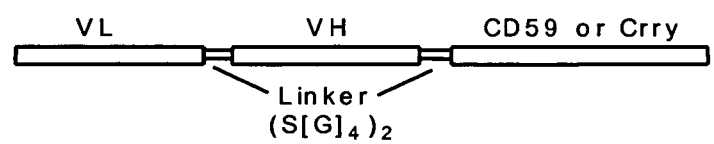

FIG. 5 shows the single chain antibody CD59 or Crry construct. The figure shows the construct comprises a variable light chain (VL) and a variable heavy chain (VH) from K9/9 mAb. The construct was prepared in the yeast expression vector pPICZalph (Invitrogen).

Figure 6:
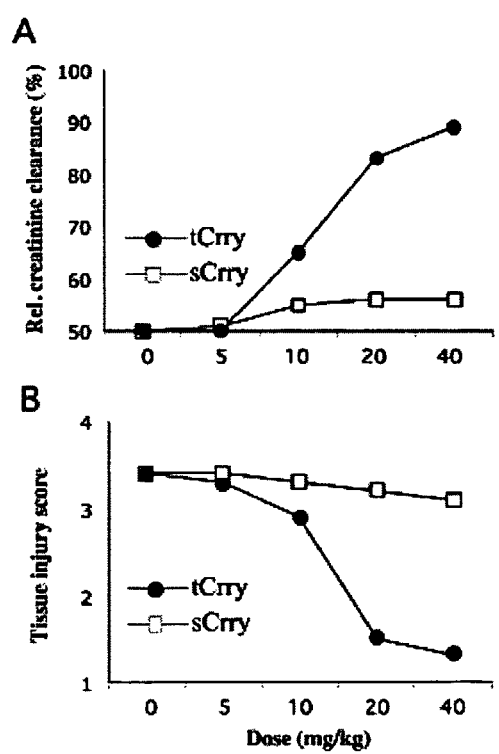

FIG. 6 shows the dose response of targeted and untargeted Crry in proteinuric rats. Effect of tCrry and sCrry on creatinine clearance (A), relative to clearance in healthy rats, and tubulointerstitial injury (B) as assessed by tubular dilation and degeneration. Injury was defined using a scale of 0-4 as defined in *Materials and Methods*. Shown is the average of two determinations.

IV. DETAILED DESCRIPTION

The present invention can be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods, specific recombinant biotechnology methods unless otherwise specified, or to particular reagents unless otherwise specified, as such can, of course, vary. It is also to be understood that the terminology used herein is for the purpose of describing particular embodiments only and is not intended to be limiting.

A. Definitions,

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Treatment" or "treating" means to administer a composition to a subject with a condition, wherein the condition can be any pathogenic disease, autoimmune disease, cancer or inflammatory condition. The effect of the administration of the composition to the subject can have the effect of but is not limited to reducing the symptoms of the condition, a reduction in the severity of the condition, or the complete ablation of the condition.

Herein, "inhibition" or "inhibits" means to reduce activity. It is understood that inhibition can mean a slight reduction in activity to the complete ablation of all activity. An "inhibitor" can be anything that reduces activity.

Herein, "activation" or "activates" means to increase activity. It is understood that activation can mean an increase in existing activity as well as the induction of new activity. An "activator" can be anything that increases activity.

B. Complement Inhibiting and Activating Constructs

The present disclosure establishes the use of targeted complement inhibitors in vivo and demonstrate important benefits of targeted versus untargeted systemic complement inhibition in a model of disease. Disclosed are compositions comprising a construct, wherein the construct comprises renal tubule targeted antibody and a modulator of complement activity.

K9/9 is a single chain anti-proximal tubule antibody. The antibody is specific for dipeptidylpeptidase IV (DPPIV) that is expressed on rat glomerular epithelial cells and PTEC.

It is understood and herein contemplated that other proximal tubule targeting vehicles can be used in the methods and compositions disclosed to target complement modulators. Although a K9/9 targeting vehicle is used in these studies, the same principles apply for other targeting vehicles. Examples of other targeting moieties include but are not limited to antibodies to the Human homologue of K9/9 antigen, dipeptidylpeptidase IV (DPPIV) (SEQ ID NO: 13), Lrp2 (megalin), Cubn (cubilin), Abcc2 (ATP binding cassette, sub-family C, member 2), Abcc4 (ATP binding cassette, sub-family C, member 4), Abcb1b (ATP binding cassette, sub-family B, member 1; P-glycoprotein), Slc1a1 (excitatory amino acid carrier 1), Slc3a1 (cystine, dibasic and neutral amino acid transporters), Slc5a1 (sodium/glucose cotransporter 1), Slc5a2 (sodium/glucose cotransporter 2), Slc9a3 (sodium/hydrogen exchanger 3), Slc10a2 (sodium/taurocholate contransporting polypeptide), Slc13a2 (sodium dependent dicarboxylate cotransporter), Sic15a1 (oligopeptide transporter 1), Sic15a2 (oligopeptide transporter 2), Slc17a1 (sodium phosphate transporter 1), Slc17a2 (sodium phosphate transporter 3), Slc17a3 (sodium phosphate transporter 4), Slco1a1 (organic anion transporter protein 1), Slc22a4 (organic cation transporter OCTN1), Slc22a5 (organic cation transporter OCTN2), Slc22a11 (organic anion transporter 4), Slc34a1 (sodium phosphate transporter IIa), megalin (low density lipoprotein receptor-related protein 2, LRP2), neutral endopeptidase (NEP), CD10, mucin 20 (or other mucins) (SEQ ID NO: 14), kidney-injury molecule 1 (KIM-1) (SEQ ID NO: 15) or hepatitis A virus cellular receptor 1 and megalin. Additionally one of skill in the art understands that certain advantages may exist that will aid in determining a preference for a particular targeting moiety. For example, the last four targeting moieties have high expression in the apical membrane of the PTEC, their protein structure is known, and, in the case of the latter two, are highly expressed in states in which the PTEC is injured. Thus, for example, disclosed and herein contemplated are compositions of the invention comprising anti-human DPPIV antibody or fragment thereof linked to CD59.

It is understood that species and strain variations exist for the disclosed peptides, polypeptides, proteins, protein fragments and compositions. Specifically disclosed are all species and strain variations for the disclosed peptides, polypeptides, proteins, protein fragments and compositions.

Also disclosed are compositions, wherein the construct is a fusion protein.

Herein a "fusion protein" means two or more components comprising peptides, polypeptides, or proteins operably linked. K9/9 can be linked to complement inhibitors or activators by an amino acid linking sequence. Examples of linkers are well known in the art. Examples of linkers can include but are not limited to $(Gly_4Ser)_2$, $(Gly_4Ser)_3$ (G4S), $(Gly_3Ser)_4$ (G3S), $SerGly_4$, and $SerGly_4SerGly_4$. Linking sequences can also consist of "natural" linking sequences found between SCR units within human (or mouse) proteins, for example VSVFPLE, the linking sequence between SCR 2 and 3 of human CR2, can be used to link the inhibitors of the invention with K9/9. Fusion proteins can also be constructed without linking sequences. Fusion proteins are also refered to as "recombinant proteins" herein.

Also disclosed are compositions of the invention, wherein the fusion protein inhibits complement.

Also disclosed are compositions of the invention, wherein the modulator of complement activity comprises a complement inhibitor.

Also disclosed are compositions of the invention wherein; for example, the complement inhibitor is decay accelerating factor (DAF), for example SEQ ID NO: 2 (amino acid) encoded by SEQ ID NO: 1 (nucleotide). For example, the DAF can be soluble human DAF comprising the four SCR domains without glycophosphatidyl anchor and serine-threonine rich region. The DAF can also be soluble human DAF comprising the four SCR domains and the serine-threonine rich region but without glycophosphatidyl anchor.

The DAF extracellular region consists of 4 SCR units at N-terminus followed by serine/threonine rich region. Amino acids 1-34 comprise the leader peptide, amino acids 35-95 comprise SCR1, amino acids 97-159 comprise SCR2, amino acids 162-221 comprise SCR3, amino acids 224-284 comprise SCR4, and amino acids 287-356 comprise the S/T region. Thus specifically disclosed herein are compositions of the invention wherein the composition comprises all 4 SCR units. Also disclosed herein are compositions of the invention, wherein the composition comprises for example, SCR2-4 of DAF.

Disclosed are compositions of the invention, wherein the complement inhibitor comprises a fusion protein between CD59 and another complement inhibitor selected from the group consisting of DAF, MCP, Crry, and CR1. Also disclosed are compositions of the invention, wherein the complement inhibitor is a fusion protein of two or more complement inhibitors.

Also disclosed are compositions of the invention, wherein the fusion protein comprises K9/9-DAF. Also disclosed are compositions of the invention wherein the fusion protein is encoded by a nucleic acid comprising K9/9-DAF encoding sequences.

Also disclosed are compositions of the invention, wherein the complement inhibitor is human CD59 (SEQ ID NO: 3 (nucleotide) and SEQ ID NO: 4 (amino acid)). The human CD59 can be soluble human CD59 comprising the mature protein without glycophosphatidyl anchor.

Also disclosed are compositions of the invention, wherein the fusion protein comprises K9/9-CD59 (SEQ ID NO: 12). Also disclosed are compositions of the invention wherein the fusion protein is encoded by a nucleotide.

Also disclosed are compositions of the invention, wherein the complement inhibitor is CR1 (SEQ ID NO: 5 (nucleotide) and SEQ ID NO: 6 (amino acid)). The extracellular region of CR1 can comprise 30 SCR units. It is an embodiment of the invention that the composition can comprise the entire extracellular region of CR1. In another embodiment of the invention, the composition comprises [the] one active site[s] of CR1. The active sites of CR1 are amino acids 1-46 which comprise the leader peptide, amino acids 47-300 which comprise SCR1-4 (C4b binding site, lower affinity for C3b), amino acids 497-750 which comprise SCR8-11 (C3b binding site, lower affinity for C4b), amino acids 947-1200 which comprise SCR15-18 (C3b binding site, lower affinity for C4b), and amino acids 1400-1851 which comprise the C1q binding site. In an additional embodiment of the invention, the composition of the invention can comprise any [one or] combination or all of the active sites of CR1.

Also disclosed are compositions of the invention, wherein the complement inhibitor comprises the active sites of CR1, and wherein [the] one active site[s] further comprise a leader peptide comprising amino acids 6-46, amino acids 47-300 which comprise SCR1-4 (C4b binding site, lower affinity for C3b), amino acids 497-750 which comprise SCR8-11 (C3b binding site, lower affinity for C4b), amino acids 947-1200 which comprise SCR15-18 (C3b binding site, lower affinity for C4b), and amino acids 1400-1851 which comprise the C1q binding site. In an additional embodiment of the invention, the composition of the invention can comprise any [one or] combination or all of the active sites of CR1.

Also disclosed are compositions of the invention, wherein the complement inhibitor is MCP (SEQ ID NO: 7 (nucleotide) and SEQ ID NO: 8 (amino acid)). The extracellular region consists of 4 SCR units followed by ser/thr region. Amino acids 1-34 comprise the leader peptide, amino acids 35-95 comprise SCR1, amino acids 96-158 comprise SCR2, amino acids, 159-224 comprise SCR3, amino acids 225-285 comprise SCR4, and amino acids 286-314 comprise the S/T region Also disclosed are compositions of the invention, wherein the complement inhibitor is Crry (SEQ ID NO: 9). The Crry can be soluble mouse Crry comprising the 5 N-terminal SCR domains without transmembrane region.

Also disclosed are compositions of the invention, wherein the fusion protein comprises K9/9-Crry (SEQ ID NO: 11). Also disclosed are compositions of the invention wherein the fusion protein is encoded by a nucleotide.

Also disclosed are compositions of the invention, wherein the complement inhibitor is murine CD59. The murine CD59 can be soluble murine CD59 comprising the mature protein without glycophosphatidyl anchor.

It is understood and herein disclosed that instances can exist where the administration of a composition comprising a single fusion protein or immunoconjugate may be improved upon through the administration of multiple fusion proteins or immunoconjugates. Therefore, disclosed are compositions of the invention comprising more than one fusion protein or immunoconjugate of the invention. The compositions with more than one fusion protein can include fusion proteins chosen from the list of fusion proteins described herein, for example in Example 5. As a specific example, a composition comprising K9/9-CD59 fusion protein and K9/9-Crry fusion protein is provided. It is understood that compositions comprising more than one fusion protein or immunoconjugate can be administered such that all fusion proteins or immunoconjugates are administered concurrently. This would include but not be limited to, for example, the administration of a single composition comprising more than one fusion construct, and the administration of two separate fusion constructs concurrently. Also disclosed are methods of the invention comprising administering the compositions of the invention sequentially. For example, a K9/9-Crry fusion is administered followed by a K9/9-CD59 fusion. Alternatively, a K9/9-CD59 fusion is administered first, followed by a K9/9-Crry fusion.

Disclosed are compositions of the invention, wherein the construct is in a vector.

Disclosed are cells comprising the vector of the invention.

Also disclosed are compositions, wherein the construct is an immunoconjugate. Herein "immunoconjugate" means two or more components comprising peptides, polypeptides, or proteins, one of which is an immunoreactive component, operably linked by a chemical cross-linker. Linking of the components of the immunoconjugate can occur on reactive groups located on the component. Reactive groups that can be targeted using a cross-linker include primary amines, sulfhydryls, carbonyls, carbohydrates and carboxylic acids, or active groups can be added to proteins. Examples of chemical linkers are well known in the art and can include but are not limited to bismaleimidohexane, m-maleimidobenzoyl-N-hydroxysuccinimide ester, NHS-Esters-Maleimide Crosslinkers such as MBS, Sulfo-MBS, SMPB, Sulfo-SMPB, GMBS, Sulfo-GMBS, EMCS, Sulfo-EMCS; Imidoester Cross-linkers such as DMA, DMP, DMS, DTBP; EDC [1-Ethyl-3-(3-Dimethylaminopropyl)carbodiimide Hydrochloride], [2-(4-Hydroxyphenyl)ethyl]-4-N-maleimidomethyl)-cyclohexane-1-carboxamide, DTME: Dithio-bis-maleimidoethane, DMA (Dimethyl adipimidate•2 HCl), DMP (Dimethyl pimelimidate•2 HCl), DMS (Dimethyl suberimidate•2 HCl), DTBP (Dimethyl 3,3'-dithiobispropionimidate•2HCl), MBS, (m-Maleimidobenzoyl-N-hydoxysuccinimide ester), Sulfo-MBS (m-Maleimidobenzoyl-N-hydoxysuccinimide ester), Sulfo-SMPB (Sulfosuccinimidyl 4-[p-maleimidophenyl]butyrate(, GMBS (N-[•-maleimidobutyryloxy]succinimide ester), EMCS(N-[•-maleimidocaproyloxy]succinimide ester), and Sulfo-EMCS(N-[•-maleimidocaproyloxy]sulfosuccinimide ester).

C. Methods of Using the Compositions

Various types of complement inhibitory proteins are currently under investigation for therapy of inflammatory disease and disease states associated with bioincompatibility.

Disclosed are methods of treating a condition affected by complement in a subject comprising administering to the subject the composition of the invention. It is understood that administration of the composition to the subject can have the effect of, but is not limited to, reducing the symptoms of the condition, a reduction in the severity of the condition, or the complete ablation of the condition.

1. Methods of Using the Compositions to Inhibit Complement

Disclosed are methods of treating a condition affected by complement in a subject comprising administering to the subject the composition of the invention, wherein the composition will inhibit complement activity. It is understood that the effect of the administration of the composition to the subject can be, but is not limited to, reducing the symptoms of the condition, a reduction in the severity of the condition, or the complete ablation of the condition.

Disclosed are methods of reducing complement-mediated damage comprising administering to a subject the composition of the invention, which inhibits complement.

Disclosed are methods of the invention, wherein the condition treated is an inflammatory condition, an ischemic condition or a condition relating to bioincompatibility. Also disclosed are methods of the invention, wherein the inflammatory condition can be selected from the group consisting of nephritis, Proteinuria, Diabetic nephropathy, Focal and segmental glomerulosclerosis, Membranous nephropathy, IgA nephropathy, Lupus nephritis, Minimal change disease, Amyloidosis, Membranoproliferative glomerulonephritis, Essential mixed cryoglobulinemia (includes secondary to hepatitis C), Light chain deposition disease, Vasculitis (includes Wegener's granulomatosis, microscopic polyangiitis and renal limited vasculitis), Congenital nephrotic syndrome, Fibrillary glomerulonephritis, Mesangial proliferative, glomerulonephritis, Postinfectious glomerulonephritis, Drug-induced nephrotic syndrome, Chronic allograft rejection, Preeclampsia/eclampsia, Hypertensive nephrosclerosis, and Immunotactoid glomerulonephritis.

Disclosed are methods of the invention, wherein complement inhibitor can enhance the outcome of apoptosis-base therapy (e.g., gene therapy with adenovirus expressing Fas ligand).

Apoptosis occurring during normal development is non inflammatory and is involved in induction of immunological tolerance. Although apoptotic cell death can be inflammatory depending on how it is activated and in what cell types (for example, therapeutic agents that ligate Fas are able to induce inflammation), necrotic cell death results in a sustained and powerful inflammatory response mediated by released cell contents and by proinflammatory cytokines released by stimulated phagocytes. Apoptotic cells and vesicles are normally cleared by phagocytes, thus preventing the pro-inflammatory consequences of cell lysis. In this context, it has been shown that apoptotic cells and apoptotic bodies directly fix complement, and that complement can sustain an anti-inflammatory response due to opsonization and enhanced phagocytosis of apoptotic cells.

Inflammation is involved in non specific recruitment of immune cells that can influence innate and adaptive immune responses. Modulating complement activation during apoptosis-based tumor therapy to inhibit phagocytic uptake of apoptotic cells/bodies enhances the inflammatory/innate immune response within the tumor environment. In addition, apoptotic cells can be a source of immunogenic self antigens and uncleared apoptotic bodies can result in autoimmunization. In addition to creating an enhanced immuno-stimulatory environment, modulating complement at a site in which tumor cells have been induced to undergo apoptosis further augments or triggers specific immunity against a tumor to which the host is normally tolerant.

In the methods of the invention, the subject can be a mammal. For example, the mammal can be a human, nonhuman primate, mouse, rat, pig, dog, cat, monkey, cow, or horse.

D. Compositions

Disclosed are the components to be used to prepare the disclosed compositions as well as the compositions themselves to be used in the methods disclosed herein. These and other materials are disclosed herein, and it is understood that when combinations, subsets, interactions, groups, etc. of these materials are disclosed that while specific reference for each of the various individual and collective combinations and permutation of these compounds may not be explicitly made, each is specifically contemplated and described herein. For example, if a particular K9/9, DAF, CD59, CR1, MCP, Crry is described, and/or a specific combination thereof is disclosed and discussed and/or a number of modifications that can be made to a number of molecules including the K9/9, DAF, CD59, CR1, MCP, Crry, and/or combination thereof are discussed, specifically contemplated is each and every combination and permutation of K9/9, DAF, CD59, CR1, MCP, Crry, or combination thereof and the modifications that are possible, unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

1. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the genes and proteins disclosed herein, is through defining the variants and derivatives in terms of homology to specific known sequences. This identity of particular sequences disclosed herein is also discussed elsewhere herein. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods can differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

2. Nucleic Acids

There are a variety of molecules disclosed herein that are nucleic acid based, including for example the nucleic acids that encode, for example K9/9, DAF, CD59, CR1, MCP, Crry, K9/9-DAF, K9/9-CD59, K9/9-CR1, K9/9-MCP, K9/9-CD59 (human), or K9/9-Crry as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, the expressed mRNA will typically be made up of A, C, G, and U. Likewise, it is understood that if, for example, an antisense molecule is introduced into a cell or cell environment through, for example exogenous delivery, it is advantageous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate).

A nucleotide analog is a nucleotide which contains some type of modification to any of the base, sugar, or phosphate moieties. Modifications to the base moiety would include natural and synthetic modifications of A, C, G, and T/U as well as different purine or pyrimidine bases, such as uracil-5-yl (.psi.), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$, alkyl or $C_2$ to $C_{10}$ alkenyl and alkynyl. 2' sugar modifications also include but are not limited to —O[$(CH_2)_nO]_m$ $CH_3$, —O$(CH_2)_n$OCH$_3$, —O$(CH_2)_n$NH$_2$, —O$(CH_2)_n$CH$_3$, —O$(CH_2)_n$—ONH$_2$, and —O$(CH_2)_n$ON[$(CH_2)_n$CH$_3$)]$_2$, where n and m are from 1 to about 10.

Other modifications at the 2' position include but are not limited to: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications can also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs can also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717;

5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only contain a single modification, but can also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., Science, 1991, 254, 1497-1500).

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937. Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

b) Sequences

There are a variety of sequences related to the K9/9, DAF, CD59, CR1, MCP, Crry, K9/9-DAF, K9/9-CR1, K9/9-MCP, K9/9-CD59, K9/9-CD59 (human), or K9/9-Crry genes having, for example, the sequences as disclosed herein or sequences available in the literature. These sequences and others are herein incorporated by reference in their entireties as well as for individual subsequences contained therein.

One particular sequence set forth in SEQ ID NO: 11 used herein, as an example, to exemplify the disclosed compositions and methods. It is understood that the description related to this sequence is applicable to any sequence related to K9/9, K9/9-DAF, K9/9-CD59, K9/9-CD59 (human), K9/9-CR1, K9/9-MCP, or K9/9-Crry, unless specifically indicated otherwise. Those of skill in the art understand how to resolve sequence discrepancies and differences and to adjust the compositions and methods relating to a particular sequence to other related sequences (i.e. sequences of K9/9, DAF, CD59, CR1, MCP, Crry, K9/9-DAF, K9/9-CR1, K9/9-MCP, K9/9-CD59, K9/9-CD59 (human), or K9/9-Crry. Primers and/or probes can be designed for any K9/9, DAF, CD59, CR1, MCP, Crry, K9/9-DAF, K9/9-CD59, K9/9-CD59 (human), K9/9-CR1, K9/9-MCP, and K9/9-Crry sequence given the information disclosed herein and known in the art.

3. Delivery of the Compositions to Cells

There are a number of compositions and methods which can be used to deliver the present fusion protein compositions, immunoconjugate compositions, and nucleic acid compositions to cells, either in vitro or in vivo. Compositions of the invention are preferably administered to a subject in a pharmaceutically acceptable carrier. Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carriers include, but are not limited to, saline, water:oil emulsions, oil:water emulsions, water:oil:water emulsions, and Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The compositions of the invention can be administered to the subject, patient, or cell by injection (e.g., intravenous, intraperitoneal, subcutaneous, intramuscular), or by other methods such as infusion that ensure its delivery to the bloodstream in an effective form. Local or intravenous injection is preferred.

Effective dosages and schedules for administering the compositions of the invention can be determined empirically, and making such determinations is within the skill in the art. Those skilled in the art will understand that the dosage of the compositions of the invention that must be administered will vary depending on, for example, the subject that will receive the composition, the route of administration, the particular type of composition used and other drugs being administered. A typical daily dosage of the compositions of the invention used alone might range from about 1 μg/kg to up to 100 mg/kg of body weight or more per day, depending on the factors mentioned above.

a) Nucleic Acid Based Delivery Systems

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991) Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, into the cell without degradation and include a promoter yielding expression of the gene in the cells into which it is delivered. In some embodiments the K9/9, DAF, CD59, CR1, MCP, Crry, K9/9-DAF, K9/9-CR1, K9/9-MCP, K9/9-CD59, K9/9-CD59 (human), or K9/9-Crry s are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes. They are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

(1) Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

(2) Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

(3) Adeno-Asscociated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorproated by reference for material related to the AAV vector.

The vectors of the present invention thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and can contain upstream elements and response elements.

(4) Large Payload Viral Vectors

Molecular genetic experiments with large human herpesviruses have provided a means whereby large heterologous DNA fragments can be cloned, propagated and established in cells permissive for infection with herpesviruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

b) Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed K9/9, DAF, CD59, CR1, MCP, Crry, K9/9-DAF, K9/9-CR1, K9/9-MCP, K9/9-CD59, K9/9-CD59 (human), or K9/9-Crry or vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials can be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., *Bioconugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.*, 4:3-9, (1993); Battelli, et al., *Cancer Immunol. Immunother.,* 35:421-425, (1992); Pietersz and McKenzie, *Immunolog. Reviews,* 129: 57-80, (1992); and Roffler, et al., *Biochem. Pharmacol,* 42:2062-2065, (1991)). These techniques can be used for a variety of other speciifc cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

c) In Vivo/Ex Vivo

As described above, the compositions can be administered in a pharmaceutically acceptable carrier and can be delivered to the subject=s cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

4. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and can contain upstream elements and response elements.

a) Viral Promoters and Enhancers

Preferred promoters controlling transcription from vectors in mammalian host cells can be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell Bio.* 4: 1293 (1984)). They are usually between 10 and 300 bp in length, and they function in cis. Enhancers f unction to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer can be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) can also contain sequences necessary for the termination of transcription which can affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes β-galactosidase, and green fluorescent protein.

In some embodiments the marker can be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

5. Peptides a) Protein Variants

As discussed herein there are numerous variants of the K9/9, DAF, CD59, CR1, MCP, Crry, K9/9-DAF, K9/9-CR1, K9/9-MCP, K9/9-CD59, K9/9-CD59 (human), or K9/9-Crry protein that are known and herein contemplated. In addition, to the known functional K9/9, DAF, CD59, CR1, MCP, Crry, K9/9-DAF, K9/9-CD59, K9/9-CD59 (human), K9/9-CR1, K9/9-MCP, and K9/9-Crry, strain variants, there are derivatives of the K9/9, DAF, CD59, CR1, MCP, Crry, K9/9-DAF, K9/9-CD59, K9/9-CD59 (human), K9/9-CR1, K9/9-MCP, and K9/9-Crry proteins which also function in the disclosed methods and compositions. Protein variants and derivatives are well understood to those of skill in the art and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof can be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations |
| --- | --- |
| alanine | Ala A |
| allosoleucine | AIle |
| arginine | Arg R |
| asparagine | Asn N |
| aspartic acid | Asp D |
| cysteine | Cys C |
| glutamic acid | Glu E |
| glutamine | Gln Q |
| glycine | Gly G |
| histidine | His H |
| isolelucine | Ile I |
| leucine | Leu L |
| lysine | Lys K |
| phenylalanine | Phe F |
| proline | Pro P |

TABLE 1-continued

Amino Acid Abbreviations

| Amino Acid | Abbreviations |
| --- | --- |
| pyroglutamic acidp | pGlu |
| serine | Ser S |
| threonine | Thr T |
| tyrosine | Tyr Y |
| tryptophan | Trp W |
| valine | Val V |

TABLE 2

Amino Acid Substitutions

Original Residue Exemplary Conservative Substitutions, others are known in the art.

Ala; Ser
Arg; Lys; Gln
Asn; Gln; His
Asp; Glu
Cys; Ser
Gln; Asn, Lys
Glu; Asp
Gly; Pro
His; Asn; Gln
Ile; Leu; Val
Leu; Ile; Val
Lys; Arg; Gln;
Met; Leu; Ile
Phe; Met; Leu; Tyr
Ser; Thr
Thr; Ser
Trp; Tyr
Tyr; Trp; Phe
Val; Ile; Leu

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO: 10 sets forth a particular sequence of K9/9 and SEQ ID NO: 2 sets forth a particular sequence of a DAF protein. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. It is understood that for this mutation all of the nucleic acid sequences that encode this particular derivative of any of the disclosed sequences are also disclosed. It is also understood that while no amino acid sequence indicates what particular DNA sequence encodes that protein within an organism, where particular variants of a disclosed protein are disclosed herein, the known nucleic acid sequence that encodes that protein from which that protein arises is also known and herein disclosed and described.

6. Antibodies a) Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as described herein. The antibodies are tested for their desired activity using the in vitro assays described herein, or by analogous methods, after which their in vivo therapeutic and/or prophylactic activities are tested according to known clinical testing methods.

As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these can be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

As used herein, the term "antibody or fragments thereof" encompasses chimeric antibodies and hybrid antibodies, with dual or multiple antigen or epitope specificities, and fragments, such as scFv, sFv, F(ab')2, Fab', Fab and the like, including hybrid fragments. Thus, fragments of the antibodies that retain the ability to bind their specific antigens are provided. For example, fragments of antibodies which maintain complement binding activity binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods of the invention serves to lessen the chance that an antibody administered to a human will evoke an undesirable immune response.

Optionally, the antibodies are generated in other species and "humanized" for administration in humans. Humanized forms of non-human (e.g., murine) antibodies are chimeric immunoglobulins, immunoglobulin chains or fragments thereof (such as Fc, scFv, sFv, Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies can also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992)).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody (Sims et al., J. Immunol., 151:2296 (1993) and Chothia et al., J. Mol. Biol., 196:901 (1987)). Another method uses a particular framework derived from the consensus sequence of all human antibodies of a particular subgroup of light or heavy chains. The same framework can be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see, WO 94/04679, published 3 Mar. 1994).

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

An isolated immunogenically specific paratope or fragment of the antibody is also provided. A specific immunogenic epitope of the antibody can be isolated from the whole antibody by chemical or mechanical disruption of the molecule. The purified fragments thus obtained are tested to determine their immunogenicity and specificity by the methods taught herein. Immunoreactive paratopes of the antibody, optionally, are synthesized directly. An immunoreactive fragment is defined as an amino acid sequence of at least about two to five consecutive amino acids derived from the antibody amino acid sequence.

One method of producing proteins comprising the antibodies of the present invention is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the antibody of the present invention, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY. Alternatively, the peptide or polypeptide is independently synthesized in vivo as described above. Once isolated, these independent peptides or polypeptides can be linked to form an antibody or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

The invention also provides fragments of antibodies which have bioactivity. The polypeptide fragments of the present invention can be recombinant proteins obtained by cloning nucleic acids encoding the polypeptide in an expression system capable of producing the polypeptide fragments thereof, such as an adenovirus or baculovirus expression system. For example, one can determine the active domain of an antibody from a specific hybridoma that can cause a biological effect associated with the interaction of the antibody with an Fc receptor. For example, amino acids found to not contribute to either the activity or the binding specificity or affinity of the antibody can be deleted without a loss in the respective activity. For example, in various embodiments, amino or carboxy-terminal amino acids are sequentially removed from either the native or the modified non-immunoglobulin molecule or the immunoglobulin molecule and the respective activity assayed in one of many available assays. In another example, a fragment of an antibody comprises a modified antibody wherein at least one amino acid has been substituted for the naturally occurring amino acid at a specific position, and a portion of either amino terminal or carboxy terminal amino acids, or even an internal region of the antibody, has been replaced with a polypeptide fragment or other moiety, such as biotin, which can facilitate in the purification of the modified antibody.

The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody can be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller M J et al. Nucl. Acids Res. 10:6487-500 (1982).

A variety of immunoassay formats can be used to select antibodies that selectively bind with a particular protein, variant, or fragment. For example, solid-phase ELISA immunoassays are routinely used to select antibodies selectively immunoreactive with a protein, protein variant, or fragment thereof. See Harlow and Lane. Antibodies, A Laboratory Manual. Cold Spring Harbor Publications, New York, (1988), for a description of immunoassay formats and conditions that could be used to determine selective binding. The binding affinity of a monoclonal antibody can, for example, be determined by the Scatchard analysis of Munson et al., Anal. Biochem., 107:220 (1980).

Also provided is an antibody reagent kit comprising containers of the monoclonal antibody or fragment thereof of the invention and one or more reagents for detecting binding of the antibody or fragment thereof to the Fc receptor molecule. The reagents can include, for example, fluorescent tags, enzymatic tags, or other tags. The reagents can also include secondary or tertiary antibodies or reagents for enzymatic reactions, wherein the enzymatic reactions produce a product that can be visualized.

b) Human Antibodies

The human antibodies of the invention can be prepared using any technique. Examples of techniques for human monoclonal antibody production include those described by Cole et al. (*Monoclonal Antibodies and Cancer Therapy*, Alan R. Liss, p. 77, 1985) and by Boerner et al. (*J. Immunol.*, 147(1):86-95, 1991). Human antibodies of the invention (and fragments thereof) can also be produced using phage display libraries (Hoogenboom et al., *J. Mol. Biol.*, 227:381, 1991; Marks et al., *J. Mol. Biol.*, 222:581, 1991).

The human antibodies of the invention can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA*, 90:2551-255 (1993); Jakobovits et al., *Nature*, 362:255-258 (1993); Bruggermann et al., *Year in Immunol.*, 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

c) Administration of Antibodies

Antibodies of the invention are preferably administered to a subject in a pharmaceutically acceptable carrier. Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. Local or intravenous injection is preferred.

Effective dosages and schedules for administering the antibodies can be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. Guidance in selecting appropriate doses for antibodies is found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

Following administration of an antibody for treating, inhibiting, or preventing an HIV infection, the efficacy of the therapeutic antibody can be assessed in various ways well known to the skilled practitioner. For instance, one of ordinary skill in the art will understand that an antibody of the invention is efficacious in treating or inhibiting an HIV infection in a subject by observing that the antibody reduces viral load or prevents a further increase in viral load. Viral loads can be measured by methods that are known in the art, for example, using polymerase chain reaction assays to detect the presence of HIV nucleic acid or antibody assays to detect the presence of HIV protein in a sample (e.g., but not limited to, blood) from a subject or patient, or by measuring the level of circulating anti-HIV antibody levels in the patient. Efficacy of the antibody treatment can also be determined by measuring the number of $CD4^+$ T cells in the HIV-infected subject. An antibody treatment that inhibits an initial or further decrease in $CD4^+$ T cells in an HIV-positive subject or patient, or that results in an increase in the number of $CD4^+$ T cells in the HIV-positive subject, is an efficacious antibody treatment.

d) Nucleic Acid Approaches for Antibody Delivery

The compositions of the invention can also be administered to patients or subjects as a nucleic acid preparation (e.g., DNA or RNA) that encodes the antibody or antibody fragment, such that the patient's or subject's own cells take up the nucleic acid and produce and secrete the encoded composition (e.g., K9/9-DAF, K9/9-CD59, K9/9-CR1, K9/9-MCP, K9/9-Crry, K9/9-IgG1 Fc (human), K9/9-IgM Fc, K9/9-IgG3 Fc (murine), or K9/9-CVF).

e) Nucleic Acid Delivery

In the methods described above which include the administration and uptake of exogenous DNA into the cells of a subject (i.e., gene transduction or transfection), the nucleic acids of the present invention can be in the form of naked DNA or RNA, or the nucleic acids can be in a vector for delivering the nucleic acids to the cells, whereby the antibody-encoding DNA fragment is under the transcriptional regulation of a promoter, as would be well understood by one of ordinary skill in the art. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The recombinant retrovirus can then be used to infect and thereby deliver to the infected cells nucleic acid encoding a broadly neutralizing antibody (or active fragment thereof) of the invention. The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), pseudotyped retroviral vectors (Agrawal et al., *Exper. Hematol.* 24:738-747, 1996). Physical transduction techniques can also be used, such as liposome delivery and receptor-mediated and other endocytosis mechanisms (see, for example, Schwartzenberger et al., *Blood* 87:472-478, 1996). This invention can be used in conjunction with any of these or other commonly used gene transfer methods.

As one example, if the complement modulating construct-encoding nucleic acid of the invention is delivered to the cells of a subject in an adenovirus vector, the dosage for administration of adenovirus to humans can range from about $10^7$ to $10^9$ plaque forming units (pfu) per injection but can be as high as $10^{12}$ pfu per injection (Crystal, *Hum. Gene Ther.* 8:985-1001, 1997; Alvarez and Curiel, *Hum. Gene Ther.* 8:597-613, 1997). A subject can receive a single injection, or, if additional injections are necessary, they can be repeated at six month intervals (or other appropriate time intervals, as determined by the skilled practitioner) for an indefinite period and/or until the efficacy of the treatment has been established.

Parenteral administration of the nucleic acid or vector of the present invention, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein. For additional discussion of suitable formulations and various routes of administration of therapeutic compounds, see, e.g., *Remington: The Science and Practice of Pharmacy* (19th ed.) ed. A. R. Gennaro, Mack Publishing Company, Easton, Pa. 1995.

7. Pharmaceutical Carriers/Delivery of Pharamceutical Products

As described above, the compositions can also be administered in vivo in a pharmaceutically acceptable carrier. By "pharmaceutically acceptable" is meant a material that is not biologically or otherwise undesirable, i.e., the material can be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions can be administered orally, parenterally (e.g., intravenously), by intramuscular injection, by intraperitoneal injection, transdermally, extracorporeally, topically or the like, although topical intranasal administration or administration by inhalant is typically preferred. As used herein, "topical intranasal administration" means delivery of the compositions into the nose and nasal passages through one or both of the nares and can comprise delivery by a spraying mechanism or droplet mechanism, or through aerosolization of the nucleic acid or vector. The latter is effective when a large number of animals is to be treated simultaneously. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials can be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129: 57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

8. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended. For example, disclosed is a kit for assessing a subject's risk for cancer, asthma, systemic lupus erythematosus, rheumatoid arthritis, reactive arthritis, spndyarthritis, systemic vasculitis, insulin dependent diabetes mellitus, multiple sclerosis, experimental allergic encephalomyelitis, Sjögren's syndrome, graft versus host disease, inflammatory bowel disease including Crohn's disease, ulcerative colitis, Ischemia reperfusion injury, myocardial infarction, alzheimer's disease, transplant rejection (allogeneic and xenogeneic), thermal trauma, any immune complex-induced inflammation, glomerulonephritis, myasthenia gravis, multiple sclerosis, cerebral lupus, Guillain-Barre syndrome, vasculitis, systemic sclerosis, anaphlaxis, catheter reactions, atheroma, infertility, thyroiditis, ARDS, post-bypass syndrome, hemodialysis, juvenile rheumatoid, Behcets syndrome, hemolytic anemia, pemphigus, bullous pemphigoid, stroke, atherosclerosis, and scleroderma.

9. Compositions with Similar Functions

It is understood that the compositions disclosed herein have certain functions, such as modulating complement acitvity or binding glycoproteins expressed on rat glomerular epithelial cells and PTEC. Disclosed herein are certain structural requirements for performing the disclosed functions, and it is understood that there are a variety of structures which can perform the same function which are related to the disclosed structures, and that these structures will ultimately achieve the same result, for example stimulation or inhibition complement activity.

E. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Complement Inhibitors Targeted to the Proximal Tubule a) Results

In glomerular diseases of diverse etiologies, dysfunction of the glomerular barrier to protein passage results in proteinuria. There is a link between proteinuria and progressive renal damage, and proteinuria is considered an independent risk factor that plays a direct role in interstitial fibrosis and inflammation. The mechanism by which proteinuria leads to nephrotoxic injury is unclear, but an important role for complement in mediating interstitial damage appears likely (1-5). During glomerular proteinuria, complement proteins are present in the glomerular filtrate, and proximal tubular epithelial cells (PTEC) from both rat and human kidneys activate complement (6, 7). There is also evidence that tubular cells are an important local source of complement, and proteinuric filtrate may contain nephrotic factors that activate tubular cells and upregulate expression of complement proteins (4). Complement activation results in the formation of the C3 convertase, a central enzymatic complex which cleaves C3 leading to the generation of C3 opsonins and C3a. C3 convertase is also involved in the formation of the C5 convertase, an enzymatic complex that cleaves C5 to generate C5a and ultimately C5b-9 or the membrane attack complex (MAC). C3 opsonins, the proinflammatory C3a and C5a peptides and the cytolytic and proinflammatory MAC are variously implicated in pathogenic mechanisms when complement is inappropriately activated.

Under normal circumstances, host cells are effectively protected from complement attack by membrane complement regulators that function by inhibiting either C3 convertase or MAC formation. Human C3 inhibitors are complement receptor 1 (CR1), decay accelerating factor (DAF) and membrane cofactor protein (MCP). Rodents possess an additional C3 inhibitor termed Crry, a structural and functional analogue of the human C3 inhibitors (8). MAC formation is controlled by CD59 in both humans and rodents. Since complement inhibitors display species selective activity, the use of Crry and rodent CD59 in rodent models is necessary.

There is a link between proteinuria and progressive renal damage and there is data to support the hypothesis that proteinuria itself results in interstitial fibrosis and inflammation. The mechanism by which proteinuria leads to nephrotoxic injury is not known, but there is evidence that complement plays a key role and that the MAC is the principal mediator of tubulointerstitial injury (TI) due to proteinuria. The availability of an inhibitor that can specifically block MAC formation would allows an assessment of the role of MAC in tubulointerstitial injury under clinically relevant conditions.

A panel of well characterized mouse anti-rat kidney monoclonal antibodies was used (14, 32, incorporated herein by reference for their teaching regarding these antibodies and their sequences). The variable region DNA from a total of 5 antibodies was isolated by standard PCR techniques (31, incorporated herein by reference for its teachings regarding PCR). All were successfully cloned and some were expressed as single chain antibodies. All single chain antibodies recognized either a rat kidney epithelial or endothelial cell line in vitro. One of the mAbs, K9/9, binds in vivo to an unidentified glycoprotein expressed on rat glomerular epithelial cells and PTEC (14). This antibody was chosen as a targeting vehicle for investigation of targeted Crry- and CD59-mediated complement inhibition in a rat model of acute tubulointerstitial injury. Although the K9/9 mAb was previously shown to induce glomerular damage, the antibody was only pathogenic when administered together with Freunds adjuvant. In fact the pathogenic nature of K9/9 mAb (with adjuvant) was not reproduced.

To generate recombinant targeted complement inhibitors, the extracellular regions of the rat membrane complement inhibitors Crry and CD59 were linked at their amino-termini to a single chain antibody (scFv) targeting moiety derived from K9/9 mAb (FIG. 5). In addition to targeted Crry and CD59 (tCrry, tCD59), soluble untargeted forms of Crry and CD59 (sCrry, sCD59) were also prepared, along with a scFv targeting moiety only (t-vehicle). All recombinant proteins were expressed by *Pichia* fermentation and all purified proteins migrated as a single band of expected molecular weight following SDS-PAGE.

The targeting and complement inhibitory function of recombinant proteins were analyzed in vitro using rat kidney PTEC as target cells. To assess the cell surface binding of the recombinant proteins, the binding of radiolabeled proteins to PTEC was measured. Iodinated tCrry, tCD59 and targeting vehicle all bound PTEC, and scFv specificity was demonstrated by the ability of unlabeled scFv to inhibit binding of labeled proteins (FIG. 1a). To determine functional activity, PTEC were sensitized to complement with a polyclonal antibody and the effect of the recombinant proteins on rat omplementmediated cell lysis (FIGS. 1b and c) and on C3 deposition (FIG. 1d) was measured. tCD59, tCrry and sCrry were equally effective at inhibiting rat complement-mediated lysis of PTEC. Untargeted sCD59 was not effective at inhibiting complement, and this result is consistent with previous data on sCD59 activity (15, 16). If complement inhibitors were removed following incubation with PTEC, but before the addition of rat serum, only tCrry and tCD59 were protective demonstrating that the complement inhibitors were functional when membrane bound. tCrry also inhibited complement activation and C3 deposition on PTEC, and as expected tCD59 had no effect on C3 deposition (FIG. 1d). The scFv targeting vehicle alone had no complement inhibitory activity. Since sCD59 did not effectively inhibit complement in vitro, further in vivo characterization of sCD59 was not pursued.

To determine whether tCrry and tCD59 target to the rat kidney, a biodistribution study was performed using iodinated proteins. Forty eight hours after tail vein injection of radiolabeled tCrry, tCD59 or t-vehicle, a significantly higher proportion of radioactivity (between 45 and 60% infected dose) was localized to the kidney compared to the other organs that were examined (FIGS. 2a and b). The radiolabeled proteins targeted the kidney in both healthy and PAN-treated proteinuric rats (described below) with somewhat higher levels of binding in proteinuric rats, perhaps reflecting increased access to targeting antigen on tubular cells (K9/9 mAb was shown previously to bind glomerular and tubular antigens in vivo (14)). Binding of sCrry in the kidney was not detected. Although a high concentration of targeted complement inhibitors remained in the kidneys at 48 hr relative to other organs, the circulatory half life (t½) of the proteins was short; the t½ in healthy rats for tCrry, tCD59, sCrry and t-vehicle was 38, 33, 34 and 18 minutes, respectively (FIG. 2c). The t½ in proteinuric rats was not significantly different. Both tCrry and sCrry blocked complement activity in sera following injection, but in correlation with their short t½, systemic complement inhibitory activity rapidly declined;

serum complement activity was at 85% of normal by 3-4 hr (7×t½). Negligible systemic activity of sCD59 was also confirmed (FIG. 2d). The short t½ of targeted and untargeted inhibitors, together with biodistribution data and the fact that sCrry is not protective, indicate that the kidney-bound complement inhibitors would be effective at inhibiting complement locally and for a prolonged period.

The recombinant complement inhibitors were investigated therapeutically in a well characterized rat model of non-immunologic proetinuria-associated tubulointerstitial injury. Groups of 4 rats were injected with puromycin (PAN) to induce proteinuria on day 0, followed by intra-peritoneal injection of either PBS, complement inhibitor or targeting vehicle on days 4, 6, 8 and 10 (refer to table 3).

TABLE 3

Treatment groups and resulting proteinuria.

| Group | PAN | Therapy | Urinary protein mg/24 h |
|---|---|---|---|
| I | 150 mg/kg | PBS | 134 ± 16.4 |
| II | 150 mg/kg | t-Vehicle | 150 ± 15.8 |
| III | 150 mg/kg | sCrry | 131 ± 7.5 |
| IV | 150 mg/kg | tCrry | 142 ± 18.0 |
| V | 150 mg/kg | tCD59 | 148 ± 24.0 |
| VI | saline | PBS | 0.56 ± 0.02 |

Urinary protein was determined during 24 h period following therapy and just prior to sacrifice.

Proteinuria appeared prior to the first dose of complement inhibitor (day 4) and the model is thus clinically relevant. Urine was collected over a 24 hr period following the final injection, and on day 11 blood was collected, the rats sacrificed, and the kidneys removed for analysis. Using this protocol, a dose-response study was performed using tCrry and sCrry (FIG. 6). tCrry, but not sCrry, was therapeutically effective at the higher doses tested, and both creatinine clearance and tissue injury score were statistically different ($p<0.05$ comparing treated and control groups).

Based on this data, a larger therapeutic study ($n=4$) was undertaken using all of the recombinant proteins at a dose of 40 mg/kg (Table 3). The results showed that PAN induced heavy proteinuria, and proteinuria appeared before the first dose of complement inhibitor (day 4), verifying that the model is clinically relevant. Also, to address the most clinically relevant situation, individual inhibitors were administered rather than the two combined at a time when proteinuria was evident. There was no significant difference in urinary protein levels between the treatment groups after the final therapeutic injection (Table 3), and PAN treatment significantly impaired renal function as measured by creatinine clearance. In proteinuric rats, relative creatinine clearance was 40% of normal, and clearance was not significantly improved with sCrry treatment (FIG. 3C). In contrast, creatinine clearance in proteinuric rats receiving either tCrry or tCD59 was significantly improved and was 89 and 84% of normal, respectively ($p<0.01$). Both tCrry and tCD59 individually provided a level of protection that was not statistically different from injury seen in the control group (rats not receiving puromycin). Targeting vehicle alone had no effect on creatinine clearance. Histological examination of kidney sections prepared from rats treated with PAN and receiving no therapy revealed dilation of tubular lumina and tubular and epithelial cell degeneration as assessed by loss of brush border (FIGS. 3A and B). Minimal improvement was seen with sCrry therapy. However, tubular dilation and degeneration was significantly and similarly suppressed in proteinuric rats receiving either tCrry or tCD59 (FIGS. 3A and B). Creatinine clearances were not measured nor survival renal biopsies performed to assess tubular injury scores before administration of targeted inhibitors, but it is understood that these measurements are expected to be relatively normal at this time even though proteinuria was present. The data showed that the observed pathophysiological effects seen in control treated proteinuric animals were prevented.

To investigate the functional consequence of the complement inhibitors in vivo, C3 and MAC deposition were examined on proximal tubules from rats in the different treatment groups. Proximal tubules of proteinuric rats that received no therapy stained strongly positive for both C3 and MAC (C9) (FIG. 4, A and B). C3 and C9 staining was apparent within the tubular cells. Tubular cells are metabolically active, and the apparent cytosolic location of C3 and C9 is likely a result of endocytosis of membrane fixed complement. In this regard, analysis of C3 and C9 deposition was performed on tissue sections prepared from kidneys removed 11 days after PAN treatment, or ~7 days after onset of proteinuria and initial complement deposition at the tubular surface. In contrast to untreated proteinuric rats, rats receiving tCrry therapy had markedly reduced levels of both C3 and MAC deposition. tCD59 therapy, in contrast, reduced MAC but not C3 deposition. Untargeted sCrry had a minimal effect on C3 and MAC deposition. Thus, the measured parameters of tubulointerstitial injury after therapy correlated with MAC deposition, but not C3 deposition, on proximal tubules. Together, the data demonstrate that the MAC is the primary mediator of tissue injury in this model and that neither C3 opsonins, nor C3a, nor C5a make significant contributions to pathogenesis. Tubular binding of the targeted complement inhibitors was confirmed by immunofluorescence (FIG. 4C). Targeting vehicle alone gave a binding pattern similar to those of the targeted complement inhibitors. Neutrophil infiltration was also examined, but there was no difference between the different treatment groups (as determined on day 11 by immunohistochemistry and myeloperoxidase determinations).

Both tCrry and sCrry blocked complement activity in sera after i.p. injection at 40 mg/kg (route and dose used in therapeutic studies). However, in correlation with their short t½ after tail vein injection (see above), systemic complement-inhibitory activity rapidly declined; serum complement activity was at 85% of normal by 3-4 h (7×t½). Negligible systemic activity of sCD59 was also confirmed (FIG. 2D). The short t½ of targeted and untargeted inhibitors, together with biodistribution data and the fact that sCrry is not protective, indicate that the kidney-bound complement inhibitors are effective at inhibiting complement locally and for a prolonged period. Furthermore, 24 h after the final injection of inhibitor or PBS, there was no difference in serum complement activity between healthy control mice and proteinuric mice treated with either PBS or the different inhibitors. Thus, neither ongoing disease nor inhibitor treatment affected serum complement levels (determined by hemolytic assay).

Together the data demonstrate that the MAC is the primary mediator of tissue injury and that neither C3 opsonins, C3a nor C5a make significant contributions to pathogenesis. Soluble untargeted CD59 did not effectively inhibit complement, and to function effectively CD59 must be bound at the site of MAC formation. This functional constraint on CD59 has been shown in vitro (15, 16) and more recently in vivo by the demonstration that a membrane inserting form of CD59 when injected intra-articularly ameliorated disease in a model of rheumatoid arthritis (18). However, this study represents the first demonstration of effective and specific MAC inhibition in vivo following the systemic administration of inhibitor, and has important implications for proteinuric disorders and other disease conditions in which the MAC has a major pathogenic role; a CD59-based inhibitor will not interfere with the generation of the complement activation products that are important in normal physiological processes (9, 12, 13).

Specific targeting of systemically administered CD59 provides the means to investigate the pathologic role of the MAC in various complement-dependent diseases under clinically relevant conditions. In this context, complement deficient animals have provided for a much better understanding of complement-associated disease mechanisms, but the data can be at odds with results obtained from studies in which complement has been temporarily inhibited. Complement deficiency may influence development of other immune functions, with the possible modulation of compensatory pathways. Also, there is likely to be some remaining functionality following the administration of a complement inhibitor and this may have a bearing on therapeutic outcome, since complement can have both protective and injurious effects during disease. Since most patients will have normal or only partially depleted complement levels, the availability of complement inhibitors that can be targeted to a site of disease and that can inhibit complement at different points in the pathway, provides a clinically relevant means to study the role of complement in experimental disease.

For complement-dependent disease processes involving early complement activation fragments, the targeting of C3 (and potentially C5) inhibitors offers advantages of improved efficacy and of safety due to low levels of systemic inhibition. A short circulatory half life of a targeted complement inhibitor (as was the case with the constructs used here) may be advantageous, and effective therapy was achieved in this model with very low levels of systemic inhibition. The C3 inhibitor sCR1 has shown therapeutic benefit in a variety of animal models of disease, and therapeutically effective doses maintain systemic inhibition for >24 hr (19). A sialyl Lewisx (sLex) glycosylated form of sCR1 has been shown to bind selectins in vitro, albeit with low affinity, and to localize to the vasculature in some models of inflammatory disease (20-22). However sLex sCR1 and sCR1 have similar pharamocokinetics and serum inhibitory activity (23) and therapeutically effective doses maintain systemic inhibition. Recently, in vivo targeting of human DAF to sites of C3 deposition and to erythrocytes have been demonstrated in mice using a soluble complement receptor 2 (CR2) (16) and an antibody fragment (24) respectively, but without functional characterization of activity in vivo.

With regard to the current study, the glomerulus is an effective barrier preventing the passage of protein into the nearly 170 liters of ultrafiltrate formed daily in humans. This restriction occurs in a size-selective manner. Since almost all proteins of the complement activation cascade are large (MW ~200 kDa), few of these proteins will appear in this ultrafiltrate and reach tubular lumina under normal circumstances. As such, the apical aspects of tubules are not endowed with significant quantities of proteins that regulate the cleavage of C3/C5 or the formation of C5b-9 (6, 7, 25). Consistent with this, complement can be spontaneously activated on tubular cells in vitro (6, 7). In any disease in which the glomerular barrier to protein passage is disrupted, complement proteins can appear in the tubular fluid and lead to complement activation. Such complement activation can occur in any condition accompanied by proteinuria, including immunological diseases as well as those not considered to have an immunological basis, such as the common disease diabetic nephropathy. The current data establish the benefits of targeted complement inhibition with regard to both efficacy and safety.

b) Materials and Methods (1) Animals, Cells, and Reagents

Normal rat serum was obtained from Cocalico Biologicals, and C6-deficient rat serum was a gift from Dr. W. M. Baldwin (Johns Hopkins University School of Medicine, Baltimore, Md.). Monoclonal mouse anti-rat Crry, 5I2 (36), and monoclonal mouse anti-rat CD59, 6D1 (37), are described. Antiserum against rat C9 that recognizes MAC in rat tissue was a gift from Dr. Paul Morgan (Univeristy of Wales, Cardiff, U.K.). Anti-rat C3 serum was from MP Biomedicals. Rabbit antiserum to rat Crry, human CD59 (cross-reactive with rat CD59), and K9/9 single-chain Fv (scFv) were prepared by Cocalico Biologicals. All secondary Abs were purchased from Sigma-Aldrich. Female Sprague-Dawley rats weighing 45-50 g were purchased from Harlan and were housed with free access to food and water. Experimental protocols were conducted according to current guidelines presented in the National Institute of Health Guide for the care and use of laboratory animals. The rat proximal tubule epithelial cell (PTEC) line was obtained from American Type Culture Collection and cultured in DMEM with 10% FCS.

(2) Recombinant DNA Techniques

For the cloning of Ab variable region cDNA, total RNA was extracted from the hybridoma cell line expressing K9/9 mAb (14) using an RNA Extract Kit (Qiagen). Variable region cDNAs (VL and VH chains) were amplified by RT-PCR. The 5'- and 3'-primers used for VL chain were ATGAAGTTGC-CTGTTAGGCTGTTGGTGCTG (SEQ ID NO: 16) and ACTGGATGGTGGGAAGATGG (SEQ ID NO: 17). The 5'- and 3'-primers used for VH chain were ATGAAATG-CAGCTGGGGCATGTTCTTC (SEQ ID NO: 18) and CAGTGGATAGACCGATGGGCC (SEQ ID NO: 19). PCR fragments were subcloned into TA cloning vector (Invitrogen) and VL and VH chains joined by a (G4S)3 linker. For construction of targeted complement inhibitors, the K9/9 targeting scFv was linked to cDNA encoding an extracellular domain of rat Crry (five N-terminal short consensus repeats, residues 1-981) (36) or mature rat CD59 (residues 1-77) (38). scFv and complement inhibitors were joined by a G4S linker in the sequence VL-VH inhibitor by standard PCR techniques. cDNA was cloned into pPICZα *Pichia pastoris* expression plasmid (Invitrogen). All sequences were verified.

(3) Expression and Purification of Recombinant proteins

*P. pastoris* strain X-33 was used for expression of recombinant proteins. After transformation, positive clones were selected by PCR, and protein expression was verified by Western blot. Yeast was grown in a 7-liter fermentor (New Brunswick Scientific), and recombinant proteins were purified from culture supernatants by standard bulk anion exchange separation followed by Q Sepharose and Mono Q FPLC (Amershan Biosciences). Protein concentration was determined by bicinchoninic acid assay (Pierce Chemical), and purified proteins were analyzed by SDS-PAGE and Western blotting.

(4) In Vitro Analysis of Binding

Recombinant proteins were iodinated using the iodogen method according to manufacturer's instructions (Pierce Chemical) to approximate specific activities of $1 \times 10^7$ cpm/μg and incubated with PTEC in the absence or presence of 100-fold excess of unlabeled proteins. The recombinant proteins (0.1 mg/ml) were added to a monolayer of PTEC (80% confluent in 24-well plates) for 30 min at 4° C. Cells were then washed with 1% BSA in culture medium and treated with 0.5 M NaOH to remove bound protein; then radioactivity in the supernatant was determined.

(5) In Vitro Complement Lysis and C3 Deposition Assays

Rat PTEC at 60-80% confluency were detached with 0.05 M EDTA in PBS, washed twice, and resuspended to $1 \times 10^6$/ml in DMEM. Cells were then sensitized to complement by incubation (4° C. for 30 min) in 10% rabbit antiserum raised against rat 13762 mammary adenocarcinoma cells (39). After incubation, an equal volume of rat serum diluted in DMEM was added, and cell viability was determined after 45 min at 37° C. using the CytoTox 96 Non-Radioactive Cytotoxicity Assay Kit (Promega). Cell lysis assays were typically performed in 96-well ELISA plates in a final volume of 100 μl. To determine the effect of complement inhibitors on complement-mediated lysis, the recombinant proteins in PBS were added after Ab sensitization, and incubations were continued for a further 30 min at 4° C. before addition of rat serum. In some experiments, cells were washed twice with DMEM before addition of rat serum. Percentage of inhibition of lysis was calculated as (A−B)/A, where A=percentage of cell lysis in 10% normal rat serum and B=percentage of cell lysis in 10% normal rat serum with recombinant protein. The effect of the complement-inhibitory proteins on C3 deposition was determined by flow cytometry. For flow cytometry, the procedure described above for cell lysis determinations was followed except that 10% C6-deficient rat serum was used in place of normal rat serum. After incubation in serum, the cells were washed, and C3 deposition was detected by means of anti-rat C3 Ab-FITC by standard procedures (40).

(6) In Vivo Blood Clearance and Biodistribution of Radiolabeled Recombinant Proteins For determination of rate of clearance from the circulation, iodinated recombinant proteins ($1 \times 10^8$ cpm) were injected into the tail vein; blood was collected at 30 min, 1 h, 2 h, 4 h, and 8 h after injection; and radioactivity in blood was counted. Circulatory half-life (t½) was calculated by standard methods (41). Biodistribution studies were performed using standard procedures for determining tissue distribution of injected radiolabeled proteins (41, 33). Briefly, $1 \times 10^8$ cpm of $^{125}$I-labeled soluble Crry (sCrry; $1.2 \times 10^7$ cpM/μg), targeted Crry (tCrry) ($1.3 \times 10^7$ cpm/μg), targeted CD59 (tCD59; $1.2 \times 10^7$ cpm/μg), or targeting vehicle only (t-vehicle) ($1.0 \times 10^7$ cpm/μg) were injected into the tail vein of 40- to 55-g female rats. After 48 h, a blood sample was taken, and major organs were removed, shredded, washed in PBS containing 10 mM EDTA, weighed, and counted. Targeting specificity was determined as percentage of cpm per gram of tissue divided by total injected cpm per gram of body weight. Percentage=A/B×100, where A=tissue cpm per gram of tissue weight and B=total cpm per gram of body weight. All animal studies were approved by the Institutional Animal Care and Use Committee institutional review board at Medical University of South Carolina.

(7) Serum Complement—Inhibitory Activity

Ab-sensitized sheep erythrocytes ($1 \times 10^7$; Advanced Research Technologies) were incubated in serum dilutions in a final volume of 300 μl at 37° C. for 1 h. Gelatin-veronal buffer-EDTA (Sigma-Aldrich) was then added, and hemolysis was determined by measuring OD414 of supernatants (42). Total complement hemolytic activity (CH50) was defined as the reciprocal of the dilution of serum that lysed 50% of the erythrocytes; this measurement was used to compare serum complement activity. After i.p. injection of recombinant complement inhibitors (40 mg/kg), serum was collected at different times and percentage of complement inhibitory activity in sera was defined as the difference between CH50 of normal serum and CH50 of sample divided by CH50 of normal serum.

(8) Rat Model of Puromycin Aminonucleoside-Induced Nephrosis and Experimental Protocol Proteinuria-induced tubulointerstitial injury was induced in female Sprague-Dawley rats (Harlan) weighing 45-50 g by single tail vein injection of 150 mg/kg puromycin aminonucleoside (PAN). Proteinuria develops by day 4. In a dose-response pilot study, 20 rats were divided into 10 groups of 2 animals. Nine groups received PAN, and a control group received saline. On days 4, 6, 8, and 10, control rats received an i.p. injection of PBS, and each group of PAN-treated rats received i.p. injections of varying doses (5-40 mg/kg) of sCrry or tCrry. After the final injection, rats were placed in metabolic cages, and urine was collected for 24 h. On day 11, blood was collected, rats were sacrificed, and kidneys were removed. In a larger therapeutic study, 24 rats were divided into 6 groups of 4 animals. Five groups received PAN, and a control group received saline. Control rats received i.p. injections of PBS, and PAN-treated rats received i.p. injections of PBS, sCrry, tCrry, tCD59, or targeting vehicle only (Table 3) at 40 mg/kg using the same protocol described above for pilot study.

(9) Renal Function and Histology

Urinary protein was measured using a bicinchoninic acid protein assay kit (Pierce). Creatinine clearance, a measure of renal function, was calculated after the measurement of rat serum and urine creatinine with a creatinine regent kit (Roche Pharmaceuticals) according to manufacturer's instructions. For histological assessment of tubulointerstitial injury, paraffin-embedded kidney sections were stained with periodic acid-Schiff reagent, and tubulointerstitial injury was assessed in a blinded manner. Tubulointerstitial injury is defined as tubular dilation, tubular atrophy, tubular cast formation, sloughing of tubular epithelial cells, or thickening of the tubular basement membrane and was scored on a scale of 0-4, as follows: 0, no injury; 1, <25% of the tubulointerstitium injured; 2: 25-50% of the tubulointerstitium injured; 3, 51-75% of the tubulointerstitium injured; 4: >75% of the tubulointerstitium injured.

(10) Immunofluorescence Microscopy

To investigate C3 and MAC deposition, frozen kidney sections were stained with anti-rat C3 or anti-rat C9 antiserum together with appropriate FITC-labeled secondary Abs as described (16). The binding of targeted complement inhibitors in the kidney was similarly analyzed using rabbit antiserum raised against K9/9 scFv. Digital images were acquired and optimized with Adobe Photoshop using identical settings. Neutrophil infiltration was also assessed by immunofluorescence microscopy using polymorphonuclear leukocyte-specific mouse anti-rat granulocyte mAb (BD Biosciences) and by measuring myeloperoxidase activity in kidney tissue samples as described (43).

(11) Statistics

Data are presented as mean±SD. Data were analyzed by global ANOVA followed by the post hoc test (Scheffé's procedure). For dose-response experiments, group comparisons were done with the Kruskal-Wallis test.

2. Example 2

Model Complement Activation in Proteinuric Disease

The following events of complement activation occurring from the fluid phase are relevant to what occurs in vivo on the PTEC. The initial alternative pathway C3 convertase requires factor D to cleave factor B present in a trimolecular complex containing hydrolyzed C3 (C3($H_2O$)), factor B, and $Mg^{++}$. The resulting C3($H_2O$)Bb can recruit and cleave native C3 to generate alternative pathway C3 and C5 convertases, C3bBb and C3bBbC3b, respectively. This whole process can occur spontaneously because factor D is an active serine esterase (unlike most others that exist as zymogens) while the formation of C3($H_2O$) is continuous, and can be accelerated by conditions present in tubular fluid, such as exposure to ammonia and acidic pH (28, 51, 57). The generation of C5b-9 can proceed simply when its composite proteins are present in the vicinity. Besides the constraints of component availability, and time and space (that is, the proteins must find each other and a receptive surface prior to spontaneous inactivation, which varies depending on the intermediate), there are competing influences of compelent regulatory proteins, including DAF, MCP, CR1, and clusterin, protein S and CD59 for C5b-9. The balance between pro- and anti-activating influences in normal tubular fluid is unfavorable for alternative pathway activation. However, this shifts towards activation in proteinuric conditions, leading to C5b-9 generation, which over time results in tubulointerstitial injury pathology. The explanation for this is that C3 and C5, which are key for this activation to occur are large (185-190 kDa) which leads to their being restricted from normal but not abnormal glomerular ultrafiltrate; based upon previously discussed models, $1_{C3/C5}$ can be estimated as 0.0005 in controls and 0.0125 in nephrotics (45), reflecting in a 50-fold increase in their appearance into tubular fluid (which would be 20 and 1 mg/L for C3 and C5, respectively). Other aspects include local PTEC production of complement components and CRPs under disease conditions (49, 8-60).

These studies can be performed with cPTEC, in which PTEC is exposed to various concentrations of normal human serum (a stock of pooled serum from several normal laboratory donors). To confirm that the observed effects are due to alternative pathway-mediated C5b-9 formation, controls can include heat-inactivated serum, serum in $Mg^{++}$-EGTA to allow only alternative pathway activation, and serum lacking specific complement components. Complement activation is reflected by cell injury as indicated by release from intracellular pools of previously cell-loaded with 2',7'-bis-(carboxyethyl)-5(6)-carboxyfluorescein (BCECF) and the intrinsic cellular enzyme, LDH. Release of the former but not the latter is typical of so-called sublytic cell damage and seems most relevant to complement activation in disease states (54, 61, 62). In addition, the quantities of C3b and C5b-9 on cell membranes can be evaluated by western blotting using mAbs specific for the iC3b chain of cleaved C3 and for neoantigens on C5b-9 (50, 63).

Also of interest is the phenotypic response of the PTEC model system to sublytic complement activation. mRNA for inflammatory mediators known to be produced by PTEC can be examined, including upon complement activation and/or exposure to excess concentrations of proteins (such as albumin), which are likely to be relevant to human proteinuric diseases (48, 64, 65). These can include CRPs (to evaluate whether PTECs respond "defensively" to complement activation as other cells do (66) and as appears to occur in vivo (49)), anaphylatoxin receptors (55, 56), complement proteins (C3, factor B), cytokines (IL-1 and IL-6) and chemokines (CCL2, CCL5 and $CX_3CL1$). In addition, potential activation of phospholipases, protein kinase C, and NF-κB can be assessed as relevant to complement activation and/or PTEC stress (48, 67).

3. Example 3 mAbs to PTEC Antigens

It is disclosed herein that PTEC antigens facilitate targeted delivery of CD59 providing protection against the spontaneous formation of C5b-9. In studies, CD59 has been functionally active to prevent C5b-9 generation on cells when targeted to dansyl (15), C3 (16) and DPPIV (44) on the surface of cells. The latter is an intrinsic membrane protein of the PTEC, and it was fortuitous the mAb clone selected (K9/9) was effective. DPPIV and iC3b/C3d can be used as targets for mAbs and CR2, respectively. Other potential target antigens include at least 18 members of the solute carrier superfamily present in the PTEC brush border (from Slc1a1 to Slc34a1; see list above), other transporters such as water and chloride channels, and members of the ATP binding cassette family (Abcb1b, Abcc2 and 4). The previously discussed proteins megalin, NEP, and KIM-1, as well as Mucin 20 (MUC20) (68, 69) are also potential target antigens. As noted above, the advantages of these molecules are that they have high expression in the apical membrane of the PTEC, their protein structure is known, and in the case of the latter two they are highly expressed in states in which the PTEC is injured (52, 53, 68). In addition, mAbs are available for KIM-1 which can be exploited.

Megalin and MUC20 each are type I transmembrane proteins, with relatively extended extracellular domains (68-70). mAbs can be raised against recombinant proteins containing defined extracellular regions of megalin and MUC20 fused to C terminal human 1 Fc domains and produced in CHO cells. A MUC20 recombinant is created containing 4-6 mucin repeats using a PCR strategy with the 5' primer upstream from the repeating region and the 3' primer ending just outside the transmembrane domain at L202 (68). For megalin, a similar approach is taken to produce a recombinant containing amino acids 4330-4420, which encompasses EGF-like domains 16 and 17 of this protein, 7 predicted disulfide bonds within this fragment (and none extending outside of it), excludes a potential glycosylation site at N4327, and terminates just before the transmembrane domain.

DPPIV and NEP are type II transmembrane proteins also with large extracellular domains but more complicated tertiary structures than megalin, MUC20 or KIM-1. Although soluble recombinants containing the entire extracellular domains of each that retained activity and structure have been produced using standard methodology (71, 72), α-helical regions modeled to be close to the membrane are of interest.

In the case of DPPIV, these are all contained in the α/β hydrolase domain (extending from Q508 to the C-terminal P766) in the final five β propellers (71, 73), while in NEP, they are contained in the larger catalytic domain (72). The peptides are listed below, and are utilized to raise mAbs using standard multiple antigenic peptide (MAP) technology (74).

| NEP | | | DPPIV | | |
|---|---|---|---|---|---|
| AAs | Peptide | | AAs | Peptide | |
| 59-71 | SDCIKSAARLIQN | (SEQ ID NO: 20) | 601-614 | FEVEDQIEAARQFS | (SEQ ID NO: 21) |
| 82-93 | FFKYACGGWLKR | (SEQ ID NO: 22) | 631-640 | YGGYVTSMVL | (SEQ ID NO: 23) |
| 435-456 | SKHVVEDLIAQIREVFIQTLDD | (SEQ ID NO: 24) | 713-726 | FQQSAQISKALVDV | (SEQ ID NO: 25) |
| 462-474 | AETKKRAEEKALA | (SEQ ID NO: 26) | 745-763 | STAHQHIYTHMSHFIKQCF | (SEQ ID NO: 27) | mAbs are raised in mice using standard techniques. Four mice each for megalin, MUC20, DPPIV and NEP are immunized and those making high titer antibodies boosted and used for hybridoma production. Screening for mAbs at each step is done by ELISA using the immunogens. In addition, the ability to bind native protein on PTECs in culture (using a high throughput in situ fluorescence assay) and in normal kidney tissue (by standard indirect immunofluorescence microscopy) can be assessed. These latter abilitites can be used as guides to selection of hybridoma clones.

4. Example 4 mAb/CR2-CD59 Chimeras to Target Human PTECs

Herein disclosed are several scFv-CD59 proteins each for megalin, MUC20, DPPIV, NEP, and KIM-1. These will bind to their respective proteins on the PTEC surface. In addition, CR2-CD59 can be constructed to bind C3 fragments on PTEC. By virtue of their localization to epitopes close to the plasma membrane, the CD59 in scFv-CD59 (or CR2-CD59) limit C5b-9 generation occurring on PTECs from fluid phase complement activation.

cDNA encoding the variable light and heavy chain domains from hybridomas producing mAbs against the selected PTEC antigens (DPPIV, NEP, Megalin, KIM-1 and MUC20) is isolated and the sequences used to construct plasmids encoding scFvs by standard techniques (75, 76). The scFvs are prepared as His-tagged constructs for ease of purification and in vitro characterization of scFv binding to cultured PTECS. scFv binding to cultured PTECs is quantified using FITC-conjugated anti-His-tag antibodies. Standard controls are used to confirm the specificity of binding in these in situ assays. As with scFv's alone, the scFv-CD59 proteins are tested for their ability to bind their respective PTEC antigens in culture and in kidney tissue. Western blotting is performed to evaluate specificity of protein binding.

5. Example 5

Disclosed herein are examples of constructs of the present invention made in accordance with the teaching herein. The terminology used has the following meaning: SCR=short consensus repeats; LP=Leader Peptide. The constructs all have the basic formula of K9/9-linker-complement modulator. Notations in parenthesis indicate details within a particular section of the composition. It is understood that a linker can be a chemical linker, a natural linker peptide, or amino acid linking sequences (e.g., $(Gly_4Ser)_2$). It is understood that this list is not limiting and only provides examples of some of the constructs disclosed in the present application.

K9/9-$(Gly_4Ser)_2$--DAF
K9/9-$(Gly_4Ser)_2$-human CD59
K9/9-$(Gly_4Ser)_2$--MCP
K9/9-$(Gly_4Ser)_2$-CR1
K9/9-$(Gly_4Ser)_2$---Crry
K9/9-$(Gly_4Ser)_2$-mouse CD59
K9/9-$(Gly_4Ser)_2$-human IgG1 Fc
K9/9-$(Gly_4Ser)_2$-human IgM Fc
K9/9-$(Gly_4Ser)_2$-murine IgG3 Fc
K9/9-$Gly_4Ser)_2$-murine IgM Fc
K9/9-$(Gly_4Ser)_2$-CVF
K9/9-$(Gly_4Ser)_3$--DAF
K9/9-$(Gly_4Ser)_3$-human CD59
K9/9-$(Gly_4Ser)_3$--MCP
K9/9-$(Gly_4Ser)_3$-CR1
K9/9-$(Gly_4Ser)_3$--Crry
K9/9-$(Gly_4Ser)_3$-mouse CD59
K9/9-$(Gly_4Ser)_3$-human IgG1 Fc
K9/9-$(Gly_4Ser)_3$-human IgM Fc
K9/9-$(Gly_4Ser)_3$-murine IgG3 Fc
K9/9-$(Gly_4Ser)_3$-murine IgM Fc
K9/9-$(Gly_4Ser)_3$--CVF
K9/9-$(Gly_3Ser)_4$--DAF
K9/9-$(Gly_3Ser)_4$-human CD59
K9/9-$(Gly_3Ser)_4$--MCP
K9/9-$(Gly_3Ser)_4$-CR1
K9/9-$(Gly_3Ser)_4$--Crry
K9/9-$(Gly_3Ser)_4$-mouse CD59
K9/9-$(Gly_3Ser)_4$-human IgG1 Fc
K9/9-$(Gly_3Ser)_4$-human IgM Fc
K9/9-$(Gly_3Ser)_4$-murine IgG3 Fc
K9/9-$(Gly_3Ser)_4$-murine IgM Fc
K9/9-$(Gly_3Ser)_4$-CVF
K9/9-$(Gly_4Ser)_3$-DAF (SCRs 2-4)
K9/9-$(Gly_3Ser)_4$-DAF (SCRs 2-4)
K9/9-$(Gly_4Ser)_3$-CR1 (LP--SCR1-4-SCR8-11-SCR15-18)
K9/9-$(Gly_4Ser)_3$-Crry (5 N-terminal SCRS)
DPPIV-$(Gly_4Ser)_3$--DAF
DPPIV-$(Gly_4Ser)_3$-human CD59
DPPIV-$(Gly_4Ser)_3$--MCP
DPPIV-$(Gly_4Ser)_3$-CR1
DPPIV-$(Gly_4Ser)_3$--Crry
DPPIV-$(Gly_4Ser)_3$-mouse CD59
DPPIV-$(Gly_4Ser)_3$-human IgG1 Fc
DPPIV-$(Gly_4Ser)_3$-human IgM Fc
DPPIV-$(Gly_4Ser)_3$-murine IgG3 Fc
DPPIV-$(Gly_4Ser)_3$-murine IgM Fc
DPPIV-$(Gly_4Ser)_3$--CVF Kim-1-$(Gly_4Ser)_3$--DAF
Kim-1-$(Gly_4Ser)_3$-human CD59
Kim-1-$(Gly_4Ser)_3$--MCP
Kim-1-$(Gly_4Ser)_3$-CR1
Kim-1-$(Gly_4Ser)_3$--Crry
Kim-1-$(Gly_4Ser)_3$-mouse CD59
Kim-1-$(Gly_4Ser)_3$-human IgG1 Fc
Kim-1-$(Gly_4Ser)_3$-human IgM Fc
Kim-1-$(Gly_4Ser)_3$-murine IgG3 Fc
Kim-1-$(Gly_4Ser)_3$-murine IgM Fc
Kim-1-$(Gly_4Ser)_3$--CVF
NED-$(Gly_4Ser)_3$--DAF
NED-$(Gly_4Ser)_3$-human CD59
NED-$(Gly_4Ser)_3$--MCP
NED-$(Gly_4Ser)_3$-CR1
NED-$(Gly_4Ser)_3$--Crry
NED-$(Gly_4Ser)_3$-mouse CD59
NED-$(Gly_4Ser)_3$-human IgG1 Fc
NED-$(Gly_4Ser)_3$-human IgM Fc
NED-$(Gly_4Ser)_3$-murine IgG3 Fc
NED-$(Gly_4Ser)_3$-murine IgM Fc
NED-$(Gly_4Ser)_3$--CVF
K9/9-VSVFPLE--DAF
K9/9-VSVFPLE-human CD59
K9/9-VSVFPLE--MCP
K9/9-VSVFPLE-CR1
K9/9-VSVFPLE-Crry
K9/9-VSVFPLE-mouse CD59
K9/9-VSVFPLE-human IgG1 Fc
K9/9-VSVFPLE-human IgM Fc
K9/9-VSVFPLE-murine IgG3 Fc
K9/9-VSVFPLE-murine IgM Fc
K9/9-VSVFPLE-CVF
DPPIV-VSVFPLE--DAF
DPPIV-VSVFPLE-human CD59
DPPIV-VSVFPLE--MCP
DPPIV-VSVFPLE-CR1
DPPIV-VSVFPLE-Crry
DPPIV-VSVFPLE-mouse CD59
DPPIV-VSVFPLE-human IgG1 Fc
DPPIV-VSVFPLE-human IgM Fc
DPPIV-VSVFPLE-murine IgG3 Fc
DPPIV-VSVFPLE-murine IgM Fc
DPPIV-VSVFPLE-CVF
K9/9---m-Maleimidobenzoyl-N-hydoxysuccinimide ester--DAF
K9/9---m-Maleimidobenzoyl-N-hydoxysuccinimide ester-human CD59
K9/9-m-Maleimidobenzoyl-N-hydoxysuccinimide ester--MCP
K9/9-m-Maleimidobenzoyl-N-hydoxysuccinimide ester-CR1
K9/9-m-Maleimidobenzoyl-N-hydoxysuccinimide ester--Crry
K9/9-m-Maleimidobenzoyl-N-hydoxysuccinimide ester-mouse CD59
K9/9-m-Maleimidobenzoyl-N-hydoxysuccinimide ester-human IgG1 Fc
K9/9-m-Maleimidobenzoyl-N-hydoxysuccinimide ester-human IgM Fe
K9/9-m-Maleimidobenzoyl-N-hydoxysuccinimide ester-murine IgG3 Fc
K9/9-m-Maleimidobenzoyl-N-hydoxysuccinimide ester-murine IgM Fc
K9/9-m-Maleimidobenzoyl-N-hydoxysuccinimide ester-CVF
DPPIV---m-Maleimidobenzoyl-N-hydoxysuccinimide ester--DAF
DPPIV---m-Maleimidobenzoyl-N-hydoxysuccinimide ester-human CDS9
DPPIV---m-Maleimidobenzoyl-N-hydoxysuccinimide ester--MCP
DPPIV-m-Maleimidobenzoyl-N-hydoxysuccinimide ester-CR1
DPPIV-m-Maleimidobenzoyl-N-hydoxysuccinimide ester--Crry
DPPIV-m-Maleimidobenzoyl-N-hydoxysuccinimide ester-mouse CD59
DPPIV-m-Maleimidobenzoyl-N-hydoxysuccinimide ester-human IgG1 Fc
DPPIV-m-Maleimidobenzoyl-N-hydoxysuccinimide ester-human IgM Fe
DPPIV-m-Maleimidobenzoyl-N-hydoxysuccinimide ester-murine IgG3 Fc
DPPIV-m-Maleimidobenzoyl-N-hydoxysuccinimide ester-murine IgM Fc
DPPIV-m-Maleimidobenzoyl-N-hydoxysuccinimide ester-CVF
K9/9-bismaleimidohexane-DAF
K9/9-bismaleimidohexane-human CD59
K9/9-bismaleimidohexane--MCP
K9/9-bismaleimidohexane-CR1
K9/9-bismaleimidohexane--Crry
K9/9-bismaleimidohexane-mouse CD59
K9/9-bismaleimidohexane-human IgG1 Fc
K9/9-bismaleimidohexane-human IgM Fc
K9/9-bismaleimidohexane-murine IgG3 Fc
K9/9-bismaleimidohexane-murine IgM Fc
K9/9-bismaleimidohexane-CVF
DPPIV-bismaleimidohexane--DAF
DPPIV-bismaleimidohexane-human CD59
DPPIV-bismaleimidohexane--MCP
DPPIV-bismaleimidohexane-CR1
DPPIV-bismaleimidohexane--Crry
DPPIV-bismaleimidohexane-mouse CD59
DPPIV-bismaleimidohexane-human IgG1 Fc
DPPIV-bismaleimidohexane-human IgM Fc
DPPIV-bismaleimidohexane-murine IgG3 Fc
DPPIV-bismaleimidohexane-murine IgM Fc
DPPIV-bismaleimidohexane-CVF F. References 1. A. Nomura et al., *Am J Pathol* 151, 539-47 (August, 1997).
2. Y. Hori et al., *Kidney Int* 56, 2096-106 (December, 1999).
3. M. Nangaku, J. Pippin, W. G. Couser, *J Am Soc Nephrol* 13, 928-36 (April, 2002).
4. S. Tang, K. N. Lai, S. H. Sacks, *Kidney Blood Press Res* 25, 120-6 (2002).
5. S. I. Hsu, W. G. Couser, *J Am Soc Nephrol* 14, S186-91 (July, 2003).
6. G. Camussi, M. Rotunno, G. Segoloni, J. R. Brentjens, G. A. Andres, *J Immunol* 128, 1659-63 (April, 1982).
7. L. Biancone et al., *Kidney Int* 45, 451-60 (February, 1994).
8. Y. U. Kim et al., *Journal of Experimental Medicine* 181, 151-159 (1995).
9. J. D. Lambris, V. M. Holers, Eds., *Therapeutic interventions in the complement system* (Humana Press, Totowa, N.J., 2000).
10. R. J. Quigg, *Trends Mol Med* 8, 430-6 (September, 2002).
11. W. G. Couser, *J Am Soc Nephrol* 14, 815-8 (March, 2003).
12. C. L. Harris, D. A. Fraser, B. P. Morgan, *Biochem Soc Trans* 30, 1019-26 (November, 2002).
13. M. J. Walport, *Arthritis Res* 4 Suppl 3, S279-93 (2002).

14. D. L. Mendrick, H. G. Rennke, *Kidney Int* 33, 818-30. (1988).
15. H.-F. Zhang, J. Yu, E. Bajwa, S. L. Morrison, S. Tomlinson, *J. Clin. Invest.* 103, 55-66 (1999).
16. H. Song et al., *J Clin Invest* 111, 1875-85 (June, 2003).
17. C. Whiteside, K. Prutis, R. Cameron, J. Thompson, *Lab Invest* 61, 650-60 (December, 1989).
18. D. A. Fraser et al., *J Biol Chem* 278, 48921-7 (Dec. 5, 2003).
19. S. J. Piddlesden et al., *J. Immunol.* 152, 5477-5484 (1994).
20. J. Huang et al., *Science* 285, 595-9 (Jul. 23, 1999).
21. M. S. Mulligan et al., *J Immunol* 162, 4952-9 (Apr. 15, 1999).
22. C. Kyriakides et al., *Am J Physiol Cell Physiol* 281, C224-30 (July, 2001).
23. K. Zacharowski, M. Otto, G. Hafner, H. C. Marsh, Jr., C. Thiemermann, *Br J Pharmacol* 128, 945-52 (November, 1999).
24. D. Spitzer, J. Unsinger, M. Bessler, J. P. Atkinson, *Mol Immunol* 40, 911-9 (February, 2004).
25. S. Ichida, Y. Yuzawa, H. Okada, K. Yoshioka, S. Matsuo, *Kidney Int* 46, 89-96. (1994).
26. G. Camussi et al., *Clin Nephrol* 23, 134-41 (March, 1985).
27. M. Schulze et al., *Kidney Int* 40, 533-8 (September, 1991).
28. Y. Morita et al., *J Am Soc Nephrol* 11, 700-7 (April, 2000).
29. Y. Hori et al., *Kidney Int* 56, 2096-106. (1999).
30. R. J. Quigg, *Kidney Int* 56, 2314-5. (1999).
31. 1995. *PCR Primer. A laboratory manual.* Cold Spring Harbor: Cold Spring Harbor Laboratory Press.
32. Mendrick, D. L., et al. 1983. *Laboratory Investigation* 49:107-117.
33. Sharkey, R. M., et al. 1990. *Cancer Res.* 50: 2330-2336.
34. Hsu, S. I., and W. G. Couser. 2003. *J Am Soc Nephrol* 14:S186-191.
35. Sheerin, N. S., and S. H. Sacks. 2002. *Clin Exp Immunol* 130:1-3.
36. Sakurada, C., H. Seno, N. Dohi, H. Takizawa, M. Nonaka, N. Okada, and H. Okada. 1994. Molecular cloning of the rat complement regulatory protein, 512 antigen. *Biochem. Biophys. Res. Commun.* 198:819.
37. Hughes, T. R., S. J. Piddlesden, J. D. Williams, R. A. Harrison, and B. P. Morgan. 1992. Isolation and characterization of a membrane protein from rat erythrocytes which inhibits lysis by the membrane attack complex of rat complement. *Biochem. J.* 284:169.
38. Rushmere, N. K., R. A. Harrison, C. W. van der Berg, and B. P. Morgan. 1994. Molecular cloning of the rat analogue of human CD59: structural comparison with human CD59 and identification of a putative active site. *Biochem. J.* 304:595.
39. Rushmere, N. K., C. W. Van Den Berg, and B. P. Morgan. 2000. Production and functional characterization of a soluble recombinant form of mouse CD59. *Immunology* 99:326.
40. Zhang H f, H., S. Lu, S. L. Morrison, and S. Tomlinson. 2001. Targeting of functional antibody-decay accelerating factor (DAF) fusion proteins to a cell surface. *J. Biol. Chem.* 14:14.
41. Sharkey, R. M., A. Natale, D. M. Goldenberg, and M. J. Mattes. 1991. Rapid blood clearance of immunoglobulin G2a and immunoglobulin G2b in nude mice. *Cancer Res.* 51:3102.
42. Morgan, B. P. 2000. Measurement of complement hemolytic activity. In *Complement Methods and Protocols.* B. P. Morgan, ed. Humana Press, Totowa, N.J., p. 61.
43. Meldrum, K. K., D. R. Meldrum, X. Meng, L. Ao, and A. H. Harken. 2002. TNF-α-dependent bilateral renal injury is induced by unilateral renal ischemiareperfusion. *Am. J. Physiol. Heart Circ. Physiol.* 282:H540.
44. He C, Imai M, Song H, Quigg RJ, Tomlinson S. Complement inhibitors targeted to the proximal tubule prevent injury in experimental nephrotic syndrome and demonstrate a key role for C5b-9. *J Immunol.* In press.
45. Blouch K, Deen W M, Fauvel J P, Bialek J, Derby G, Myers B D. Molecular configuration and glomerular size selectivity in healthy and nephrotic humans. *Am. J. Physiol.* 273:F430-F437, 1997.
46. Nath K A. Tubulointerstitial changes as a major determinant in the progression of renal damage. *Am. J. Kid. Dis.* 20:1-17, 1992.
47. Eddy A A, McCulloch L, Liu E, Adams J. A relationship between proteinuria and acute tubulointerstitial disease in rats with experimental nephrotic syndrome. *Am. J. Pathol.* 138:1111-1123, 1991.
48. Zoja C, Morigi M, Remuzzi G. Proteinuria and phenotypic change of proximal tubular cells. *J. Am. Soc. Nephrol.* 14 Suppl 1:S36-S41, 2003.
49. Mosolits S, Magyarlaki T, Nagy J. Membrane attack complex and membrane cofactor protein are related to tubulointerstitial inflammation in various human glomerulopathies. *Nephron.* 75:179-187, 1997.
50. Ogrodowsi J L, Hebert L A, Sedmak D, Cosio F G, Tamerius J, Kolb W. Measurement of SC5b-9 in urine in patients with the nephrotic syndrome. *Kidney Int.* 40:1141-1147, 1991.
51. Peake P W, Pussell B A, Mackinnon B, Charlesworth J A. The effect of pH and nucleophiles on complement activation by human proximal tubular epithelial cells. *Nephrol. Dial. Transplant.* 17:745-752, 2002.
52. Bailly V, Zhang Z, Meier W, Cate R, Sanicola M, Bonventre J V. Shedding of kidney injury molecule-1, a putative adhesion protein involved in renal regeneration. *J. Biol. Chem.* 277:39739-39748, 2002.
53. Ichimura T, Bonventre J V, Bailly V et al. Kidney injury molecule-1 (KIM-1), a putative epithelial cell adhesion molecule containing a novel immunoglobulin domain, is up-regulated in renal cells after injury. *J. Biol. Chem.* 273: 4135-4142, 1998.
54. Quigg R J, Cybulsky A V, Jacobs J B, Salant D J. Anti-Fx1A produces complement-dependent cytotoxicity of glomerular epithelial cells. *Kidney Int.* 34:43-52, 1988.
55. Braun M C, Reins R Y, Li T B et al. Renal expression of the C3a receptor and functional responses of primary human proximal tubular epithelial cells. *J. Immunol.* 173:4190-4196, 2004.
56. Zahedi R, Braun M, Wetsel R A et al. The C5a receptor is expressed by human renal proximal tubular epithelial cells. *Clin. Exp. Immunol.* 121:226-233, 2000.
57. Nath K A, Hostetter M K, Hostetter T H. Pathophysiology of chronic tubulo-interstitial disease in rats. Interactions of dietary acid load, ammonia, and complement component C3. *J. Clin. Invest.* 76:667-675, 1985.
58. Passwell J, Schreiner G F, Nonaka M, Beuscher H U, Colten H R. Local extrahepatic expression of complement genes C3, factor B, C2 and C4 is increased in murine lupus nephritis. *J. Clin. Invest.* 82:1676-1684, 1988.
59. Timmerman J J, Van der Woude F J, Gijlswijk-Janssen D J, Verweij C L, Van Es L A, Daha M R. Differential expression of complement components in human fetal and adult kidneys. *Kidney Int.* 49:730-740, 1996.
60. Tang S, Lai K N, Chan T M, Lan H Y, Ho S K, Sacks S H. Transferrin but not albumin mediates stimulation of complement C3 biosynthesis in human proximal tubular epithelial cells. *Am. J. Kidney Dis.* 37:94-103, 2001.

61. Pippin J W, Durvasula R, Petermann A, Hiromura K, Couser W G, Shankland S J. DNA damage is a novel response to sublytic complement C5b-9-induced injury in podocytes. *J. Clin. Invest.* 111:877-885, 2003.
62. Nangaku M, Shankland S J, Couser W G. Cellular Response to Injury in Membranous Nephropathy. *J Am Soc Nephrol.* Mar. 30, 2005
63. Aguado M T, Lambris J D, Tsokos G C et al. Monoclonal antibodies against complement 3 neoantigens for detection of immune complexes and complement activation. Relationship between immune complex levels, state of C3, and numbers of receptors for C3b. *J. Clin. Invest.* 76:1418-1426, 1985.
64. Daha M R, Van K C. Is the proximal tubular cell a proinflammatory cell? *Nephrol. Dial. Transplant.* 15 Suppl 6:41-43, 2000.
65. Nauta A J, de H S, Bottazzi B et al. Human renal epithelial cells produce the long pentraxin PTX3. *Kidney Int.* 67:543-553, 2005.
66. Cosio F G, Shibata T, Rovin B H, Birmingham D J. Effects of complement activation products on the synthesis of decay accelerating factor and membrane cofactor protein by human mesangial cells. *Kidney. Int.* 46:986-992, 1994.
67. Cybulsky A V, Quigg R J, Salant D J. Experimental membranous nephropathy redux. *Am J Physiol Renal, Fluid Electrolyte Physiol.* In press.
Higuchi T, Orita T, Nakanishi S et al. Molecular cloning, genomic structure, and expression analysis of MUC20, a novel mucin protein, up-regulated in injured kidney. *J. Biol. Chem.* 279:1968-1979, 2004.
69. Higuchi T, Orita T, Katsuya K et al. MUC20 suppresses the hepatocyte growth factor-induced Grb2-Ras pathway by binding to a multifunctional docking site of met. *Mol. Cell Biol.* 24:7456-7468, 2004.
70. Hussain M M, Strickland D K, Bakillah A. The mammalian low-density lipoprotein receptor family. *Annu. Rev. Nutr.* 19:141-172, 1999.
71. Weihofen W A, Liu J, Reutter W, Saenger W, Fan H. Crystal structure of CD26/dipeptidyl-peptidase IV in complex with adenosine deaminase reveals a highly amphiphilic interface. *J. Biol. Chem.* 279:43330-43335, 2004.
72. Oeffier C, D'Arcy A, Hennig M, Winkler F K, Dale G E. Structure of human neutral endopeptidase (Neprilysin) complexed with phosphoramidon. *J. Mol. Biol.* 296:341-349, 2000.
73. Hiramatsu H, Kyono K, Higashiyama Y et al. The structure and function of human dipeptidyl peptidase IV, possessing a unique eight-bladed beta-propeller fold. *Biochem. Biophys. Res. Commun.* 302:849-854, 2003.
74. Tam J P. Synthetic peptide vaccine design: synthesis and properties of a high-density multiple antigenic peptide system. *Proc. Natl. Acad. Sci. U.S.A.* 85:5409-5413, 1988.
75. Shin S U, Morrison S L. Expression and characterization of an antibody binding specificity joined to insulin-like growth factor 1: potential applications for cellular targeting. *Proc. Natl. Acad. Sci. U.S.A.* 87:5322-5326, 1990.
76. Shin S U, Morrison S L. Production and properties of chimeric antibody molecules. *Methods Enzymol.* 178:459-476, 1989.

G. Sequences
 1. DAF
Nucleotide Sequence corresponds to SEQ ID NO: 1
Amino Acid Sequence corresponds to SEQ ID NO: 2
 2. CD59
Nucleotide Sequence corresponds to SEQ ID NO: 3
Amino Acid Sequence corresponds to SEQ ID NO: 4
 3. CR1
Nucleotide Sequence corresponds to SEQ ID NO: 5
Amino Acid Sequence corresponds to SEQ ID NO: 6
 4. MCP
Nucleotide Sequence corresponds to SEQ ID NO: 7
Amino Acid Sequence corresponds to SEQ ID NO: 8
 5. Mouse Crry
Amino Acid Sequence corresponds to SEQ ID NO: 9
 6. K9/9
Amino Acid Sequence corresponds to SEQ ID NO: 10
 7. K9/9-Crry (tCrry)
Amino Acid Sequence corresponds to SEQ ID NO: 11
 8. K9/9-CD59 (tCD59)
Amino Acid Sequence corresponds to SEQ ID NO: 12
 9. dipeptidylpeptidase IV (DPPIV) Accesssion No. NP_001926
Amino acid Sequence corresponds to SEQ ID NO: 13
 10. Mucin 20 Accession No. NP_689886
Amino acid Sequence corresponds to SEQ ID NO: 14
 11. KIM-1 (hepatitis A Virus Cellular Receptor 1) Accession No. NP_036338
Amino acid Sequence corresponds to SEQ ID NO: 15

| | |
|---|---|
| ATGAAGTTGCCTGTTAGGCTGTTGGTGCTG | (SEQ ID NO: 16) |
| ACTGGATGGTGGGAAGATGG | (SEQ ID NO: 17) |
| ATGAAATGCAGCTGGGGCATGTTCTTC | (SEQ ID NO: 18) |
| CAGTGGATAGACCGATGGGCC | (SEQ ID NO: 19) |
| SDCIKSAARLIQN | (SEQ ID NO: 20) |
| FEVEDQIEAARQFS | (SEQ ID NO: 21) |
| FFKYACGGWLKR | (SEQ ID NO: 22) |
| YGGYVTSMVL | (SEQ ID NO: 23) |
| SKHVVEDLIAQIREVFIQTLDD | (SEQ ID NO: 24) |
| FQQSAQISKALVDV | (SEQ ID NO: 25) |
| AETKLKLRAEEKALA | (SEQ ID NO: 26) |
| STAHQHIYTHIMSHIFTKQCF | (SEQ ID NO: 27) |

What is claimed:

1. A composition, comprising a fusion protein or immunocojugate, wherein the fusion protein or immunocojugate comprises a proximal tubule targeting moiety and a modulator of complement activity, wherein the modulator of complement activity comprises a complement inhibitor, wherein the complement inhibitor comprises decay accelerating factor (DAF) as set forth in SEQ ID NO. 2.

2. A composition, comprising a fusion protein or immunocojugate, wherein the fusion protein or immunocojugate comprises a proximal tubule targeting moiety and a modulator of complement activity, wherein the modulator of complement activity comprises a complement inhibitor, wherein the complement inhibitor comprises human CD59 as set forth in SEQ ID NO. 4, and wherein the targeting moiety is not Complement Receptor 2 (CR2).

3. A composition, comprising a fusion protein or immunocojugate, wherein the fusion protein or immunocojugate comprises a proximal tubule targeting moiety and a modulator of complement activity, wherein the modulator of complement activity comprises a complement inhibitor, wherein the complement inhibitor comprises complement receptor 1 (CR1) as set forth in SEQ ID NO. 6.

4. A composition, comprising a fusion protein or immunocojugate, wherein the fusion protein or immunocojugate comprises a proximal tubule targeting moiety and a modulator of complement activity, wherein the modulator of complement activity comprises a complement inhibitor, wherein the complement inhibitor comprises membrane cofactor protein (MCP) as set forth in SEQ ID NO. 8.

5. A composition, comprising a fusion protein or immunocojugate, wherein the fusion protein or immunocojugate comprises a proximal tubule targeting moiety and a modulator of complement activity, wherein the modulator of complement activity comprises a complement inhibitor, wherein the complement inhibitor comprises complement receptor-related protein y (Crry) as set forth in SEQ ID NO. 9.

* * * * *